US012644134B2

(12) United States Patent
　　Thon

(10) Patent No.: US 12,644,134 B2
(45) **Date of Patent: *Jun. 2, 2026**

(54) COMPOSITIONS AND METHODS RELATED TO MEGAKARYOCYTE-DERIVED EXTRACELLULAR VESICLES FOR TREATING MYELOPROLIFERATIVE NEOPLASMS

(71) Applicant: STRM.bio Incorporated, Cambridge, MA (US)

(72) Inventor: Jonathan Thon, Cambridge, MA (US)

(73) Assignee: STRM.bio Incorporated, Cambridge, MA (US)

( * ) Notice: Subject to any disclaimer, the term of this patent is extended or adjusted under 35 U.S.C. 154(b) by 628 days.

This patent is subject to a terminal disclaimer.

(21) Appl. No.: 18/032,999

(22) PCT Filed: Oct. 23, 2021

(86) PCT No.: PCT/US2021/056377
§ 371 (c)(1),
(2) Date: Apr. 20, 2023

(87) PCT Pub. No.: WO2022/087505
PCT Pub. Date: Apr. 28, 2022

(65) Prior Publication Data
US 2023/0392168 A1　Dec. 7, 2023

Related U.S. Application Data

(60) Provisional application No. 63/209,084, filed on Jun. 10, 2021, provisional application No. 63/173,735, filed on Apr. 12, 2021, provisional application No. 63/104,769, filed on Oct. 23, 2020.

(51) Int. Cl.

| | |
|---|---|
| *C12N 15/88* | (2006.01) |
| *A61K 9/1272* | (2025.01) |
| *A61K 48/00* | (2006.01) |
| *A61P 35/00* | (2006.01) |
| *C12N 5/078* | (2010.01) |
| *C12N 9/22* | (2006.01) |
| *C12N 15/11* | (2006.01) |
| *C12N 15/90* | (2006.01) |

(52) U.S. Cl.
CPC ............ *C12N 15/88* (2013.01); *A61K 9/1272* (2013.01); *A61K 48/0033* (2013.01); *A61P 35/00* (2018.01); *C12N 5/0644* (2013.01); *C12N 9/22* (2013.01); *C12N 15/111* (2013.01); *C12N 15/907* (2013.01); *C12N 2310/20* (2017.05); *C12N 2506/11* (2013.01)

(58) Field of Classification Search
None
See application file for complete search history.

(56) References Cited

U.S. PATENT DOCUMENTS

| | | | |
|---|---|---|---|
| 9,085,778 | B2 | 7/2015 | Lötvall et al. |
| 9,629,929 | B2 | 4/2017 | Lötvall et al. |
| 9,856,477 | B2 | 1/2018 | Lötvall et al. |
| 9,889,210 | B2 | 2/2018 | Lötvall et al. |
| 10,195,290 | B1 | 2/2019 | Dooley et al. |
| 10,370,663 | B2 | 8/2019 | Lötvall et al. |
| 10,538,738 | B2 | 1/2020 | Papoutsakis et al. |
| 10,561,740 | B2 | 2/2020 | Dooley et al. |
| 10,695,443 | B2 | 6/2020 | Lötvall et al. |
| 10,723,782 | B2 | 7/2020 | Lewis et al. |
| 11,512,315 | B2 | 11/2022 | Sathyanarayanan et al. |
| 2001/0005591 | A1 | 6/2001 | Qasba et al. |
| 2004/0152628 | A9 | 8/2004 | Tandon et al. |
| 2008/0069807 | A1 | 3/2008 | Jy et al. |
| 2008/0213377 | A1 | 9/2008 | Bhatia et al. |
| 2012/0238020 | A1 | 9/2012 | Mitchell et al. |
| 2012/0315338 | A1 | 12/2012 | Li et al. |
| 2012/0321723 | A1 | 12/2012 | Bruno et al. |
| 2017/0058262 | A1 | 3/2017 | Papoutsakis et al. |
| 2018/0055891 | A1 | 3/2018 | Zhao |
| 2018/0282762 | A1 | 10/2018 | Gori |
| 2018/0355414 | A1 | 12/2018 | Kim et al. |
| 2019/0071717 | A1 | 3/2019 | Zhang et al. |
| 2019/0202892 | A1 | 7/2019 | Lewis et al. |
| 2019/0292586 | A1 | 9/2019 | Chen et al. |
| 2020/0063114 | A1 | 2/2020 | Fauser et al. |
| 2020/0115681 | A1 | 4/2020 | Papoutsakis et al. |
| 2022/0143095 | A1 | 5/2022 | Hett et al. |

FOREIGN PATENT DOCUMENTS

| | | | |
|---|---|---|---|
| WO | WO 2014/168548 | A2 | 10/2014 |
| WO | WO 2015/179301 | A1 | 11/2015 |
| WO | WO 2017/044149 | A1 | 3/2017 |

(Continued)

OTHER PUBLICATIONS

Herrmann, et al., "Extracellular vesicles as a next-generation drug delivery platform," Nature Nanotechnology, vol. 16, pp. 748-759, Jul. 2021.

(Continued)

*Primary Examiner* — Manjunath N Rao
*Assistant Examiner* — Jae W Lee
(74) *Attorney, Agent, or Firm* — Morgan, Lewis & Bockius LLP

(57) ABSTRACT

Disclosed herein are compositions and methods related to treating myeloproliferative diseases or disorders, such as MPN, using megakaryocyte-derived extracellular vesicles, including megakaryocyte-derived extracellular vesicles derived from human pluripotent stem cells.

12 Claims, 36 Drawing Sheets

Specification includes a Sequence Listing.

(56)     References Cited

FOREIGN PATENT DOCUMENTS

| WO | WO 2018/165308 A1 | 9/2018 |
|----|-------------------|--------|
| WO | WO 2019/136318 A2 | 7/2019 |
| WO | WO 2020/006539 A1 | 1/2020 |
| WO | WO 2020/018950 A1 | 1/2020 |
| WO | WO 2020/113059 A1 | 6/2020 |
| WO | WO 2021/138332 A1 | 7/2021 |
| WO | WO 2021/173828 A1 | 9/2021 |
| WO | WO 2021/231425 A1 | 11/2021 |
| WO | WO 2022/081836 A1 | 4/2022 |

OTHER PUBLICATIONS

Li, et al., "JAK2 V617F impairs hematopoietic stem cell function in a conditional knock-in mouse model of JAK2 V617F-positive essential thrombocythemia," Blood, vol. 116, No. 9, pp. 1528-1538, Sep. 2010.

Uddin, et al., "CRISPR Gene Therapy: Applications, Limitations, and Implications for the Future," Frontiers in Oncology, vol. 10, 17 pages, Aug. 2020.

International Search Report & Written Opinion PCT Application No. PCT/US21/56377, dated Feb. 23, 2022, 18 pages.

Jiang, et al., "How do megakaryocytic microparticles target and deliver cargo to alter the fate of hematopoietic stem cells?" J Control Release, vol. 247, pp. 1-18, Feb. 2017.

Gilligan, Cells 2020, 9, 224; doi:10.3390/cells9010224.

Kamerkar, Nature. Jun. 22, 2017; 546(7659): 498-503. doi:10.1038/nature22341.

Schlinker, Biotechnol Bioeng. Apr. 2015; 112(4): 788-800.

Kotmakçi, J Pharm Pharm Sci 18(3) 396-413, 2015.

Gangat, American Journal of Hematology, vol. 91, No. 1, Jan. 2016.

Stein, Clin Cancer Res. Jan. 1, 2016; 22(1): 16-19.

Kanada, et al., "Differential fates of biomolecules delivered to target cells via extracellular vesicles," PNAS, vol. 112, No. 12, pp. E1433-E1442, Feb. 23, 2015.

Arraud, et al., "Extracellular vesicles from blood plasma: determination of their morphology, size, phenotype and concentration,"

Journal ofThrombosis and Haemostasis, vol. 12, pp. 614-217, 2014.

Berge, eta/., "Pharmaceutical Salts," Pharmaceutical Sciences, vol. 66, No. 1, 19, pp. 1977.

Brisson, et al., "Extracellular vesicles from activated platelets: a semiquantitative cryo-electron microscopy and immuno-gold labelinq study," Platelets, vol. 28, No. 3, DD. 263-271, 2017.

Bulcha, et al., "Viral vector platforms within the gene therapy landscape," Signal Transduction and Targeted TheraDv, vol. 6, No. 53, 24 Daqes, 2021.

Epstein, "Cosmeceutical vehicles," Clinics in Dermatology, vol. 27, pp. 453-460, 2009.

Escobar, et al., "Human megakaryocytic microparticles induce de novo platelet biogenesis in a wild-type murine model," Blood Advances, vol. 4, No. 5, pp. 804-814, 2020.

Flaumenhaft, et al., "Megakaryocyte-derived microparticles: direct visualization and distinction from platelet-derived microparticles," Blood, vol. 113, No. 5, DD. 1112-1121, 2009.

French, et al., "Platelet-derived extracellular vesicles infiltrate and modify the bone marrow during inflammation," Blood Advances, vol. 4, No. 13, pp. 3011-3023, 2020.

Jiang, et al., "How do megakaryocytic microparticles target and deliver cargo to alter the fate of hematopoietic stem cells?" J Control Release, vol. 247, DD. 1-18, 2017.

Jiang, et al., "Shear enhances thrombopoiesis and formation of microparticles that induce megakaryocytic differentiation of stem cells," Blood, vol. 124, No. 13, pp. 2094-2103, 2014.

Kao, et al., "Engineering human megakaryocytic microparticles for targeted delivery of nucleic acids to hematopoietic stem and progenitor cells," Sci. Adv., vol. 4, 11 paqes, 2018.

Kao, et al., "Extracellular vesicles: exosomes, microparticles, their parts, and their targets to enable their biomanufacturing and clinical applications," Current Opinion in Biotechnology, vol. 60, pp. 89-98, 2019.

Stahl, et al., "Handbook of Pharmaceutical Salts: Properties, Selection, and Use," Journal of Medicinal Chemistry, vol. 46, No. 7, pp. 1277-1278, 2003.

Zeltner, et al., "Near-perfect infectivity of wild-type AAV as benchmark for infectivity of recombinant AAV vectors," Gene Ther., vol. 17, No. 7, DD. 872-879, 2010.

Zhou, et al., "A pneumonia outbreak associated with a new coronavirus of probable bat origin," Nature, vol. 579, 20 pages, 2020.

Negative control

CD41/CD61+ MkEVs

FIG. 4D                                    FIG. 4E
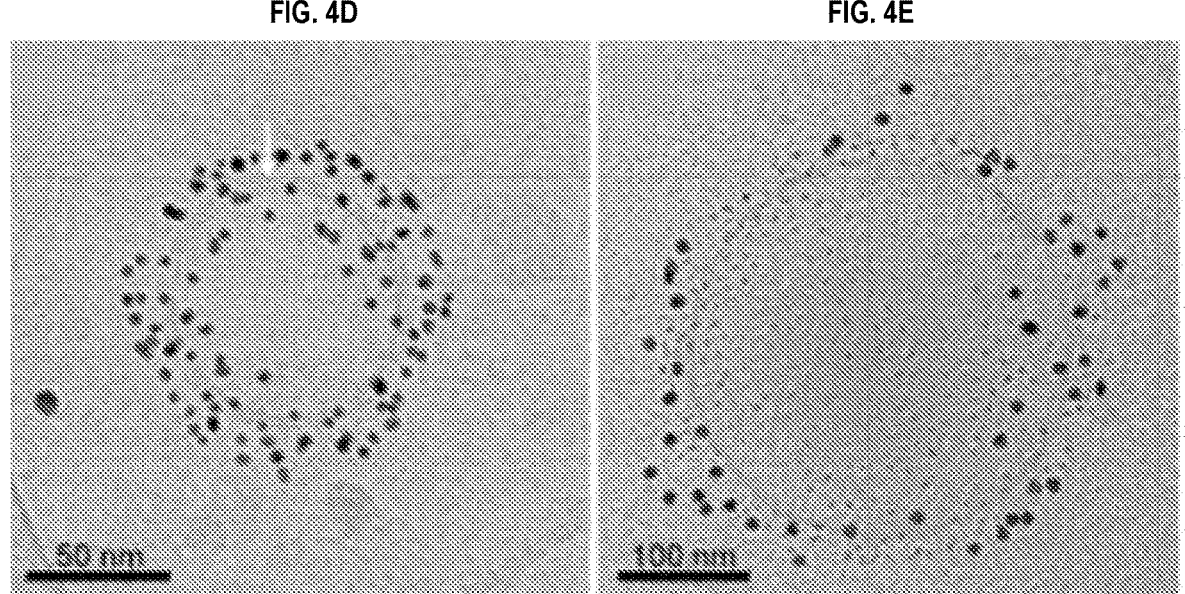

Unfiltered MkEV Product

650nm Filtered MkEV Product

FIG. 6A                                    FIG. 6B
FIG. 6C                                    FIG. 6D
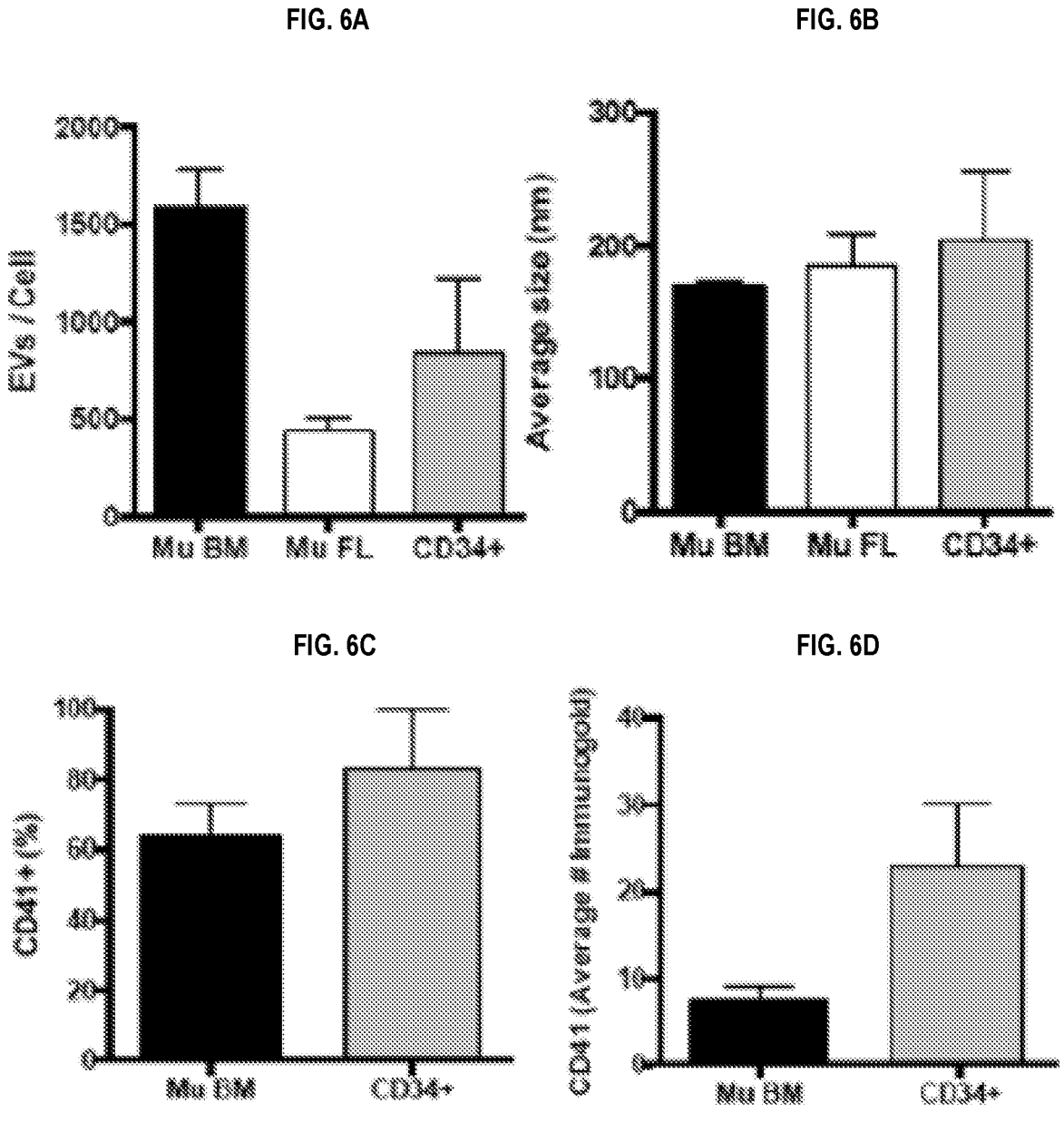

Control cells, unmanipulated

GFP+ cells

Unloaded
MkEVs

RNP
(filtered)

Cargo-loaded
MkEVs
(80 MkEVs/cell)

Cargo-loaded
MkEVs
(155 MkEVs/cell)

Cargo-loaded
MkEVs
(465 MkEVs/cell)

Cells          Singlets          Viable cells          GFP+ cells

Cells     Singlets     Viable cells     GFP+ cells

Brightfield       GFP       Merge

RNP
(filtered)

MkEVs +RNP,
no electroporation
(670 MkEVs/cell)

Cargo-loaded
MkEVs
(670 MkEVs/cell)

Cargo-loaded
MkEVs
(2000 MkEVs/cell)

Cells     Singlets     Viable cells     GFP+ cells

RNP
(filtered)

MkEVs +RNP,
no electroporation
(890 MkEVs/cell)

Cargo-loaded
MkEVs
(890 MkEVs/cell)

Cargo-loaded
MkEVs
(2570 MkEVs/cell)

Cells          Singlets          Viable cells          GFP+ cells

COMPOSITIONS AND METHODS RELATED TO MEGAKARYOCYTE-DERIVED EXTRACELLULAR VESICLES FOR TREATING MYELOPROLIFERATIVE NEOPLASMS

CROSS-REFERENCE TO RELATED APPLICATIONS

This application is a 35 U.S.C. § 371 national phase application of International Patent Application No. PCT/US2021/056377, filed Oct. 23, 2021, which claims benefit of priority to U.S. Provisional Patent Application Nos. 63/104,769, filed Oct. 23, 2020, 63/173,735, filed Apr. 12, 2021, and 63/209,084, filed Jun. 10, 2021, all of which are incorporated by reference herein in their entireties.

SEQUENCE LISTING

The instant application contains a Sequence Listing that has been submitted in ASCII format via EFS-Web and is hereby incorporated by reference in its entirety. Said ASCII copy, created on Apr. 20, 2023, is named "STRM-004_126555-5004_SL_ST25.TXT" and is 1,108 bytes in size.

FIELD

The present disclosure relates to compositions and methods related to megakaryocyte-derived extracellular vesicles derived from human pluripotent stem cells for the treatment of a myeloproliferative disease or disorder, such as, for example, a myeloproliferative neoplasm (MPN).

BACKGROUND

The direct administration of therapeutic agents to patients without the use of delivery vehicles, has several disadvantages, including rapid clearance, poor bioavailability, low delivery to target cells or tissues, unspecific cytotoxicity, and consequent systemic side effects. Treatment using nanodelivery vehicles can have several advantages, including reducing renal clearance, improving site-specific delivery, simultaneous delivery of multiple therapeutic agents, protection from enzymatic degradation, immunoevasion, sequential multistage release, stimuli-responsive activation, and theranostic capabilities, among others. Nevertheless, the majority of these features are not yet in clinical use, partially due to complex and costly manufacturing required to achieve multi-functionality. The largest category of clinically approved nanoparticles is liposomes, which consist of a simple lipid bilayer surrounding an aqueous compartment. However, liposomes can also trigger adverse effects in a patient, including immune reactions and cytotoxicity, in addition to target non-specificity and inefficient unloading of therapeutic agents, because liposomes are foreign, synthetic entities, with limited cell or tissue targeting machinery. Adenovirus, retrovirus, AAV, and lentivirus vectors are currently the most popular viral vectors for gene therapy today; however, these modalities suffer from targeting, scalability of manufacture, immunogenicity, and safety concerns.

Hematologic malignancies are forms of cancer that begin in the cells of blood-forming tissue, such as the bone marrow, or in the cells of the immune system. Examples of hematologic cancer are acute and chronic leukemias, lymphomas, multiple myeloma and myelodysplastic syndromes.

Myeloproliferative neoplasms, or MPNs, are hematologic neoplasms that arise from neoplastic hematopoietic myeloid progenitor cells in the bone marrow, such as the precursor cells of red cells, platelets and granulocytes. Proliferation of neoplastic progenitor cells leads to an overproduction of any combination of white cells, red cells and/or platelets, depending on the disease. These overproduced cells may also be abnormal, leading to additional clinical complications. Treatments for MPNs are lacking and mainly focused on symptoms, not cures.

Accordingly, there is a need for delivery vehicles that can be generated cost-effectively at scale and that eliminate or reduce adverse effects when administered to a patient, and that can also provide novel treatments for MPNs that target the neoplastic progenitor cells responsible for the disease's malignant phenotype, particularly, e.g., in individuals who are resistant to or experience adverse events as a result of taking commonly prescribed front-line therapies for this disorder.

SUMMARY

Disclosed herein are compositions and methods related to megakaryocyte-derived extracellular vesicles useful for treating myeloproliferative diseases or disorders, such as a myeloproliferative neoplasm (MPN). Specifically, inter alia, the present megakaryocyte-derived extracellular vesicles demonstrate a unique biomarker profile and/or size profile, which make them well-suited for utilization in therapeutic delivery for treating myeloproliferative diseases or disorders, such as a myeloproliferative neoplasm (MPN). In various embodiments, the compositions and methods disclosed herein may be utilized for drug delivery and treatment of myeloproliferative diseases or disorders, such as a myeloproliferative neoplasm (MPN). The compositions and methods disclosed herein may be utilized for drug delivery and treatment of a disease or disorder that is, or is related to, a myeloproliferative disease or disorder, such as, for example, a myeloproliferative neoplasm (MPN). The methods disclosed herein may be in vivo or ex vivo and may be used in for example, gene replacement therapy and gene-editing.

In another aspect, the present invention relates to a method for gene editing a cell. In some embodiments, the method includes (a) contacting the cell with a composition comprising a plurality of substantially purified megakaryocyte-derived extracellular vesicles disclosed herein comprising a lipid bilayer membrane surrounding a lumen, wherein: the megakaryocyte-derived extracellular vesicle lumen comprises cargo comprising an agent suitable for gene editing the cell and/or cargo comprising an agent suitable for gene editing the cell is associated with the surface of the megakaryocyte-derived extracellular vesicles; and the lipid bilayer membrane comprises one or more proteins associated with or embedded within, and (b) gene editing the cell to alter a mutation in a JAK2 gene therein.

In another aspect, the present invention relates to a method for treating a myeloproliferative disease or disorder, comprising (a) obtaining a plurality of substantially purified megakaryocyte-derived extracellular vesicles disclosed herein; (b) incubating the plurality of substantially purified megakaryocyte-derived extracellular vesicles with a therapeutic agent to allow the therapeutic agent to populate the lumen of the megakaryocyte-derived extracellular vesicle and/or associate with the surface of the megakaryocyte-derived extracellular vesicle and yield a deliverable therapeutic agent, wherein the therapeutic agent is capable of treating a myeloproliferative disease or disorder; and (c) administering the deliverable therapeutic agent to a patient or contacting the deliverable therapeutic agent with a biological cell in vitro and administering the contacted biological cell to a patient, wherein the megakaryocyte-derived extracellular vesicles are substantially purified and comprise a lipid bilayer membrane surrounding a lumen, the megakaryocyte-derived extracellular vesicle lumen comprises the therapeutic agent and/or is associated with the surface of the megakaryocyte-derived extracellular vesicle; and the lipid bilayer membrane comprises one or more proteins associated with or embedded within. In another aspect, the present invention relates to a pharmaceutical composition comprising a composition comprising megakaryocyte-derived extracellular vesicles disclosed herein and a pharmaceutically acceptable excipient or carrier. In some embodiments, the megakaryocyte-derived extracellular vesicles comprise cargo comprising one or more agents, such as one or more therapeutic agents, useful for the treatment of a myeloproliferative disease or disorder, such as, for example, a myeloproliferative neoplasm (MPN).

In another aspect, the present invention relates to a method for transferring a deliverable therapeutic agent, comprising: (a) obtaining the megakaryocyte-derived extracellular vesicles of a composition disclosed herein; (b) incubating the megakaryocyte-derived extracellular vesicles with a therapeutic agent to allow the therapeutic agent to populate the lumen of the megakaryocyte-derived extracellular vesicle and/or associate with the surface of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient.

In some embodiments, the myeloproliferative disease or disorder is an MPN.

BRIEF DESCRIPTION OF THE DRAWINGS

FIGS. 2A-2B are representative graphs demonstrating the flow cytometry gating strategy. FIG. 2C is a representative graph demonstrating the marker profile of CD41+ MKEVs of the disclosure, CD41+ PFP MkEVs, and CD41+ PLT EVs. MKEVs of the disclosure have different surface marker phenotypes compared to naturally occurring MkEVs and platelet-derived EVs. Differential expression of surface markers co-expressed on CD41+ STRM MkEVs (black bars) when compared to CD41+ naturally occurring platelet free plasma (PFP) MkEVs (hashed bars) and CD41+ plate-

Figure 2A:
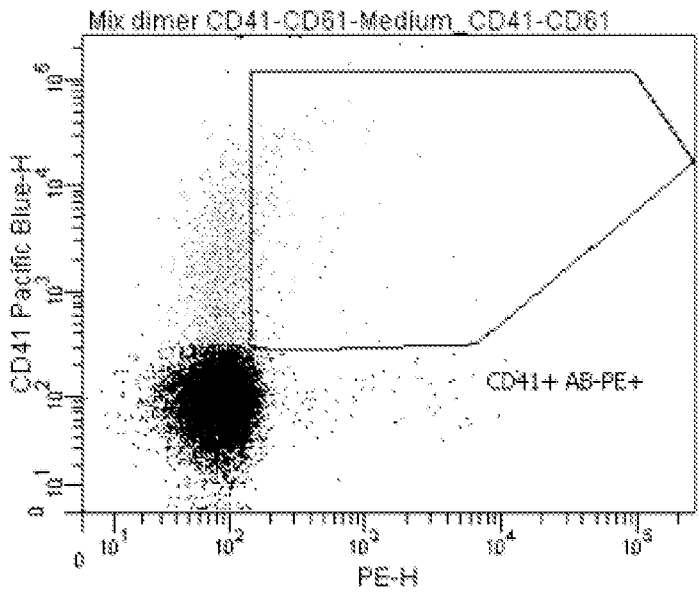
FIGS. 2A-2F demonstrate experimental data showing MkEV biomarker expression. Surface marker expression of MkEVs of the disclosure were compared to platelet-free plasma (PFP) MkEVs and platelet-derived EVs (PLT EVs).
Figure 2B:
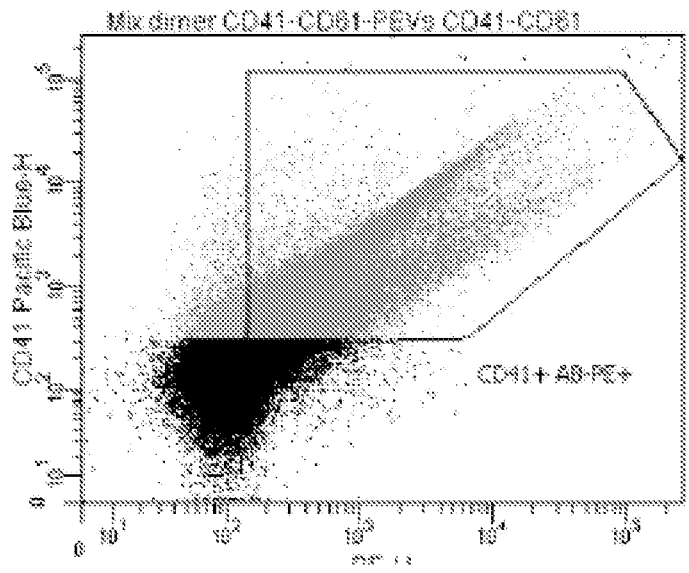
Figure 2C:
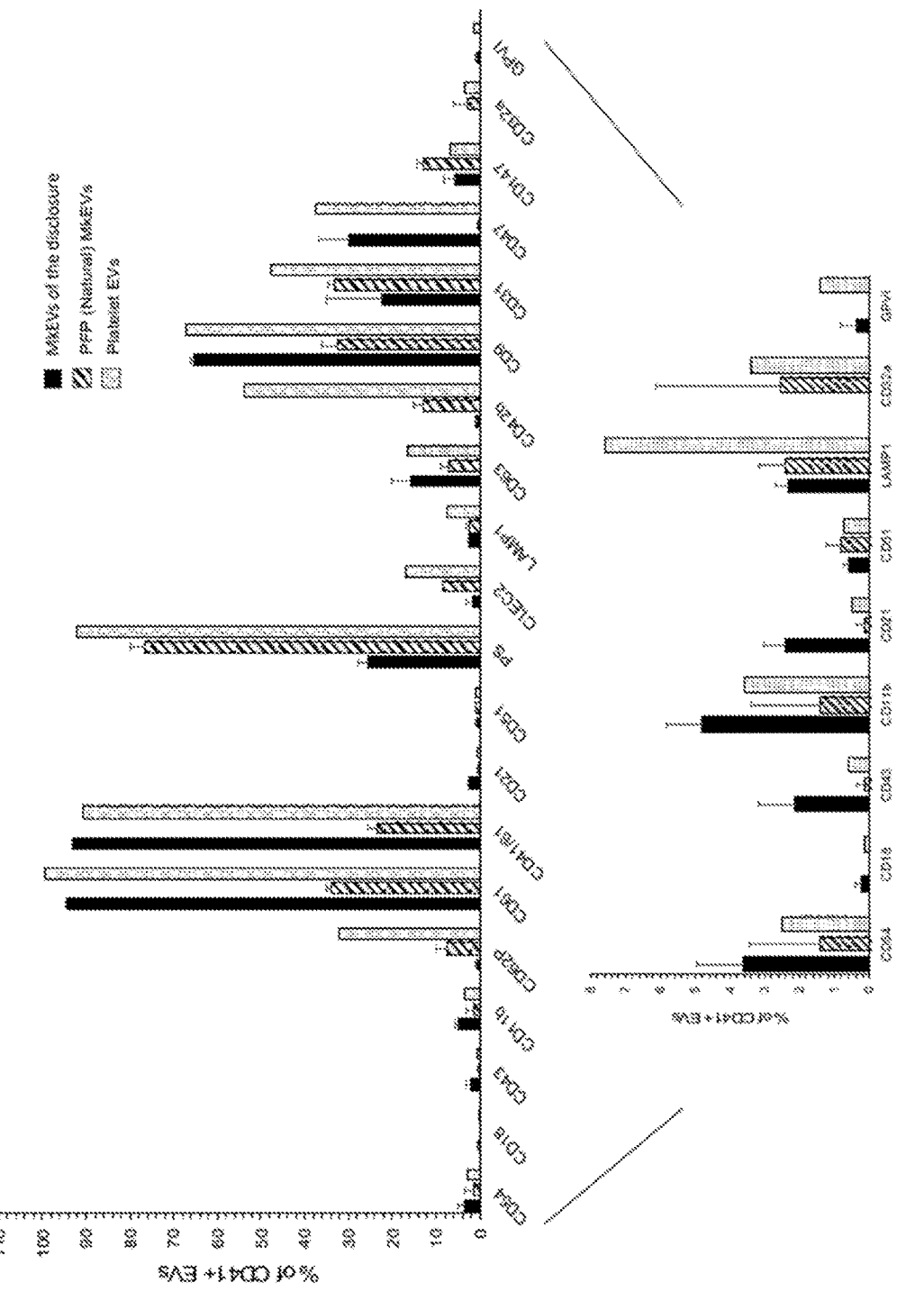
Figure 2D:
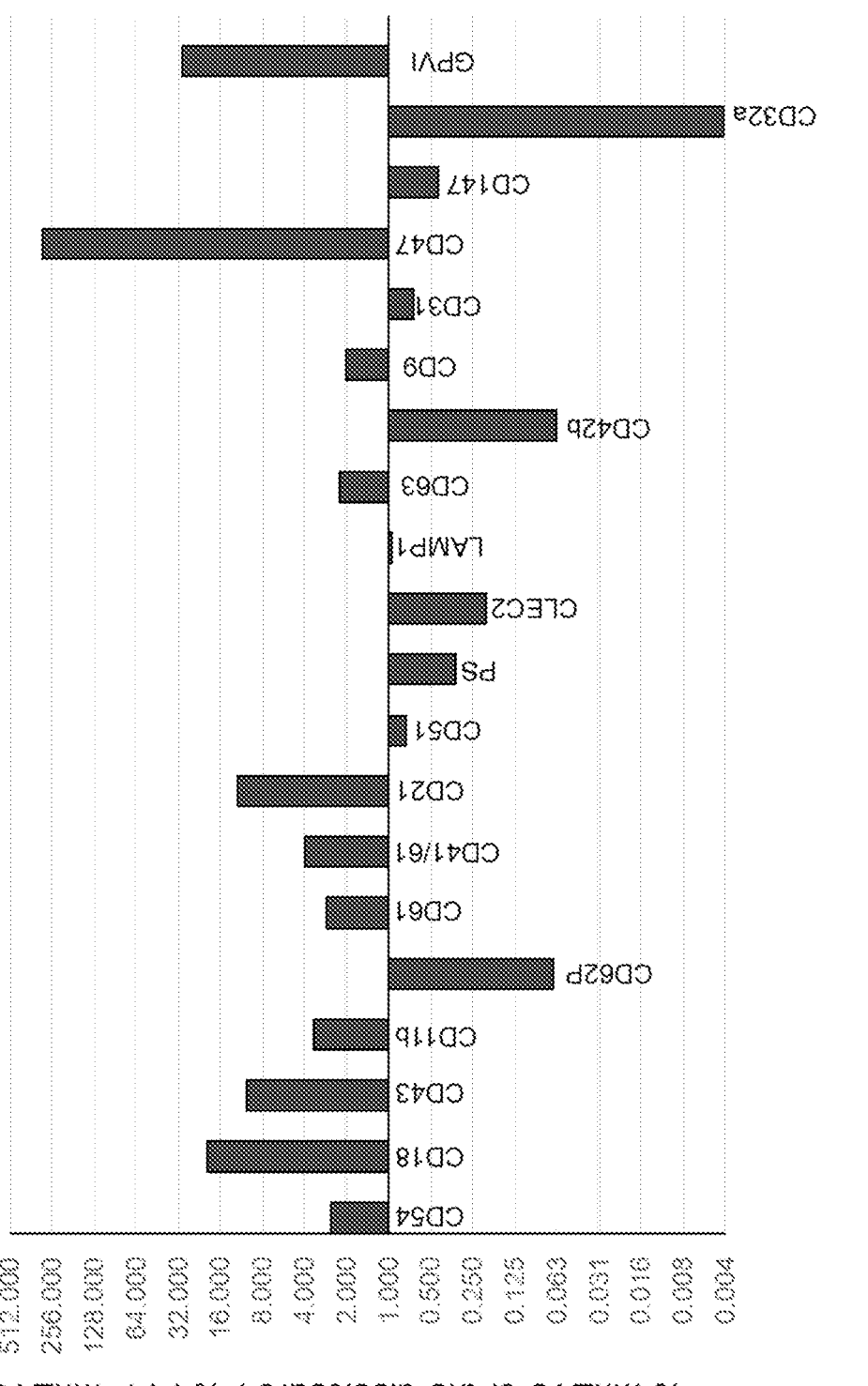
Figure 2E:
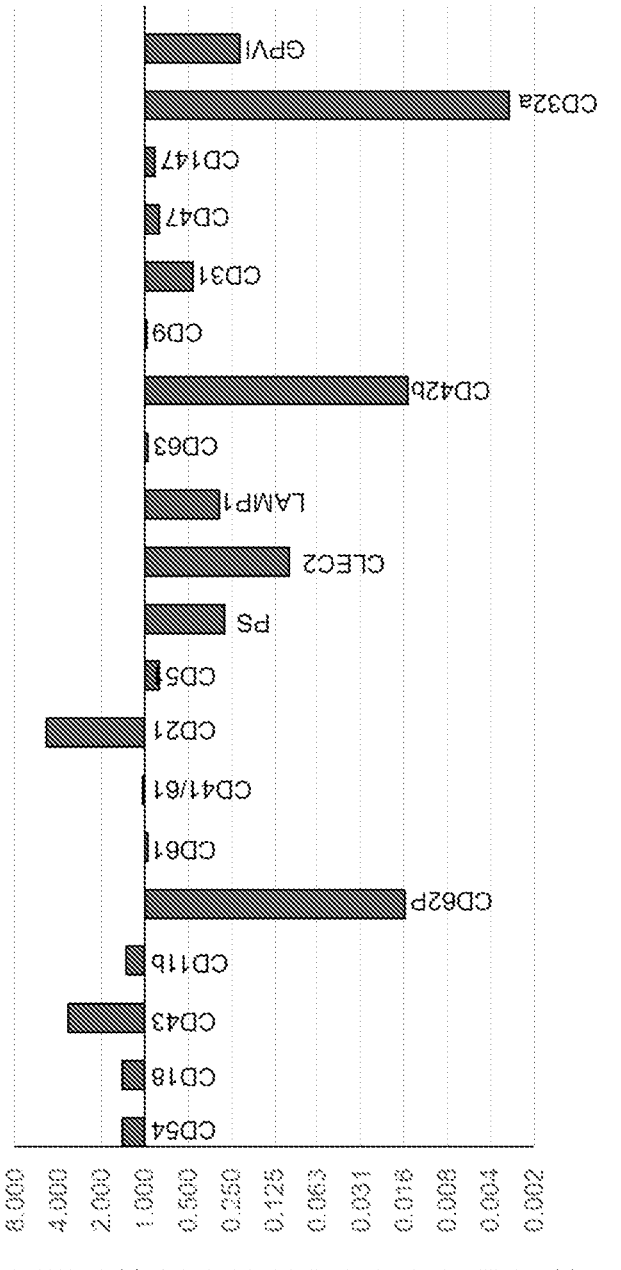
Figure 2F:
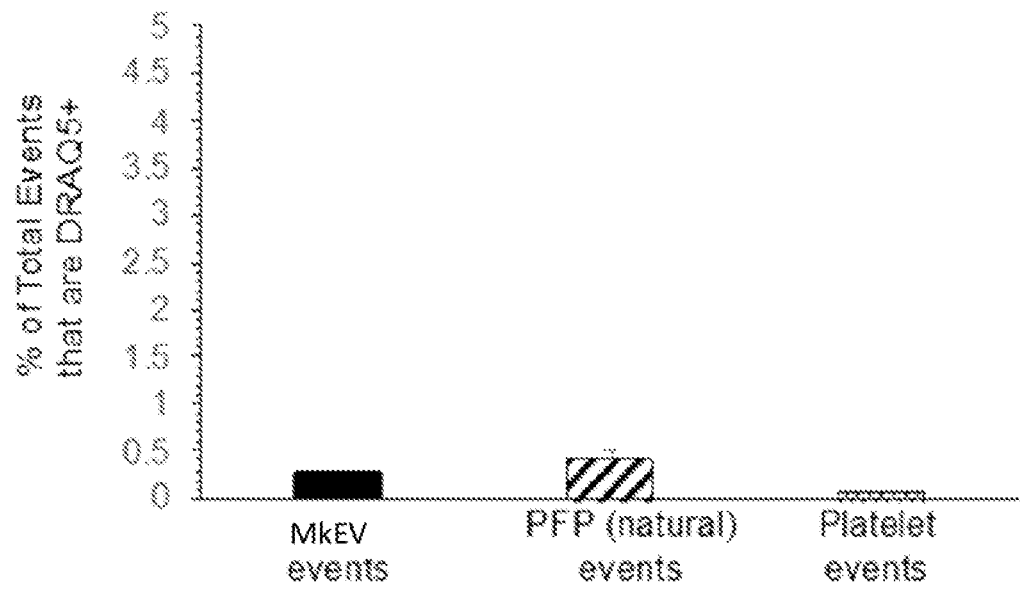

4 let-derived EVs (dotted bars). For MKEVs of the disclosure and PFP MkEVs, bars represent average percent±standard deviation, n=2 biologic replicates. Fold change is relative to PFP EVs. FIG. 2D is a representative graph demonstrating the fold change in marker expression between MkEVs of the disclosure and PFP MkEVs. For CD32a, GPVI, and CD18, fold change calculations were made by changing values of 0 to 0.01. FIG. 2E is a representative graph demonstrating the fold change in marker expression between MkEVs of the disclosure and PLT EVs. For CD32a, fold change calculations were made by changing values of 0 to 0.01. The data shows that MkEVs of the disclosure exhibit different expression of surface markers compared to PFP MkEVs and PLT EVs and establish a marker profile of the present MkEVs relative to PFP MkEVs and PLT EVs. FIG. 2F is a representative graph demonstrating the minimal presence of DRAQ5 positive events showing the lack of cellular contamination.

Figures 3A, 3B, 3C:
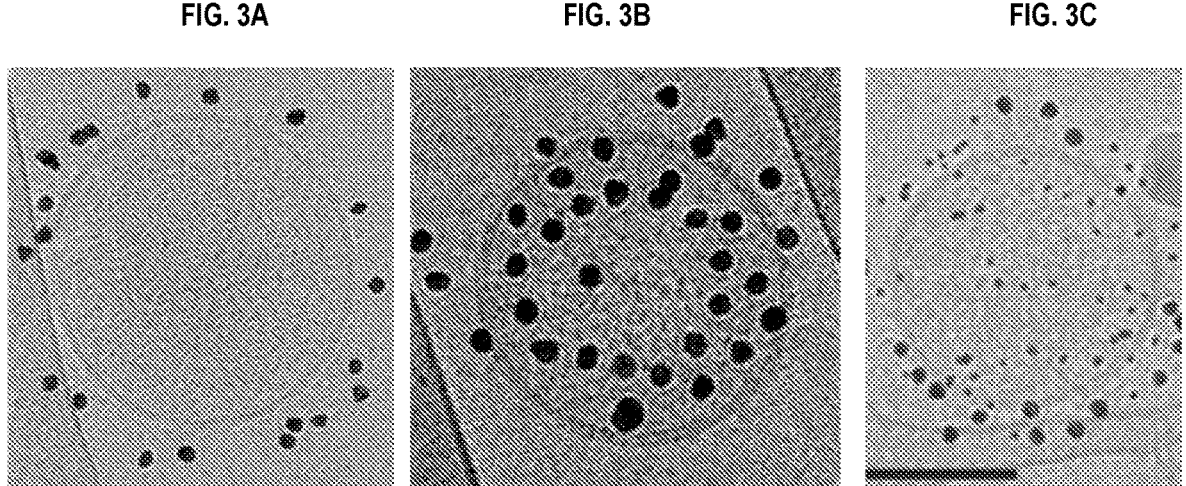

FIGS. 3A-3B are electron microscopic images demonstrating MkEV characterization, including size and morphology. FIG. 3A is a cryo-EM image of MkEVs of the disclosure with immunogold labeling of CD41. FIG. 3B is a cryo-EM image of MkEVs of the disclosure with immunogold labeling of phosphatidylserine. Measuring of MkEVs in cryo-EM images showed a range of MkEV sizes between 100-500 nm, averaging ~250 nm in diameter. FIG. 3C is an image of MkEVs isolated from PFP plasma with co-staining of CD41 (large dots) and PS (small dots).

Figure 4A:
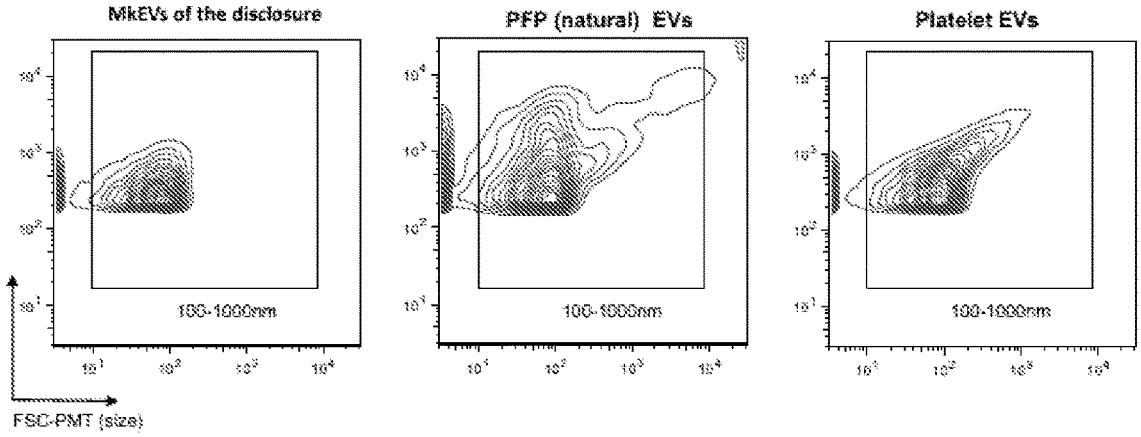
Figure 4B:
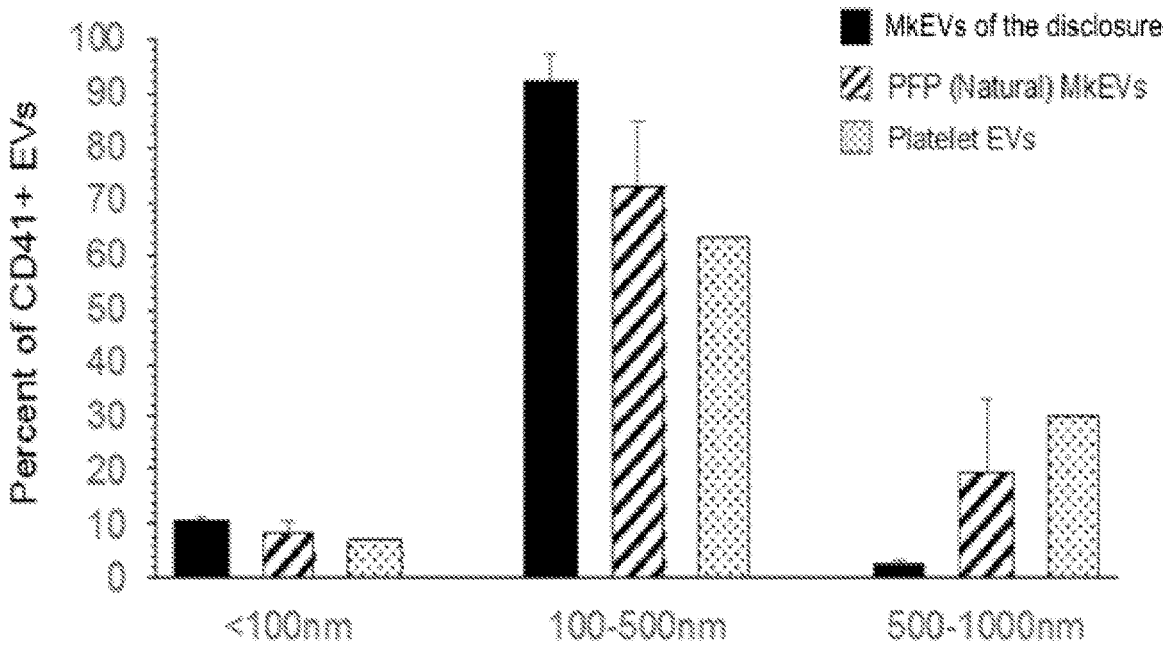
Figure 4C:
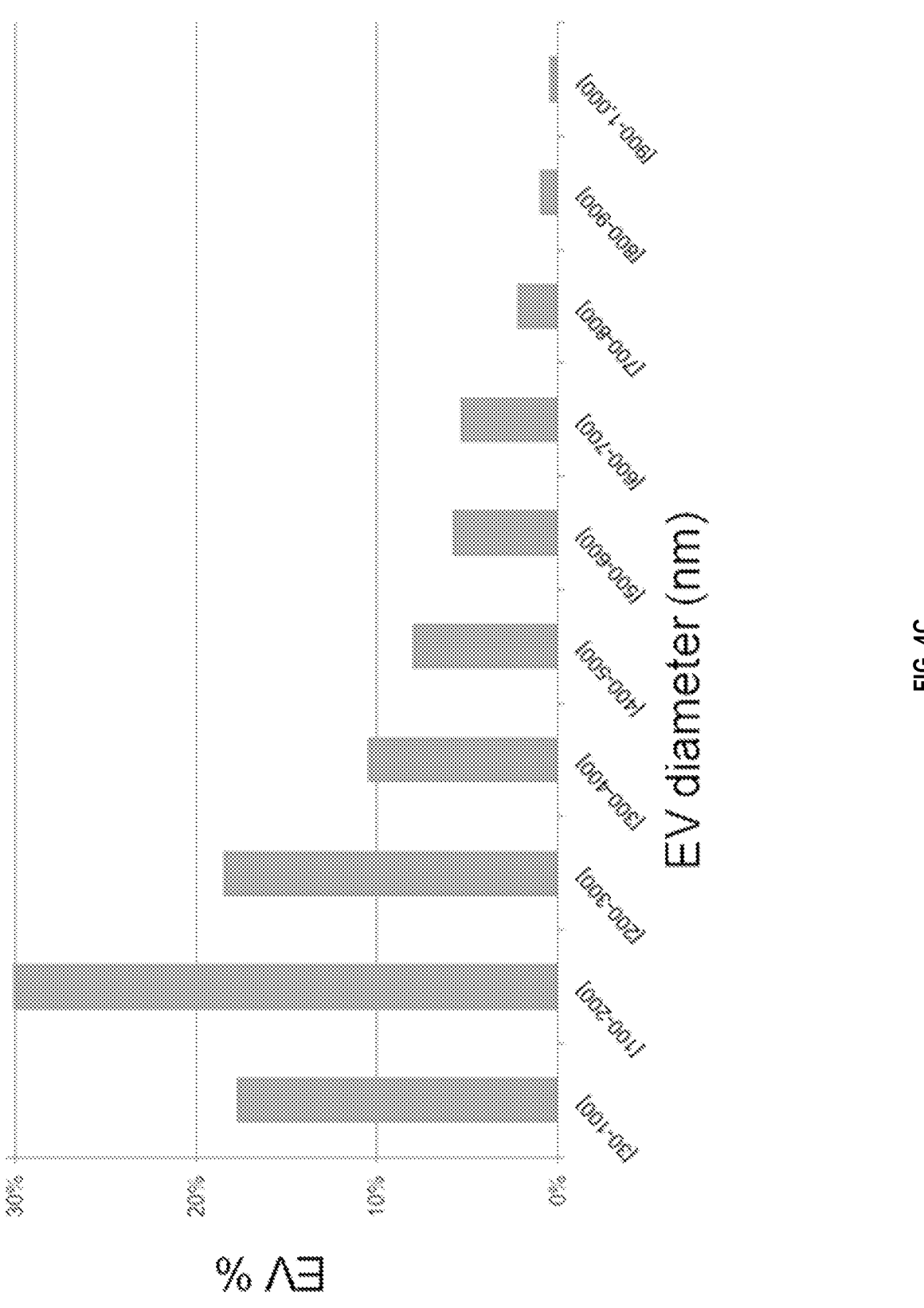
Figures 4F, 4G, 4H, 4I, 4J, 4K:
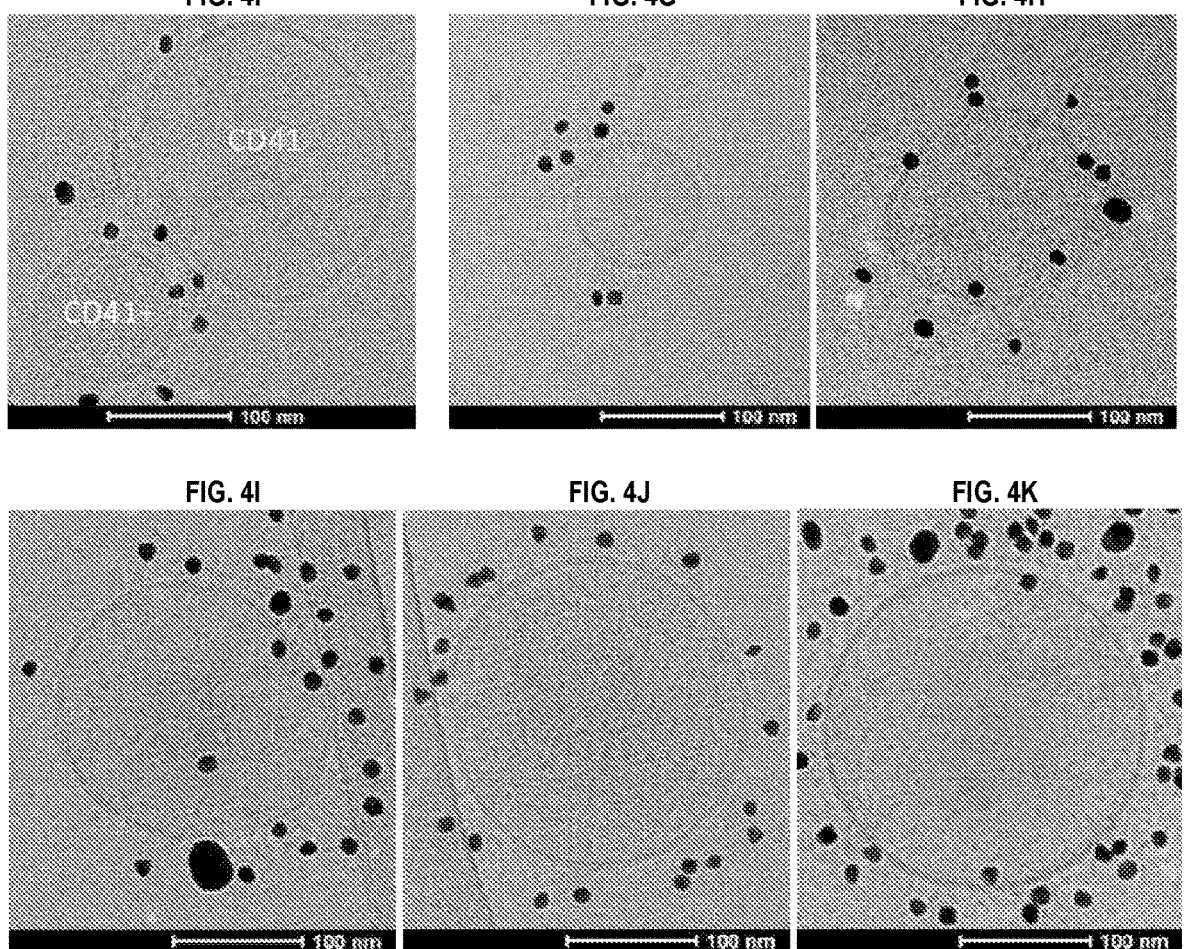

FIG. 4A shows the size distribution (nm) of CD41+ MkEVs of the disclosure compared to CD41+ PFP MkEVs and platelet EVs. Flow cytometric analysis with fluorescent CD41+ antibody labeling was used. FIG. 4B is a graph showing the size distribution of the CD41+ MkEVs of the disclosure compared to CD41+ PFP (Natural MkEVs and platelet CD41+ EVs. FIG. 4C is a graph showing the percent size distribution of the EVs (nm). FIGS. 4D-4E are cryo-EM images of PFP MkEVs. FIGS. 4F-4K are cryo-EM images of MkEVs of the disclosure. Cd41+ Immunogold labeling was used and visible as black dots.

Figure 5A:
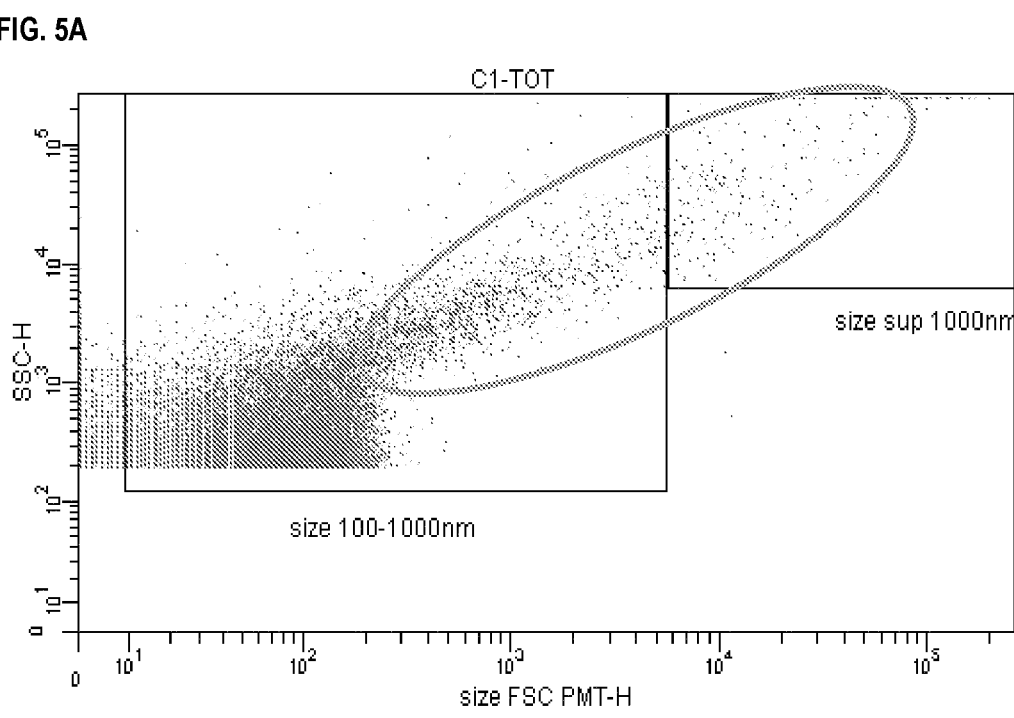
Figure 5B:
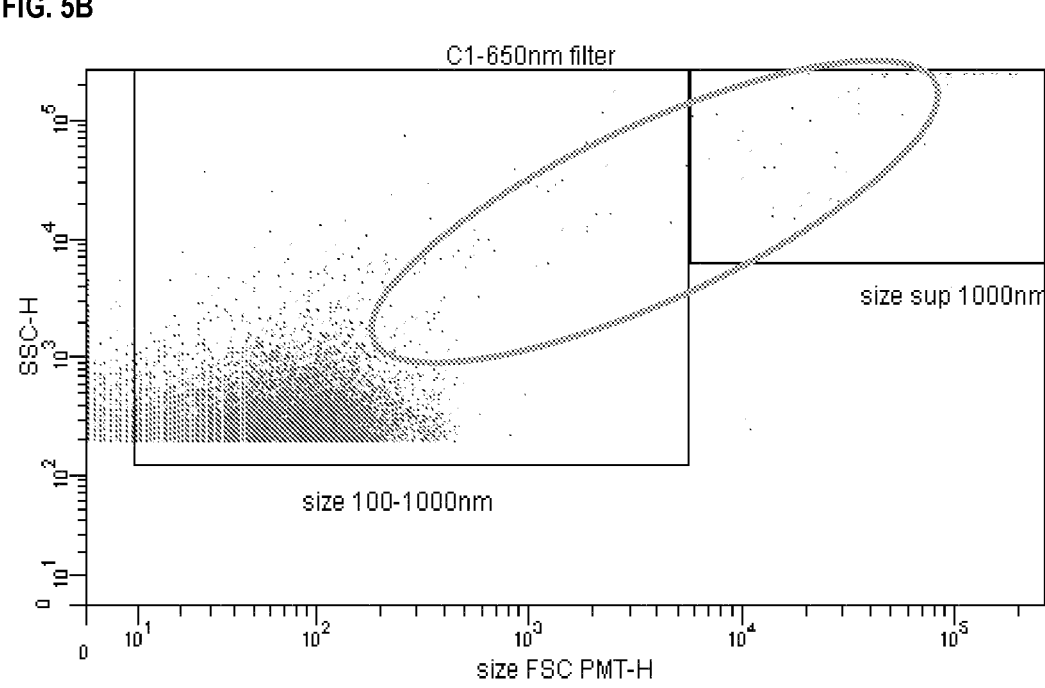

FIGS. 5A-5B are graphs of experimental data showing that size exclusion filtration effectively removes aggregates from unfiltered product. FIG. 5A shows unfiltered MkEV product. FIG. 5B shows 650-nm filtered MkEV product. Successful clearance of large aggregate material (observed by EM in frozen MkEV samples) was demonstrated by post-harvest filtration with 650 nm size exclusion filter. Images are from flow cytometry experiments.

FIGS. 6A-6H are graphs of experimental data showing EV characterization. EVs were collected from media containing mature, cultured MKs 24 hours after megakaryocyte isolation and purification. Isolated human platelets were stimulated with either thrombin (0.1 U/mL) and collagen (1 μg/mL) (traditional platelet agonists) or LPS (5 μg/mL). EV number/platelet and size were measured via nanoparticle tracking analysis (FIGS. 6A, 6B, 6E, and 6F) and CD41 receptor positivity and amount by electron microscopy (FIGS. 6C, 6D, 6G, and 6H).

Figure 7A:
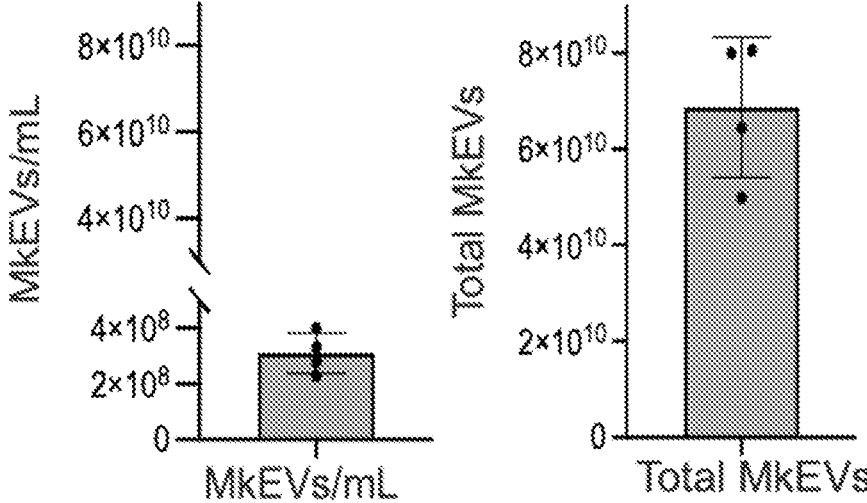
Figure 7B:
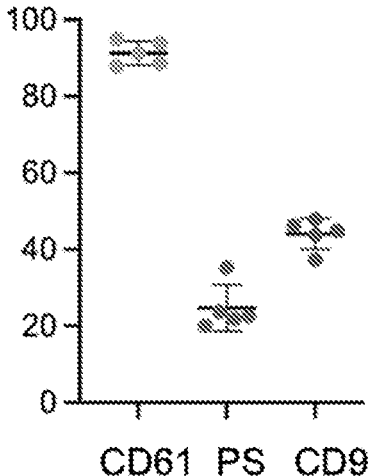

FIGS. 7A-7B show minimal inter-batch variability in MkEV yield as indicated by average MkEVS/mL (FIG. 7A, left) and total MkEV yield (FIG. 7A, right). In addition, MkEV surface marker expression was similar between batches (FIG. 7B)

Figure 8A:
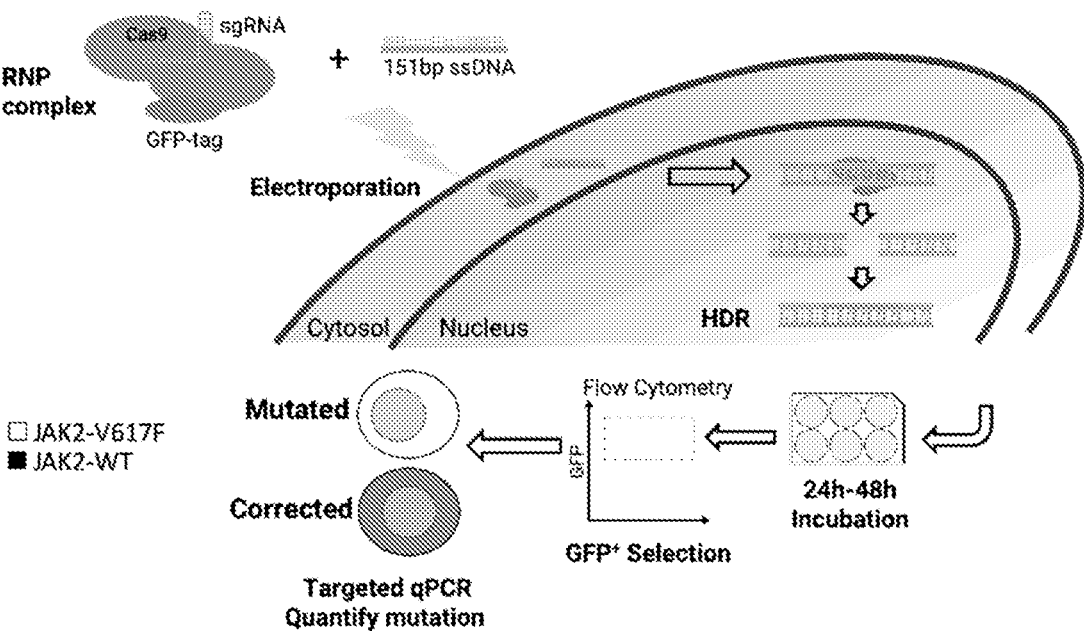
Figure 8B:
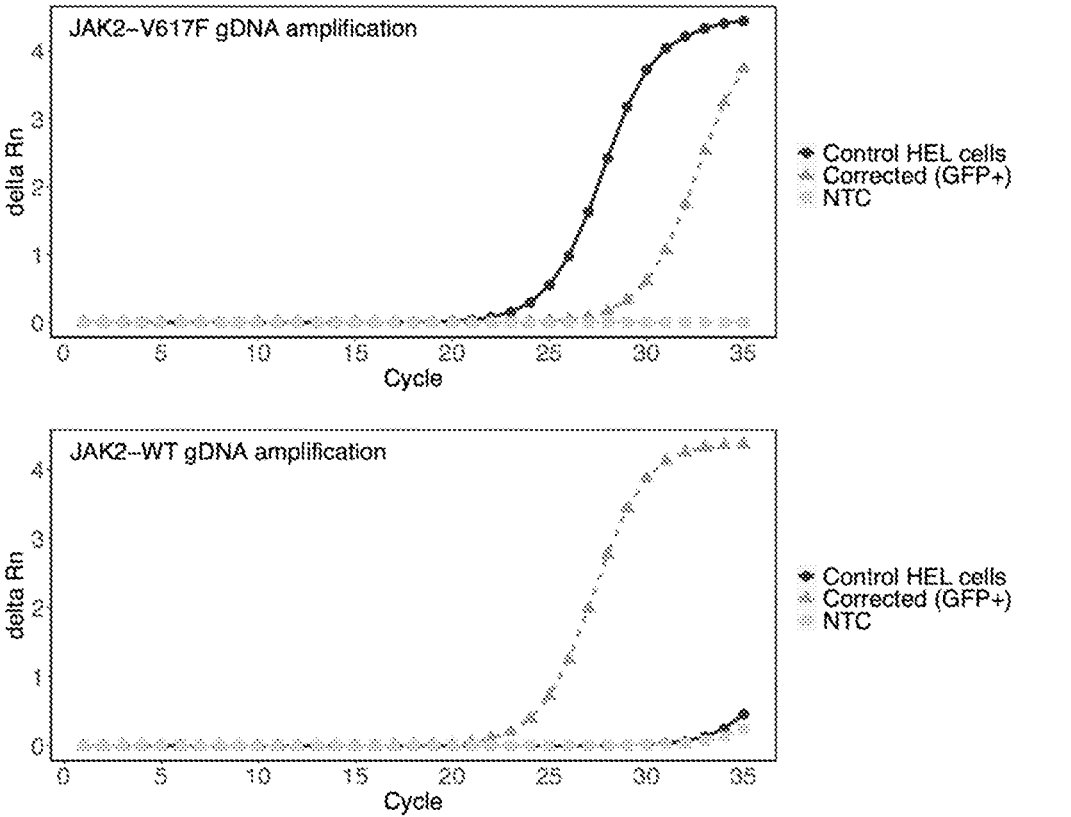

FIG. 8A-8B show successful editing of the JAK2-V617F mutation in vitro. Gene editing constructs were designed and a method for correcting the JAK2 V617F mutation by homologous recombination was developed (FIG. 8A). As shown in FIG. 8A, HEL cells, leukemic cell line carrying the JAK2-V617F mutation, were electroporated with a GFP-tagged ribonucleoprotein (RNP) and a single stranded oligonucleotide template for homologous recombination. GFP+ cells were isolated 24 hours later, and successful editing of the JAK2-V617F mutation was demonstrated by qPCR of genomic DNA (FIG. 8B).

Figure 9A:
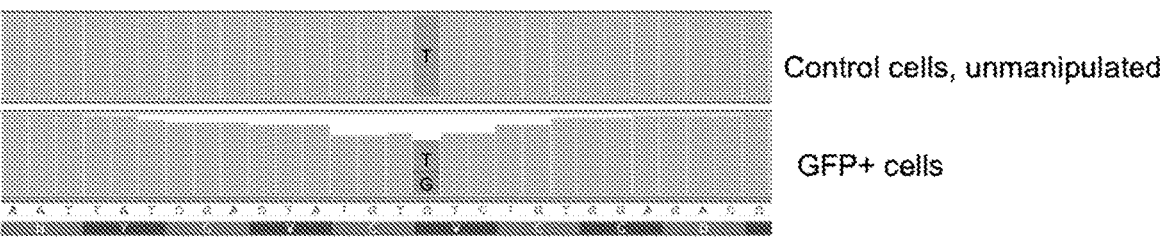
Figure 9B:
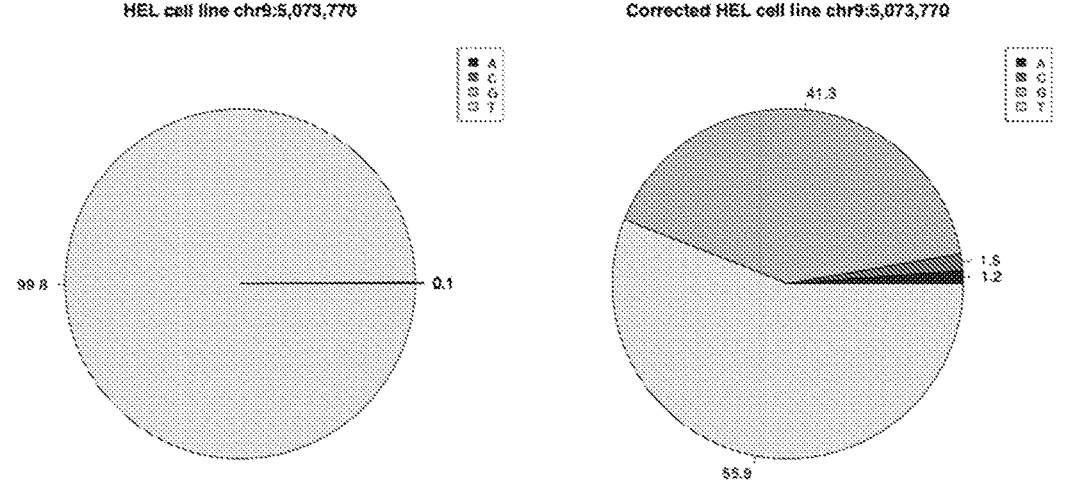
Figure 9C:
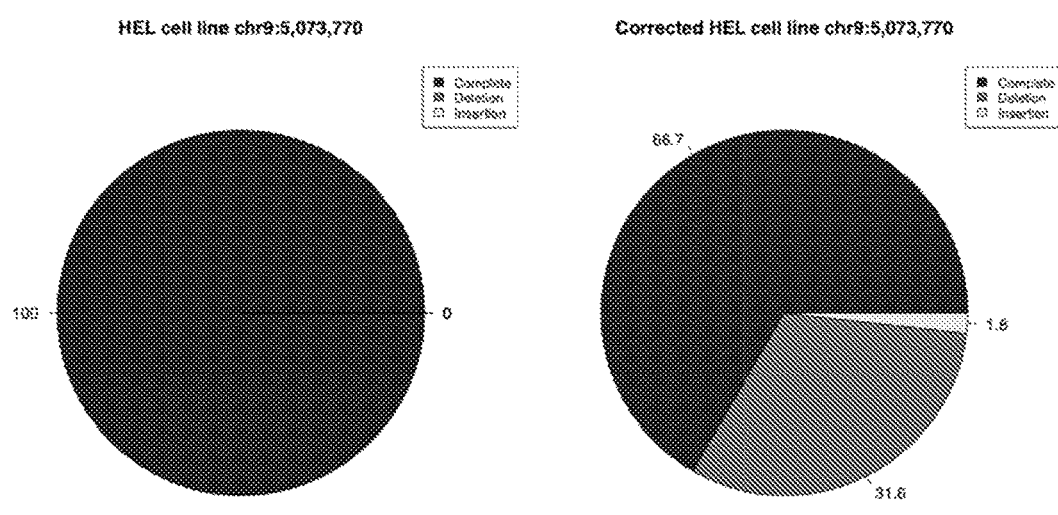

FIGS. 9A-9C show correction of the JAK2-V617F mutation in edited cells as demonstrated by next generation sequencing (NGS) of control and edited HEL cells. NGS showed 41% correction efficiency in edited cells (FIG. 9A) with base proportions of uncorrected and RNP-transfected HEL cells and proportions of insertions and deletions in uncorrected and RNP-transfected HEL cells at the V617F point mutation locus shown in FIGS. 9B and 9C, respectively.

Figure 10A:
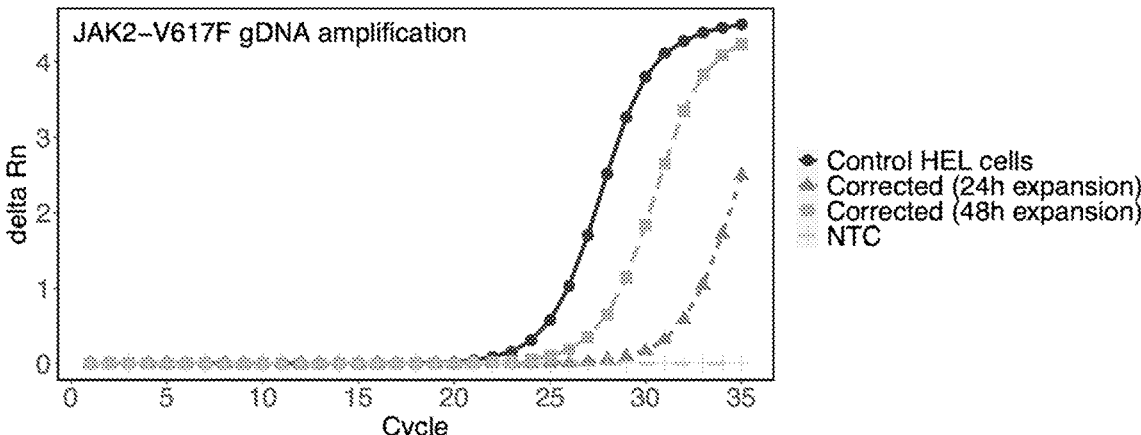
Figure 10B:
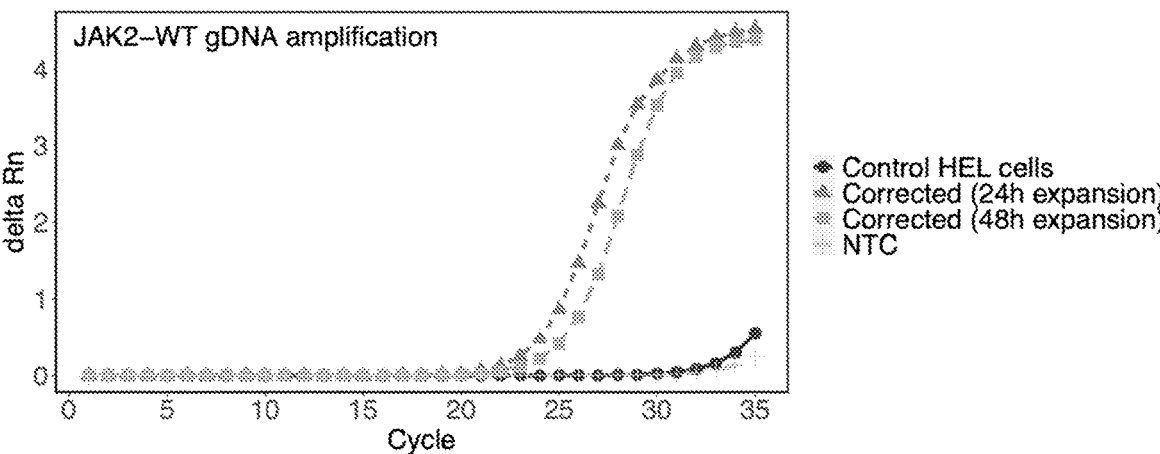

FIGS. 10A-10B show successful correction of the JAK2-V617F mutation by homologous recombination across multiple timepoints. GFP-tagged RNP targeting the JAK2 mutation was electroporated into HEL cells. GFP+ cells were sorted 24- and 48-hours post RNP delivery, and qPCR of genomic DNA was performed for wild type (WT) (FIG. 10B) and mutant JAK2 (FIG. 10A). Cells from both 24 and 48 hours post electroporation demonstrated the presence of WT JAK2 due to gene editing (FIG. 10B).

Figure 11A:
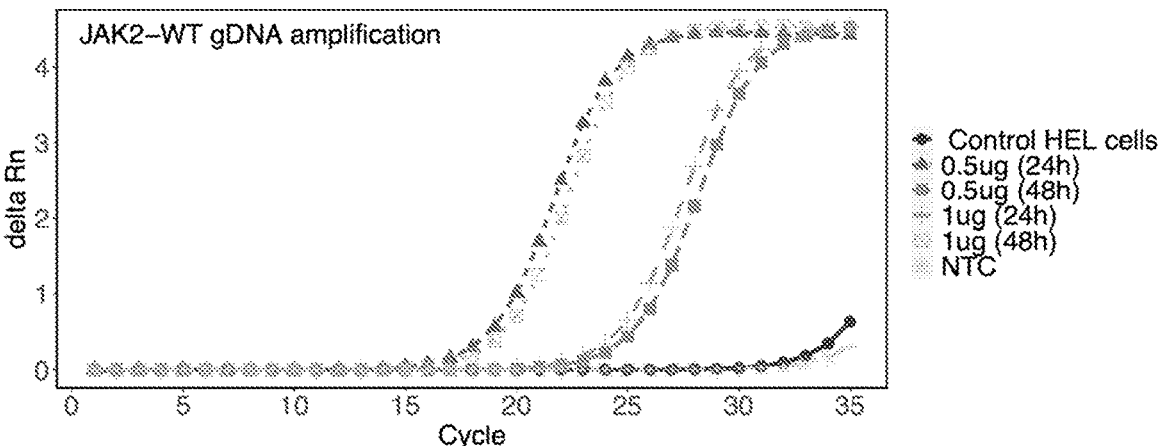
Figure 11B:
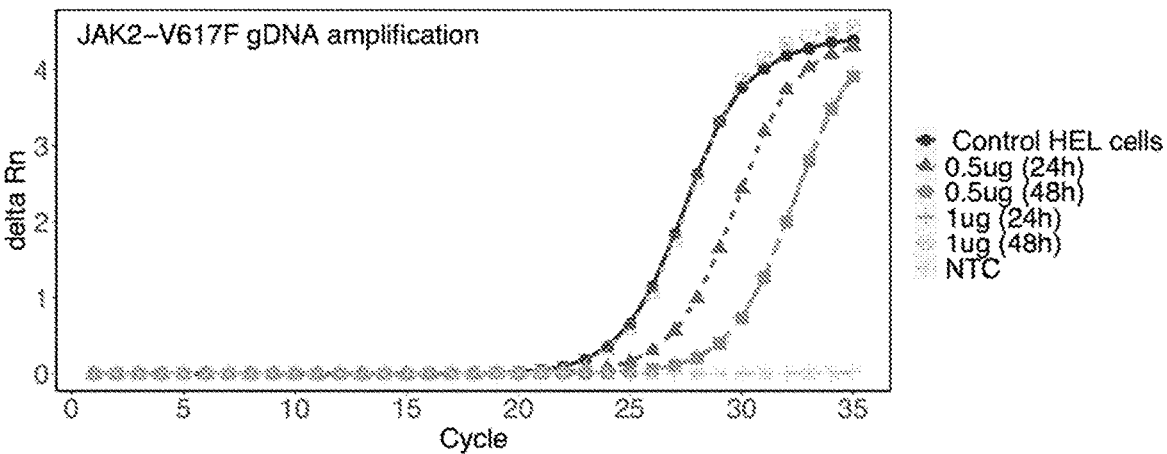

FIGS. 11A-11B show successful correction of the JAK2-V617F mutation by homologous recombination using a pDNA-encoded RNP. pDNA encoding an RNP targeting the JAK2 mutation was electroporated into HEL cells and qPCR on genomic DNA was performed for WT (FIG. 11A) and mutant JAK2 FIG. 11B). Cells at 24- and 48-hours post electroporation demonstrated the presence of WT JAK2 due to gene editing (FIG. 11A).

Figure 12A:
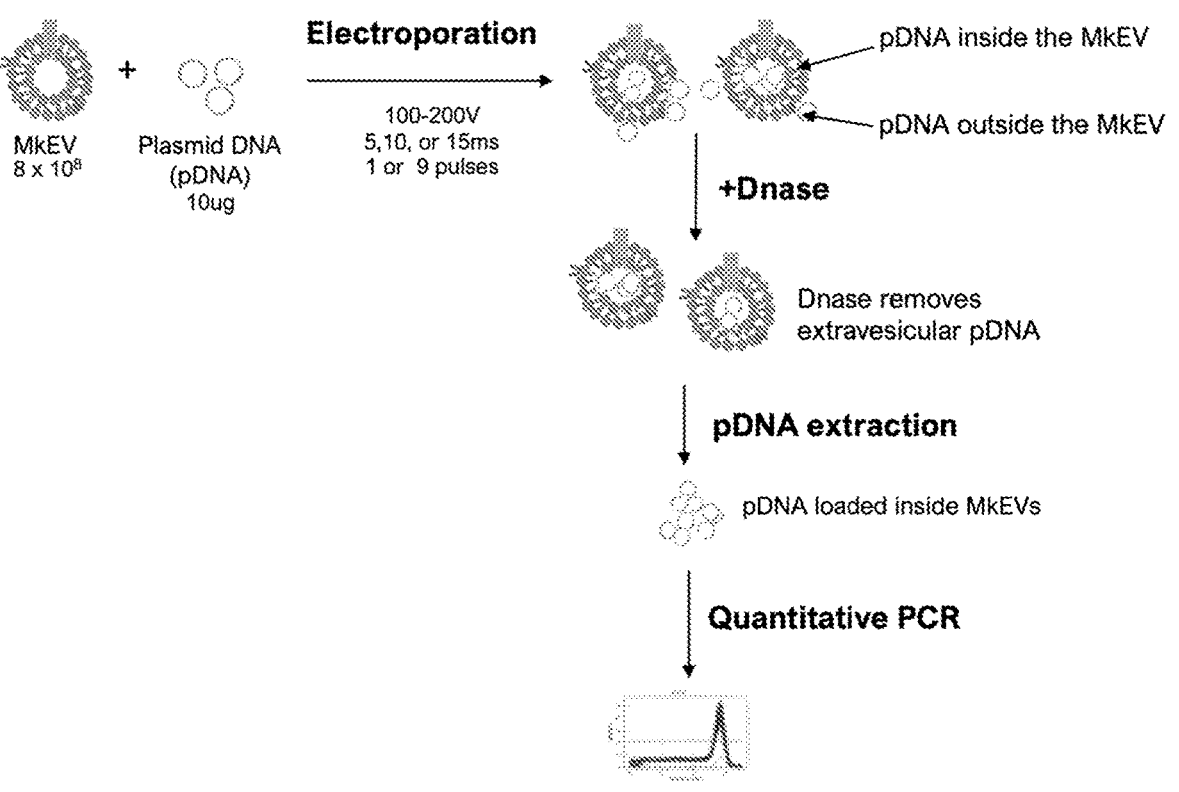
Figure 12B:
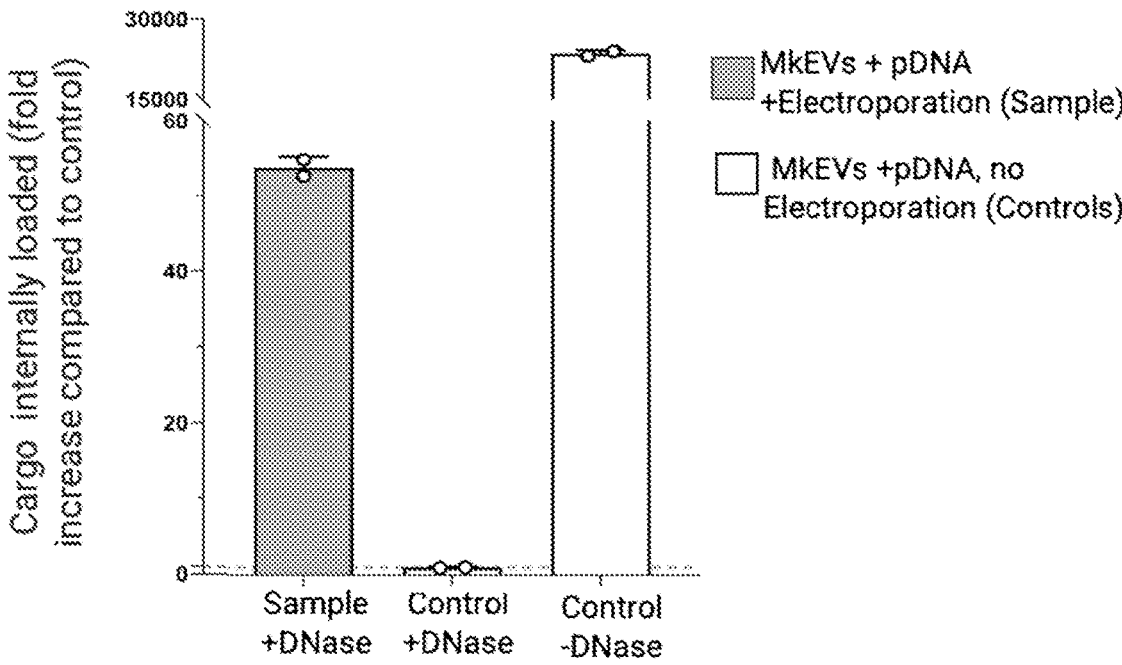

FIGS. 12A-12B demonstrate nucleic acid cargo loading into MkEVs by electroporation. For these experiments, pDNA encoding an MPN gene editor was electroporated into MkEVs using the 4D-Nucleofector (Lonza Wakersville, Inc.). pDNA was extracted following DNase 1 treatment to remove non-internalized DNA, and quantified by qPCR. Controls included MkEVs+ pDNA without electroporation±DNase treatment (FIG. 12A). As demonstrated by the bar representing average fold change compared to control samples treated with DNase, pDNA was successfully internalized into MkEVs by electroporation (FIG. 12B).

Figure 13:
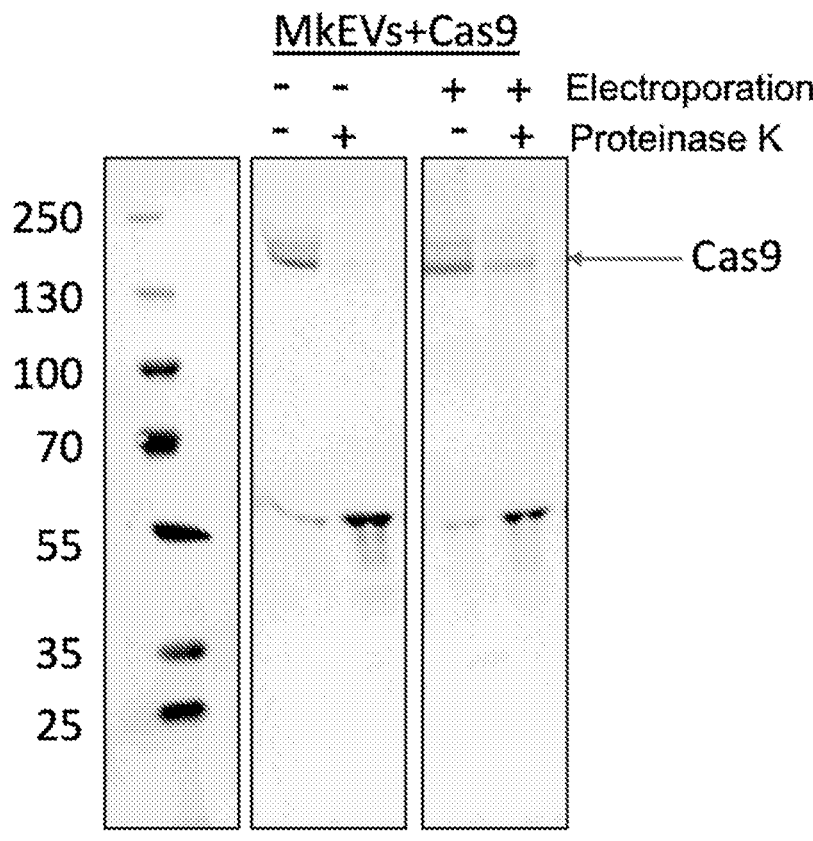

FIG. 13 demonstrates Cas9 protein loading into MkEVs by electroporation. MkEVs were electroporated with Cas9, treated with proteinase K to remove any un-internalized cargo, and then subjected to western blotting for quantification of Cas9. Controls included MkEVs plus Cas9 without electroporation±Proteinase K. Cas9 was present in electroporated MkEVs, but not in control un-electroporated MkEVs, following proteinase K digestion indicating protection by MkEVs of protein cargo following electroporation.

Figure 14A:
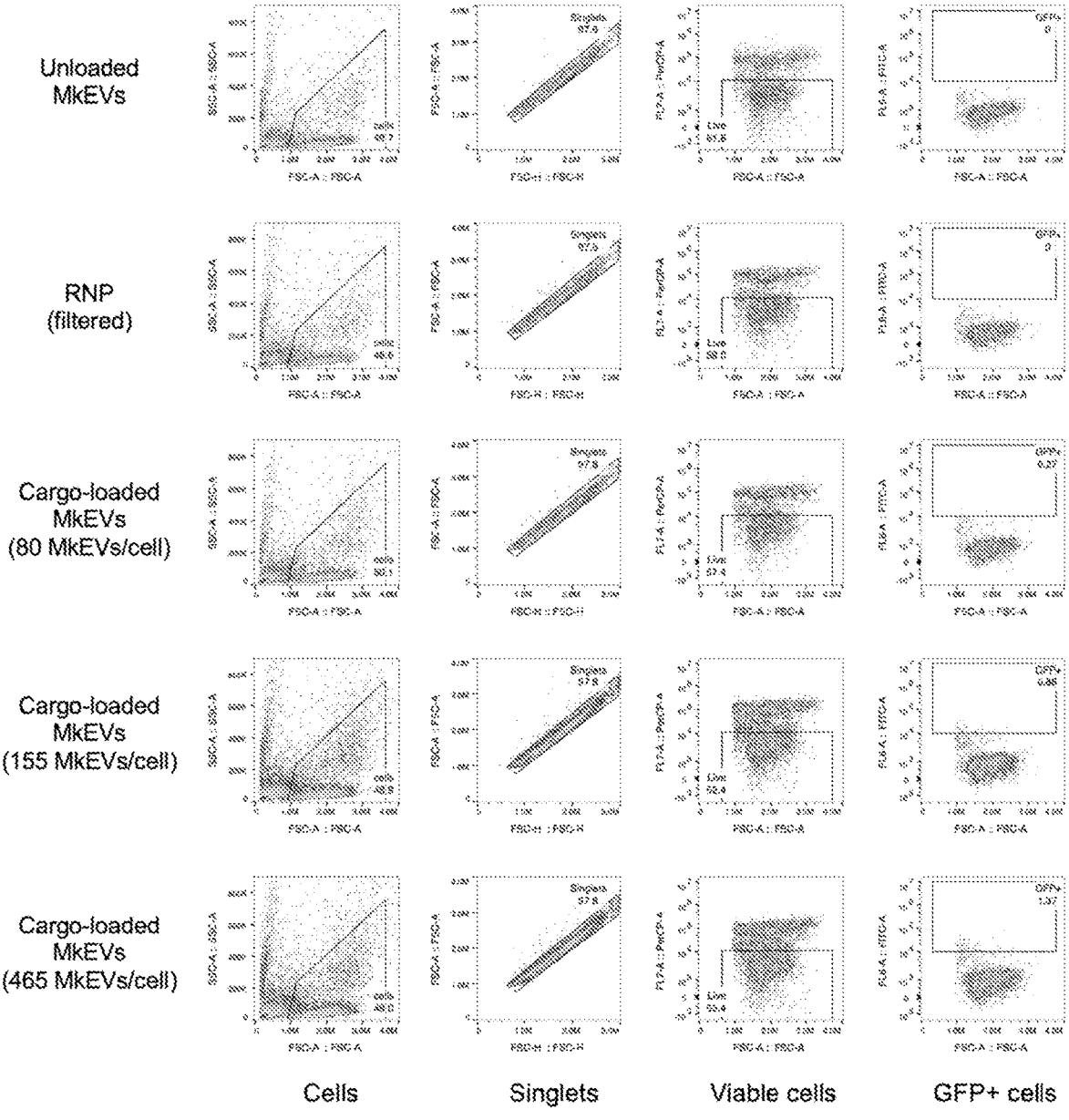
Figure 14B:
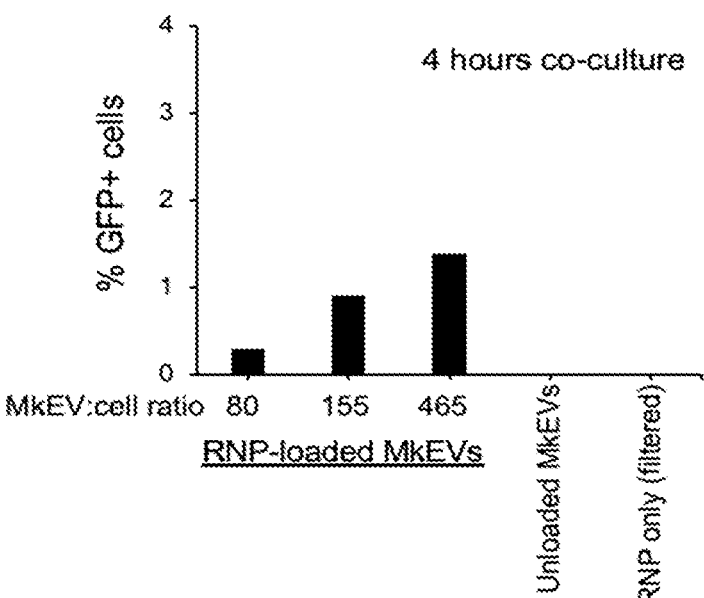
Figure 14C:
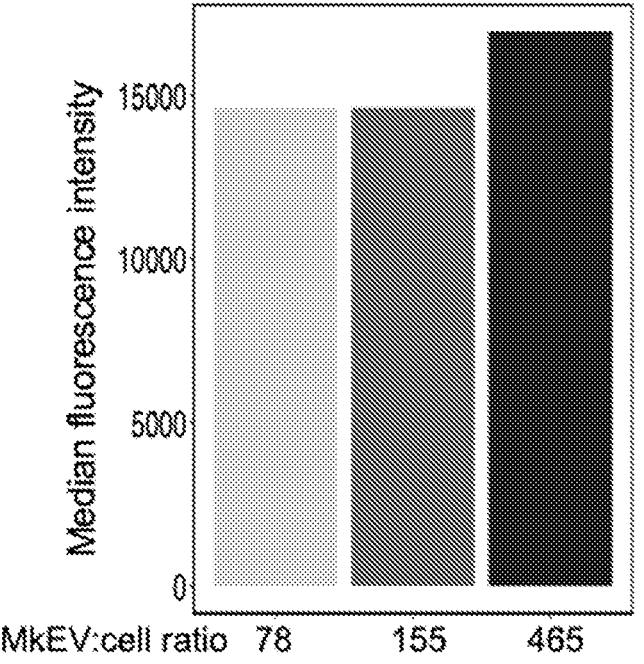

FIGS. 14A-14C show cargo-loaded MkEVs transferred Cas9 to hematopoietic stem and progenitor cells (HSPCs) in vitro. Primary bone marrow derived lineage-depleted cells, isolated from mice carrying the JAK2-V617F mutation, were co-cultured with MkEVs loaded with GFP-tagged Cas9 RNP (ribonucleoprotein) for 4 hours in vitro. Doses were 80, 155, and 465 MkEVs/cell. Controls included cells co-cultured with unloaded MkEVs and cells co-cultured with RNP alone, processed in parallel to MkEVs. The percentage of GFP+ cells, were quantified by flow cytometry (FIG. 14A). The percent of GFP+ cells increased with increasing MkEV dose (FIG. 14B). Median fluorescence intensity is shown in FIG. 14C.

Figure 15A:
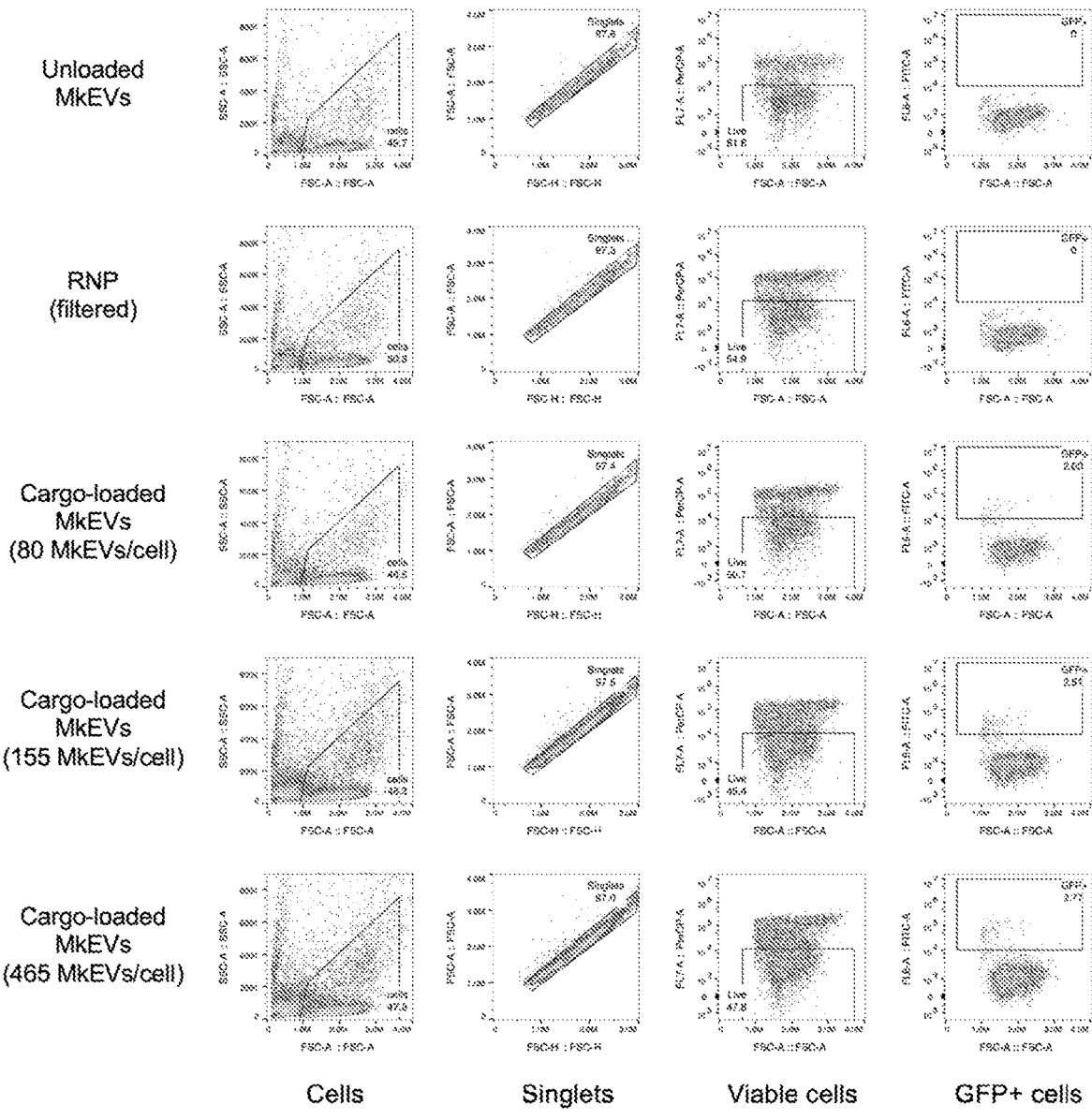
Figure 15B:
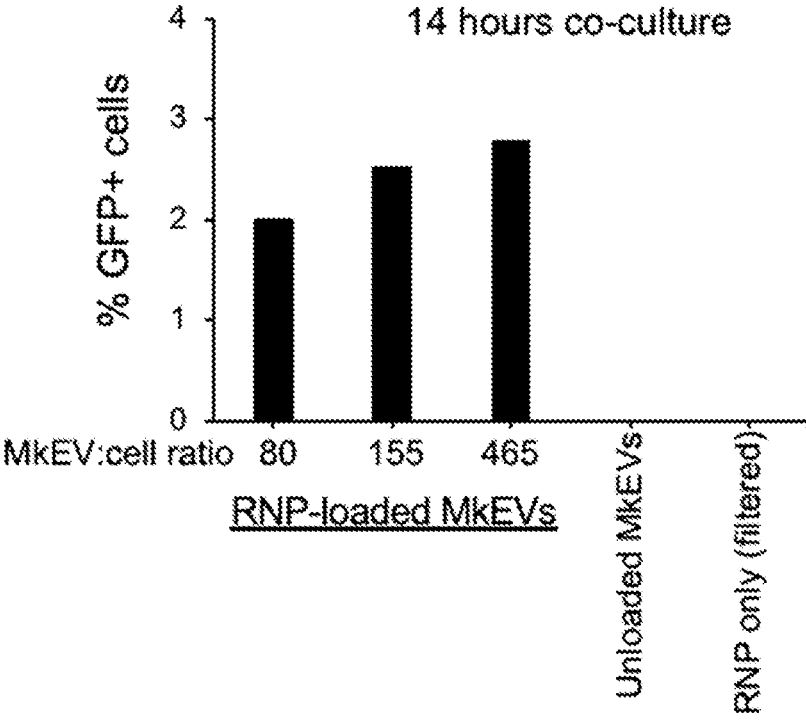
Figure 15C:
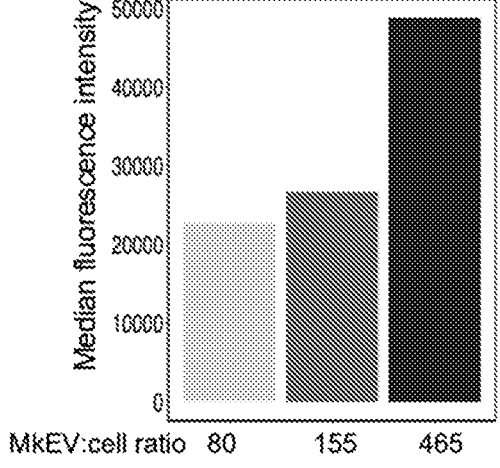

FIGS. 15A-15C show increased association and/or uptake of cargo-loaded MkEVs by hematopoietic stem and progenitor cells (HSPCs) following longer co-culture time in vitro. Primary bone marrow derived lineage-depleted cells, isolated from mice carrying the JAK2-V617F mutation, were co-cultured with MkEVs loaded with GFP-tagged Cas9 RNP for 14 hours in vitro. Doses were 80, 155, and 465 MkEVs/cell. Controls included cells co-cultured with unloaded MkEVs and cells co-cultured with RNP alone, processed in parallel to MkEVs. GFP+ cells were quantified by flow cytometry (FIG. 15A). The percent GFP+ cells increased with increased MkEV dose and the median mean fluorescence intensity increased with the increased dose and time of co-culture (FIGS. 15B and 15C).

Figure 16A:
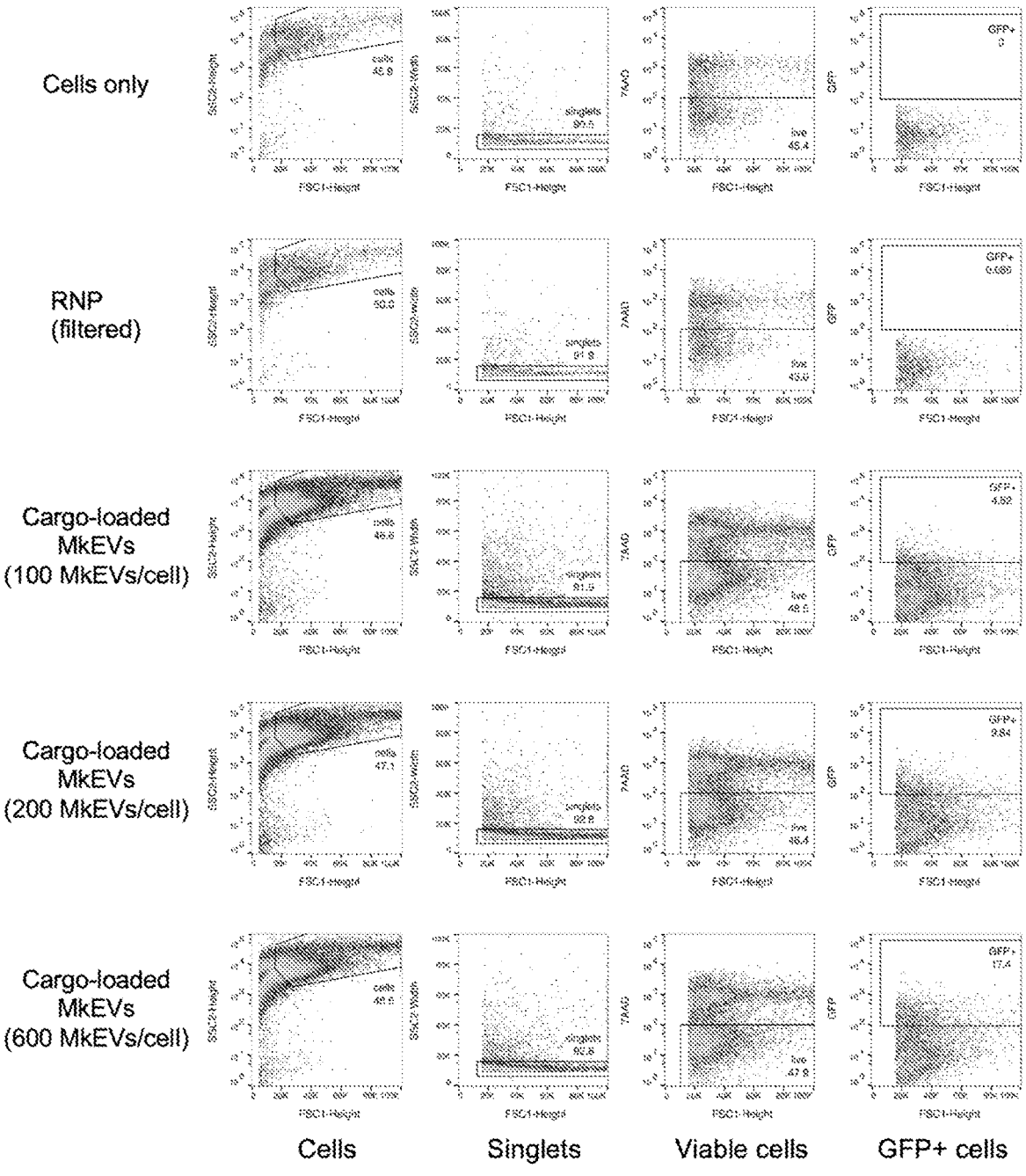
Figure 16B:
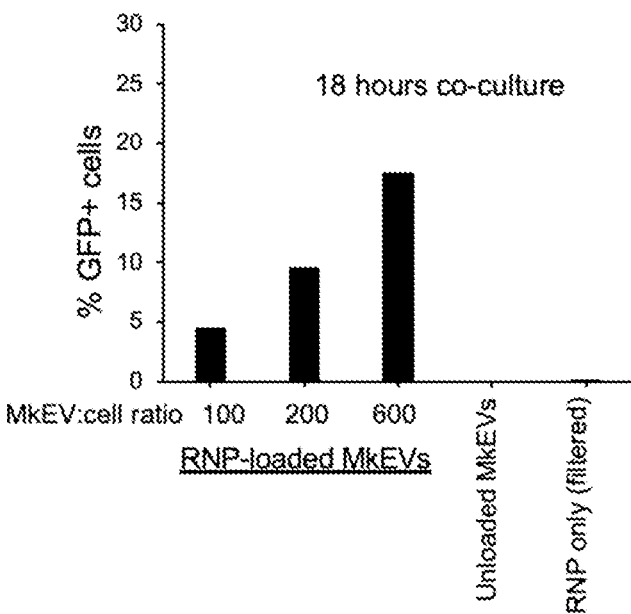
Figure 16C:
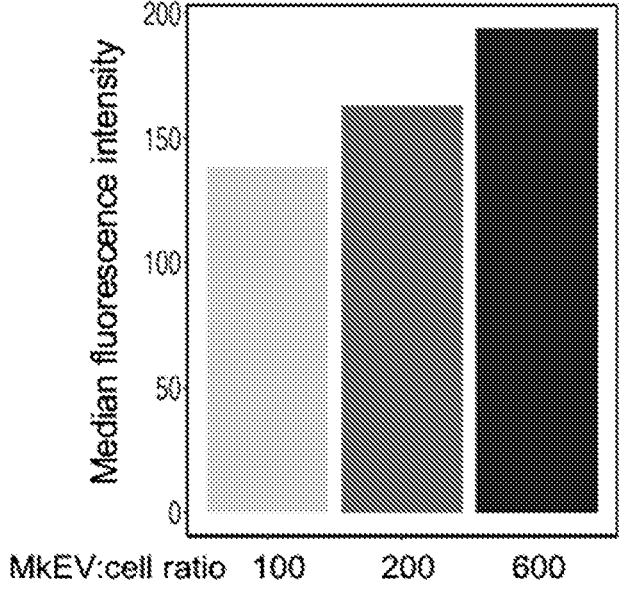

FIGS. 16A-16C show significant association and/or uptake of cargo-loaded MkEVs by primary murine bone marrow lineage depleted cells following 18 hours in co-culture. Primary bone marrow derived lineage-depleted cells, isolated from mice carrying the JAK2-V617F mutation, were co-cultured with MkEVs loaded with GFP-tagged Cas9 RNP for 18 hours in vitro. Doses were 80, 155, and 465 MkEVs/cell. Controls included cells alone and cells co-cultured with RNP alone, processed in parallel to MkEVs. GFP+ cells were quantified by flow cytometry (FIG. 16A). The percent GFP+ cells increased with increased MkEV dose, with 17% of cells positive for MkEV association at the 450 MkEV/cell dose (FIGS. 16A and 16B).

Figure 17A:
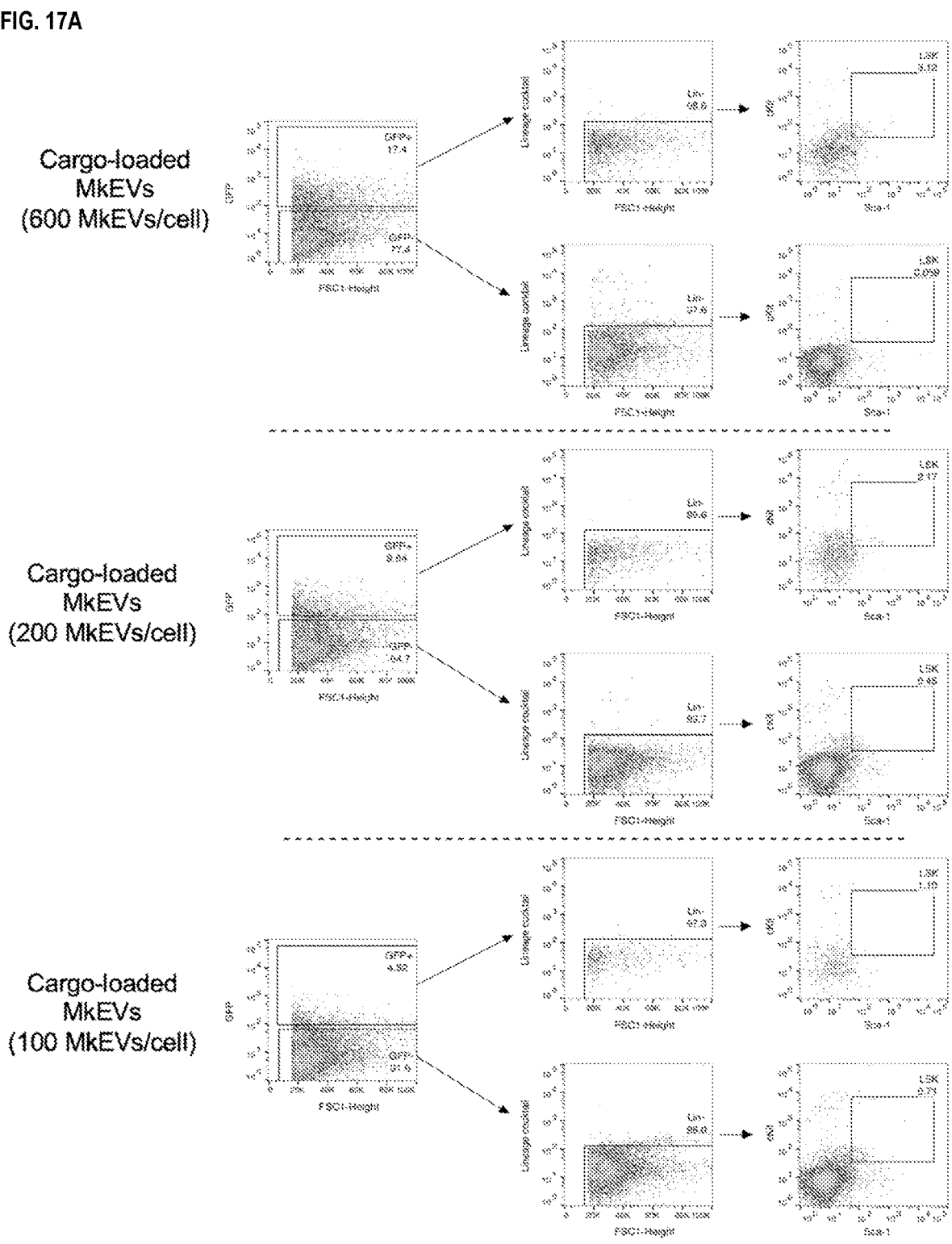
Figure 17B:
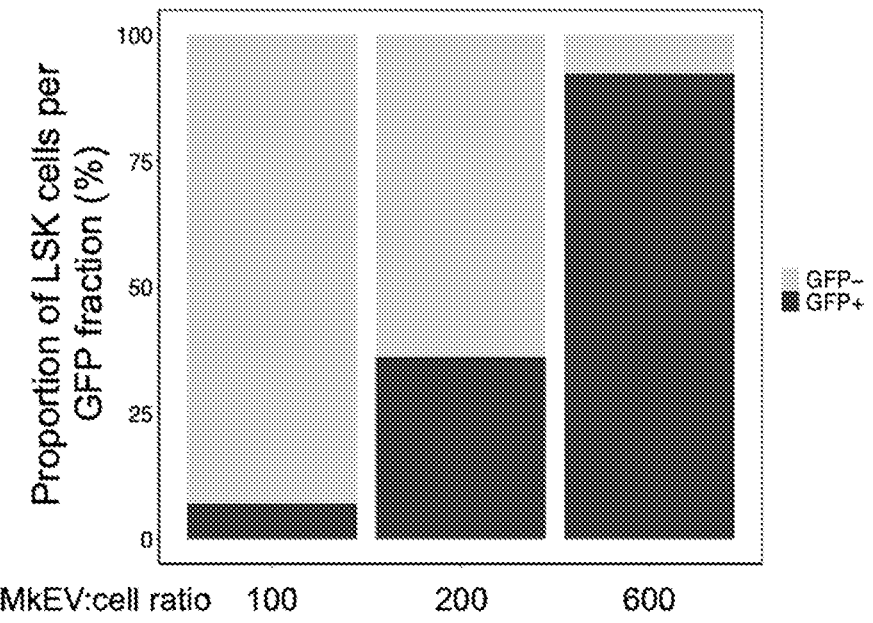
Figure 17C:
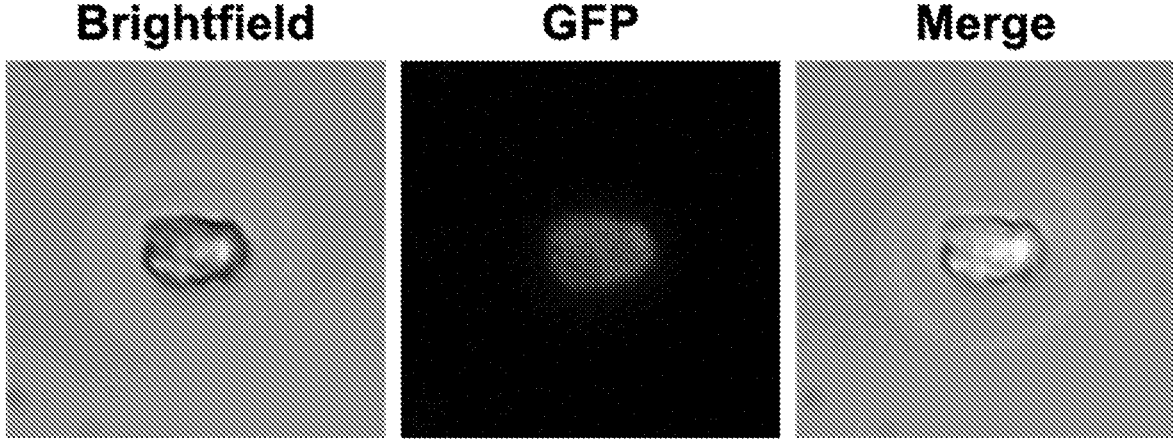

FIGS. 17A-17C show that MkEVs preferentially target primitive HSPCs. Lineage-depleted co-cultured with RNP-loaded MkEVs for 18 h were stained for HSPC-specific markers (c-Kit and Sca-1) to determine the phenotype of cells targeted by MkEVs. Flow analysis of Lineage negative/c-Kit+/Sca-1+ (LSK) cells, a primitive HSPC population, was performed for GFP+ and GFP– cell fractions (FIG. 17A). An increase in the MkEV:cell ratio was accompanied by an increase in the proportion of LSK cells in the GFP+ fraction (FIG. 17A). A dose of 600 MkEVs/cell was sufficient to target the majority of LSK cells (FIGS. 17A, 17B), These data suggest that MkEVs selectively target the naïve HSPC compartment in vitro. Confocal microscopy of GFP+ cells following co-culture with 600 MkEVs/cell confirmed the MkEV-mediated delivery of the RNP complex to target cells (FIG. 17C). Imaging revealed the internalization of GFP signal in target cells (FIG. 17C).

Figure 18A:
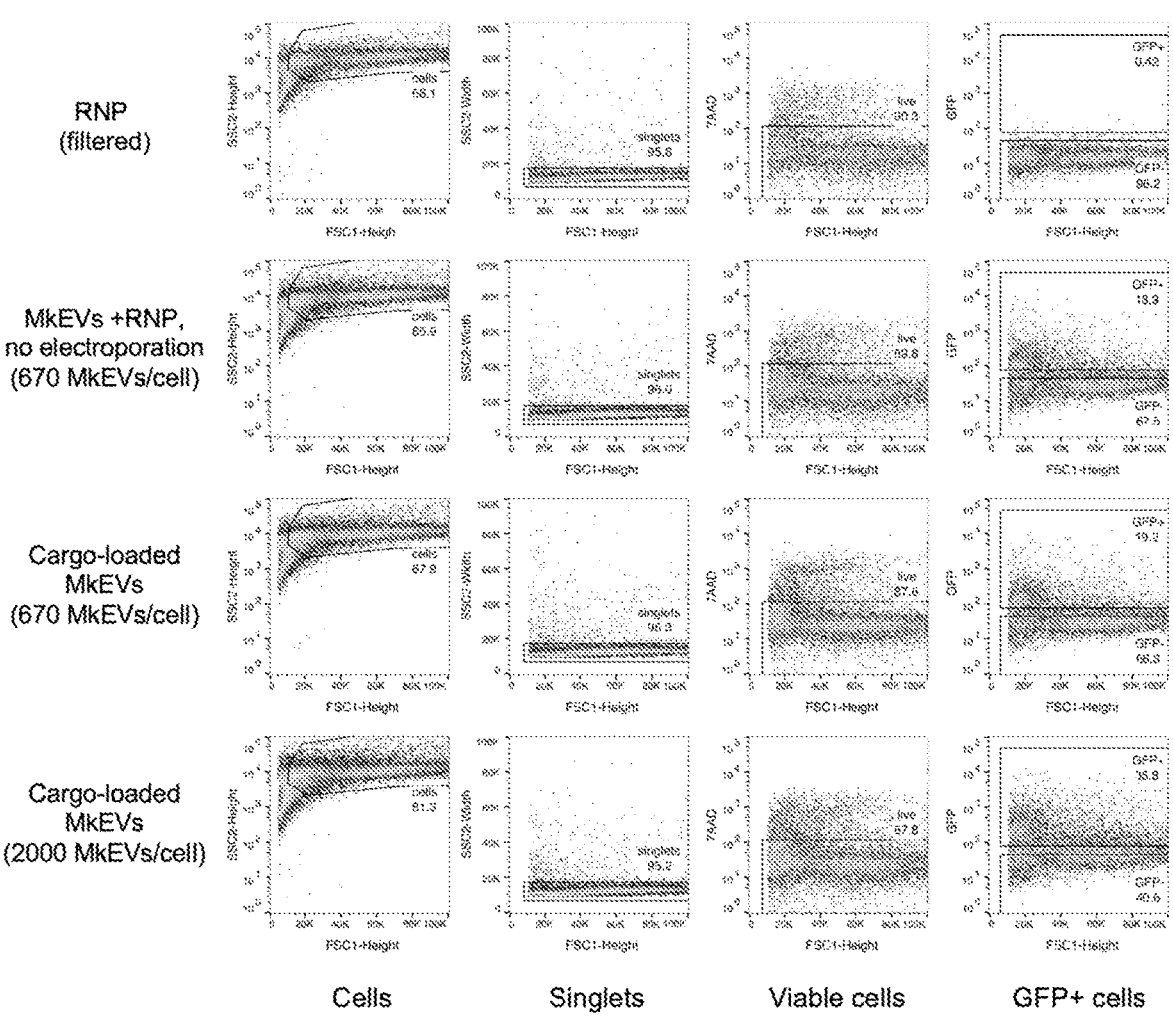
Figure 18B:
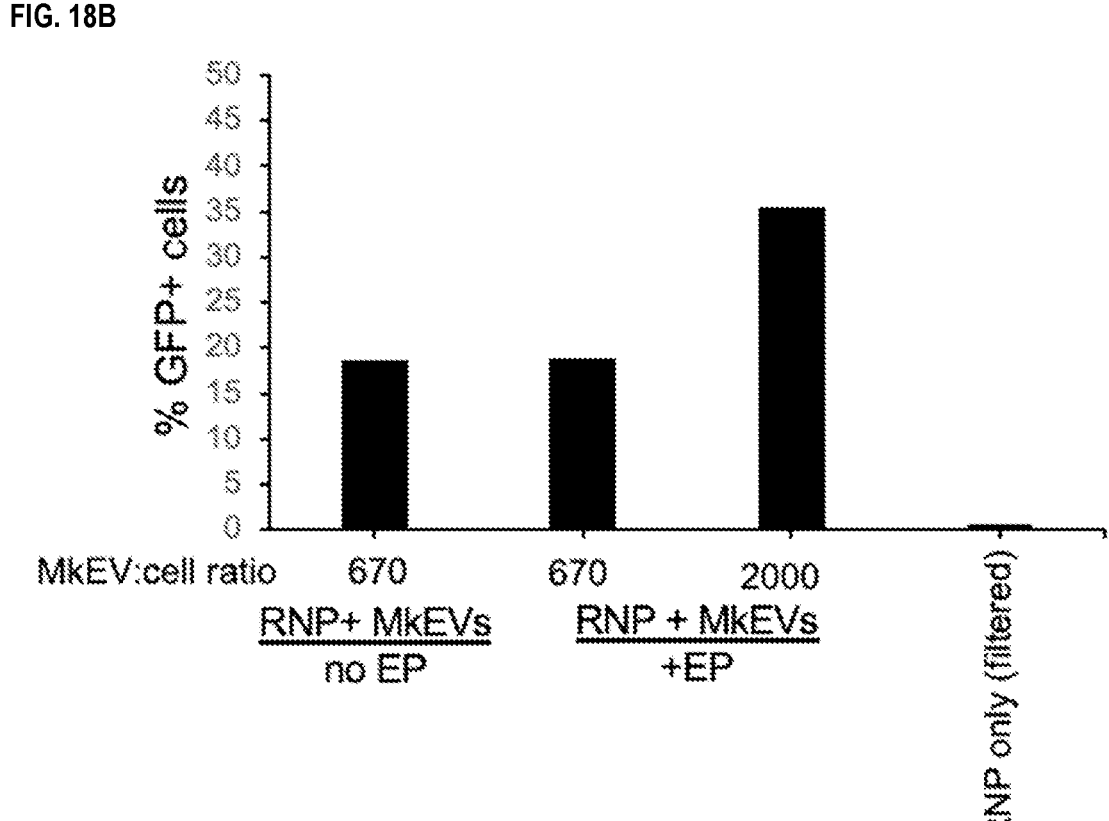

FIGS. 18A-18B shows co-culture of cargo-loaded MkEVs with primary murine Lineage negative/c-Kit+/Sca-1+ (LSK) cells derived from mice homozygous for the JAK2-V617F mutation. MkEVs incubated with GFP-tagged cas9 RNP in the presence or absence of electroporation were co-cultured with LSK cells at doses of 670 and 2000 MkEVs/cells and analyzed for 14 hours. MkEVs facilitated LSK association and uptake of the RNP as evidenced by increased GFP+ cells when incubated with MKEV-RNP (FIG. 18A). There was a dose response with increased percent GFP+ cells with increased MkEV to cell ratios (FIG. 18B).

Figure 19A:
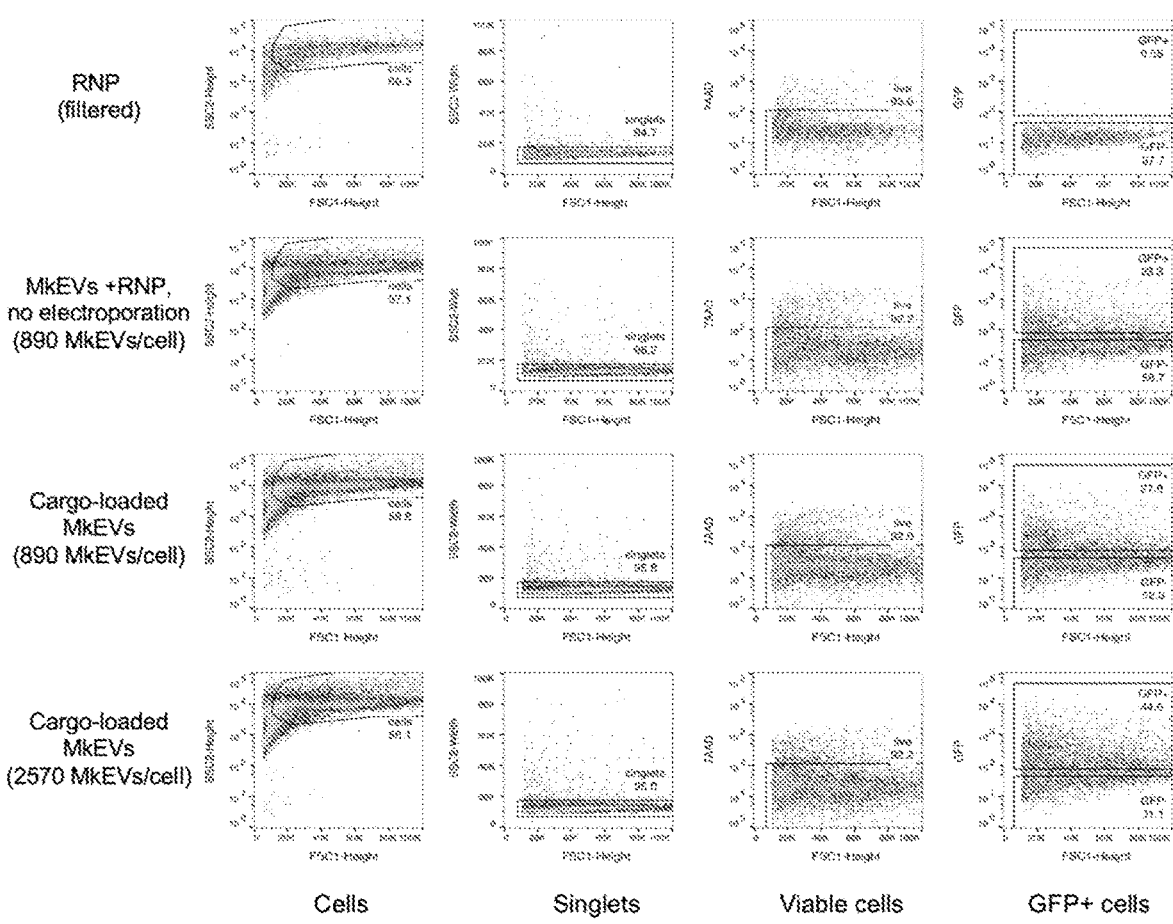
Figure 19B:
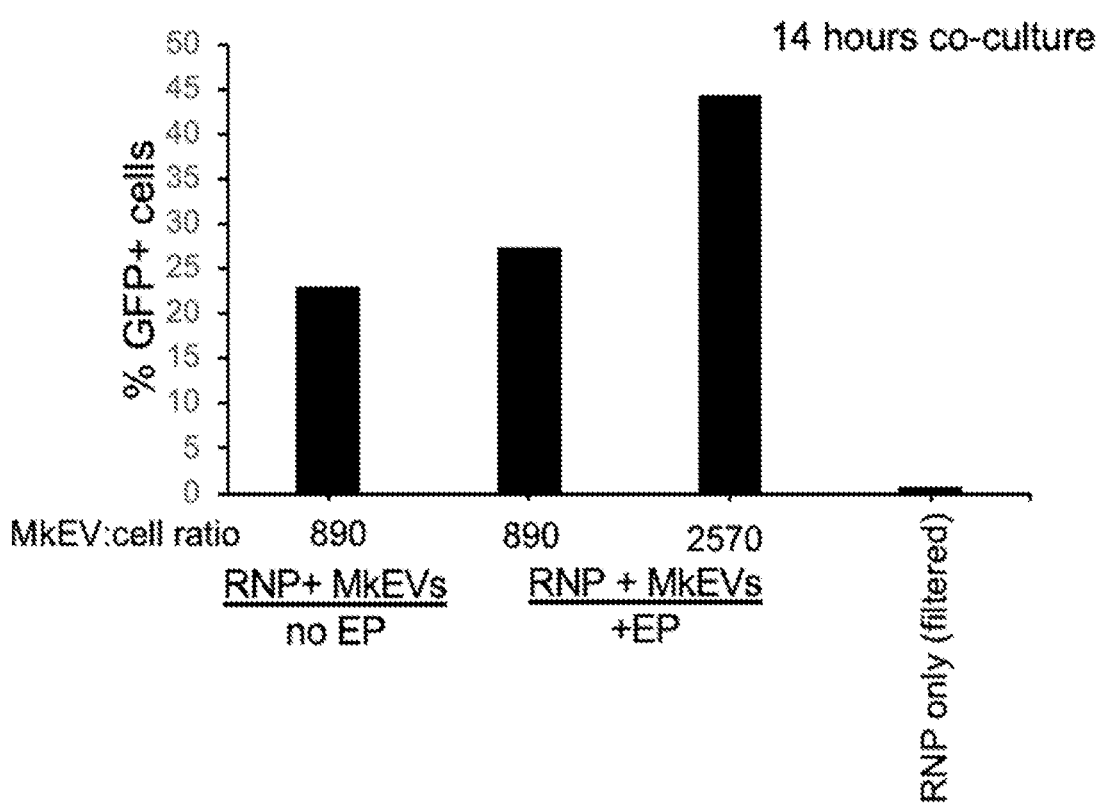

FIGS. 19A-19B show co-culture of cargo-loaded MkEVs using primary murine Lineage negative/c-Kit+/Sca-1+ (LSK) cells derived from mice heterozygous for the JAK2-V617F mutation and doses of 890 and 2570 MkEVs/cell. As seen with homozygous LSK cells, there was an MkEV-mediated uptake of cargo in LSK cells with dose-dependent increase in the number of GFP+ cells with increasing dose of MkEVs/cell as determined by flow cytometry (FIGS. 19A and 19B).

DETAILED DESCRIPTION

The present invention is based, in part on the discovery of compositions and methods useful for the treatment of myeloproliferative diseases or disorders, such as, for example, a myeloproliferative neoplasm (MPN). In some embodiments, the compositions comprise substantially purified megakaryocyte-derived extracellular vesicles that are characterized by particular sets of physical characteristics, such as biomarker makeup (e.g. the presence, absence, or amount of a biomarker) and size, and can carry cargo in the lumen for use in delivering agents, such as therapeutic agents, useful for treating myeloproliferative diseases or disorders, such as, for example, a myeloproliferative neoplasm (MPN). In some embodiments, the megakaryocyte-derived extracellular vesicles of the disclosure are distinct from the naturally occurring products, which are collected from whole blood (Platelet Free Plasma) or derived from activated platelets (Platelet EVs). Accordingly, in aspects, the present invention provides compositions and methods useful for the treatment of myeloproliferative diseases or disorders, such as, for example, a myeloproliferative neoplasm (MPN), using megakaryocyte-derived extracellular vesicles that are consistently produced, with desirable properties, and carry specific cargo—making their therapeutic use for the treatment of myeloproliferative diseases or disorders more likely to be successful.

Methods of Treatment Using Megakaryocyte-Derived Extracellular Vesicles

Myeloproliferative Diseases

Myeloproliferative neoplasms (MPN) are a class of hematologic malignancies arising from haematopoietic progenitors, and include diseases such as chronic myeloid leukemia (CML), polycythemia vera (PV), essential thrombocythemia (ET) and primary myelofibrosis (PMF). In 2005, a recurrent somatic point mutation in the pseudokinase domain of the Janus kinase 2 (JAK2) gene was discovered to be present in a large proportion of patients suffering from these diseases (see, e.g., Levine, R. et al. 2005, Cancer Cell 7:387; James, C. et al. 2005, Nature 434:1144, which is incorporated by reference herein in its entirety). Specifically, in patients with PV, ET, and PMF the activating JAK2V617F mutation occurs with a frequency of between 81-99%, 41-72% and 39-57% respectively (see, e.g., Levine, R. L. et al. 2007, Nat. Rev. Cancer 7:673, which is incorporated by reference herein in its entirety). Additionally, over-activation of JAK/STAT signaling has been described in a subset of patients that do not harbor JAK mutations (see, e.g., Quintas-Cardanam A. et al. 2013, Clinical Cancer Res. Doi:10.1158/1078-0432.CCR-12-0284, which is incorporated by reference herein in its entirety). Taken together, evidence to date supports the targeting of the JAK/STAT pathway, specifically JAK2, in patients with various MPNs.

In various embodiments, the present invention relates to a method for treating a myeloproliferative disease or disorder.

In various embodiments, the present invention relates to a method for treating a disease or disorder characterized by a single point mutation related to a myeloproliferative disease or disorder. In some embodiments, the single point mutation is the JAK2 V617F mutation.

In one aspect, the present invention relates to a method for treating a disease or disorder characterized by a JAK2 V617F mutation comprising administering an effective amount of a composition comprising megakaryocyte-derived extracellular vesicles disclosed herein, which comprise cargo comprising one or more agents capable of treating a myeloproliferative disease or disorder. In some embodiments, the cargo comprises one or more agents capable of treating a MPN. In some embodiments, the agent is a therapeutic agent useful for the treatment of a myeloproliferative disease or disorder, such as a MPN. In some embodiments, the megakaryocyte-derived extracellular vesicles comprise a lipid bilayer membrane surrounding a lumen and derived from a human pluripotent stem cell, wherein the megakaryocyte-derived extracellular vesicle lumen comprises the cargo. In some embodiments, in addition to or as an alternative to the cargo located in the lumen of the megakaryocyte-derived extracellular vesicle, the cargo is associated with the surface of the vesicle. In some embodiments, the cargo comprises one or more selected from a RNA, DNA, protein, carbohydrate, lipid, biomolecule, and small molecule. In some embodiments, the cargo comprises one or more agents, such as therapeutic agents.

In another aspect, the present invention relates to a method for treating a disease or disorder characterized by a JAK2 V617F mutation comprising administering an effective amount of a composition comprising megakaryocyte-derived extracellular vesicles disclosed herein, which comprise cargo comprising one or more agents capable of treating a myeloproliferative disease or disorder, such as MPN. In some embodiments, the agent is a therapeutic agent is capable of treating a MPN. In some embodiments, the composition comprises megakaryocyte-derived extracellular vesicles, which comprise a nucleic acid encoding a functional Janus kinase 2 (JAK2) gene, or a protein product thereof, or a nucleic acid encoding a gene-editing protein capable of creating a functional JAK2 gene, or a protein product thereof.

In embodiments, the method provides a functional Janus kinase (JAK) receptor in the patient. In some embodiments, the JAK receptor is a JAK2 receptor.

In embodiments, the gene is a functional Jak2 gene or encodes a gene-editing protein that is capable of forming a functional Jak2 gene.

In some embodiments, correcting the JAK2 V617F point mutation back to its non-mutant state is sufficient to reverse the myeloproliferative phenotype. In some embodiments, corrected wild-type HSCs will outcompete the JAK2 V617F mutation in vivo, creating a propagation of the therapeutic that can be curative.

In some embodiments, megakaryocyte-derived extracellular vesicles are manufactured from primary human CD34+ cell cultures and are used to correct the JAK2 V617F mutation by delivering gene-targeting nucleic acid, e.g. plasmid DNA, RNA, or the like to affected bone marrow HSCs.

In some embodiments, colonies can be grown from the same patient which contain sufficient numbers of cells for simultaneous genotyping and phenotypic analyses, thereby allowing the direct comparison of phenotypically equivalent mutant and wild-type cells from within the same patient, negating differences in age, sex, treatment, constitutional genetic background, and other confounding variables.

In some embodiments, the disease or disorder characterized by a JAK2 V671F mutation is a myeloproliferative disease or disorder.

In various embodiments, the present invention relates to a method for treating a myeloproliferative disease or disorder. Myeloproliferative diseases and disorders include hematological conditions where there is a primary disorder at the level of the multi-potent hematopoietic stem cell leading to increased production in one or more blood cell types.

In one aspect, the present invention relates to a method for treating a myeloproliferative disease or disorder comprising administering an effective amount of a composition comprising megakaryocyte-derived extracellular vesicles disclosed herein, which comprise cargo comprising one or more agents capable of treating a myeloproliferative disease or disorder, such as a MPN. In some embodiments, the agent is a therapeutic agent useful for the treatment of a myelo-proliferative disease or disorder, such as a MPN. In some embodiments, the megakaryocyte-derived extracellular vesicles comprise a lipid bilayer membrane surrounding a lumen and derived from a human pluripotent stem cell, wherein the megakaryocyte-derived extracellular vesicle lumen comprises the cargo. In some embodiments, in addition to or as an alternative to the cargo located in the lumen of the megakaryocyte-derived extracellular vesicle, the cargo is associated with the surface of the vesicle. In some embodiments, the cargo comprises one or more selected from a RNA, DNA, protein, carbohydrate, lipid, biomol-ecule, and small molecule. In some embodiments, the cargo comprises one or more agents, such as one or more thera-peutic agents.

In an aspect, the present invention relates to a method for treating a myeloproliferative disease or disorder, comprising administering an effective amount of a composition com-prising megakaryocyte-derived extracellular vesicles dis-closed herein, which comprise cargo comprising a nucleic acid encoding a functional myeloproliferative disease or disorder-related gene, such as, for example, an MPN-related gene (e.g. without limitation the JAK2 gene, e.g. lacking the V617F mutation), or a protein product thereof, or a nucleic acid encoding a gene-editing protein capable of creating a functional myeloproliferative disease or disorder-related gene, such as, for example, an MPN-related gene (e.g. without limitation the JAK2 gene, e.g. lacking the V617F mutation), or a protein product thereof, or a nucleic acid encoding a gene-editing protein capable of reducing the product expressed by the mutated gene (e.g. without limi-tation a mutated JAK2 gene such as a JAK2 V671F muta-tion), or a protein product thereof. In a non-limiting example, a nucleic acid encoding a gene-editing protein capable of reducing the product expressed by the mutated gene or a protein product thereof is capable of correcting the mutated gene so a functional protein is expressed. In another non-limiting example, a nucleic acid encoding a gene-editing protein capable of reducing the product expressed by the mutated gene or a protein product thereof can alter the mutated gene so the mutated protein is no longer expressed.

In another aspect, the present invention relates to a method for treating a myeloproliferative disease or disorder, comprising administering an effective amount of a compo-sition comprising a cell which is contacted with a compo-sition comprising megakaryocyte-derived extracellular vesicles disclosed herein in vitro, wherein the megakaryo-cyte-derived extracellular vesicles comprise cargo compris-ing a nucleic acid encoding a functional myeloproliferative disease or disorder-related gene, such as, for example, an MPN-related gene (e.g. without limitation the JAK2 gene, e.g. lacking the V617F mutation), or a protein product thereof, or a nucleic acid encoding a gene-editing protein capable of creating a functional myeloproliferative disease or disorder-related gene, such as, for example, an MPN-related gene (e.g. without limitation the JAK2 gene, e.g. lacking the V617F mutation), or a protein product thereof, or a nucleic acid encoding a gene-editing protein capable of reducing the product expressed by the mutated gene (e.g. without limitation a mutation in the JAK2 gene such as a JAK2 V671F mutation), or a protein product thereof.

In another aspect, the present invention relates to a method for treating a myeloproliferative disease or disorder, comprising:

(a) obtaining a plurality of substantially purified mega-karyocyte-derived extracellular vesicles of the disclo-sure;

(b) incubating the plurality of substantially purified mega-karyocyte-derived extracellular vesicles with a thera-peutic agent to allow the therapeutic agent to populate the lumen of the megakaryocyte-derived extracellular vesicle and/or associate with the surface of the mega-karyocyte-derived extracellular vesicle and yield a deliverable therapeutic agent, wherein the therapeutic agent is capable of treating a myeloproliferative disease or disorder; and (c) administering the deliverable therapeutic agent to a patient or contacting the deliverable therapeutic agent with a biological cell in vitro and administering the contacted biological cell to a patient, wherein the megakaryocyte-derived extracellular vesicles are substantially purified and comprise a lipid bilayer membrane surrounding a lumen, the megakaryocyte-derived extracellular vesicle lumen comprises the therapeutic agent and/or is associated with the surface of the megakaryocyte-derived extra-cellular vesicle; and the lipid bilayer membrane comprises one or more pro-teins associated with or embedded within.

In another aspect, the present invention relates to a method for treating a myeloproliferative disease or disorder, comprising:

(a) obtaining a plurality of substantially purified mega-karyocyte-derived extracellular vesicles of the disclo-sure; the megakaryocyte-derived extracellular vesicles comprising a lipid bilayer membrane surrounding a lumen, wherein:

the lipid bilayer membrane comprises one or more proteins associated with or embedded within;

(b) incubating the plurality of substantially purified mega-karyocyte-derived extracellular vesicles with a thera-peutic agent to allow the therapeutic agent to populate the lumen of the megakaryocyte-derived extracellular vesicle and/or associate with the surface of the mega-karyocyte-derived extracellular vesicle and yield a deliverable therapeutic agent, wherein the therapeutic agent is capable of creating a gene edit of a V617F mutation in a JAK2 gene of a myeloproliferative neoplasm cell;

(c) administering the deliverable therapeutic agent to a patient or contacting the deliverable therapeutic agent with a biological cell in vitro and administering the contacted biological cell to a patient, thereby editing the V617F mutation to treat the myeloproliferative disease or disorder in the patient.

In some embodiments, the disclosure provides a method for treating a myeloproliferative disease or disorder, com-prising administering an effective amount of a composition disclosed herein, wherein the composition comprises mega-karyocyte-derived extracellular vesicles which comprise cargo comprising a nucleic acid encoding a functional myeloproliferative disease or disorder-related gene, such as, for example, an MPN-related gene (e.g. without limitation the JAK2 gene, e.g. lacking the V617F mutation), or a protein product thereof, or a nucleic acid encoding a gene-editing protein capable of creating a functional myelopro-liferative disease or disorder-related gene, such as, for example, an MPN-related gene (e.g. without limitation the JAK2 gene, e.g. lacking the V617F mutation), or a protein product thereof.

In some embodiments, the disclosure provides a method for treating a myeloproliferative disease or disorder, comprising administering an effective amount of a composition comprising a cell which is contacted in vitro with megakaryocyte-derived extracellular vesicles which comprise cargo comprising a nucleic acid encoding a functional myeloproliferative disease or disorder-related gene, such as, for example, an MPN-related gene (e.g. without limitation the JAK2 gene, e.g. lacking the V617F mutation), or a protein product thereof, or a nucleic acid encoding a gene-editing protein capable of creating a functional myeloproliferative disease or disorder-related gene, such as, for example, an MPN-related gene (e.g. without limitation the JAK2 gene, e.g. lacking the V617F mutation), or a protein product thereof.

In some embodiments, the myeloproliferative disease or disorder is selected from a myeloproliferative neoplasm (MPN), polycythemia vera, thrombocythemia, essential thrombocythemia, idiopathic myelofibrosis, myelofibrosis, acute myeloid leukemia, systemic mastocytosis (SM), chronic neutrophilic leukemia (CNL), and myelodysplastic syndrome (MDS). In some embodiments the myelofibrosis is selected from primary myelofibrosis, secondary myelofibrosis, post-essential thrombocythemia myelofibrosis, post-polycythemia vera myelofibrosis, myeloid metaplasia with myelofibrosis, chronic myelogenous leukaemia (CML), chronic myelomonocytic leukemia, hypereosinophilic syndrome, juvenile myelomonocytic leukemia, and systemic mast cell disease.

In some embodiments, the method obviates the need for hematopoietic stem cell (HSC) transplantation, including allogenic HSC transplantation, and/or myeloablative chemotherapy.

In some embodiments, the method reduces the likelihood of the patient developing graft-versus-host disease, vascular diseases, including thrombosis, coronary heart disease, arteriosclerosis, cerebral ischemia, cerebral infarction, thrombohemorrhagic events, vascular complications, splenomegaly, progressive cytopenia, and/or hypercelluarbone marrow.

In some embodiments, the method reduces the severity of the myeloproliferative disease or disorder.

In some embodiments, the method causes a decrease in white blood cell count in the patient. In some embodiments, the method causes a decrease in neutrophil count in the patient. In some embodiments, the method causes a decrease in reticulocyte count in the patient. In some embodiments, the method causes a decrease in platelet count in the patient. In some embodiments, the method causes a reduction in spleen size in the patient.

In some embodiments, the functional Jak2 gene restores white blood cell count, neutrophil count, reticulocyte count, platelet count, and/or spleen size to undiseased levels. In some embodiments, the functional Jak2 gene restores white blood cell count, neutrophil count, reticulocyte count, platelet count, and/or spleen size to between about 40% and about 50% of undiseased levels. In some embodiments, the functional Jak2 gene restores white blood cell count, neutrophil count, reticulocyte count, platelet count, and/or spleen size to about 50% and about 60% of undiseased levels. In some embodiments, the functional Jak2 gene restores white blood cell count, neutrophil count, reticulocyte count, platelet count, and/or spleen size to about 60% and about 70% of undiseased levels. In some embodiments, the functional Jak2 gene restores white blood cell count, neutrophil count, reticulocyte count, platelet count, and/or spleen size to about 70% and about 80% of undiseased levels. In some embodiments, the functional Jak2 gene restores white blood cell count, neutrophil count, reticulocyte count, platelet count, and/or spleen size to about 80% and about 90% of undiseased levels. In some embodiments, the functional Jak2 gene restores white blood cell count, neutrophil count, reticulocyte count, platelet count, and/or spleen size to about 90% and about 100% of undiseased levels.

In some embodiments, a patient having a myeloproliferative disease or disorder is administered a treatment comprising megakaryocyte-derived extracellular vesicles in combination with a treatment selected from one or more of a Janus kinase (JAK) inhibitor and a phosphatidylinositol 3-kinase (PI3K) inhibitor.

Non-limiting examples of JAK inhibitors include ruxolitinib, fedratinib, tofacitinib, baricitinib, lestaurtinib, pacritinib, XL019, AZD1480, INCB039110, LY2784544, BMS911543, NS018, or N-(cyanomethyl)-4-[2-(4-morpholinoanilino)pyrimidin-4-yl]benzamide; or pharmaceutically acceptable salts thereof.

Non-limiting examples of PI3K inhibitors include L147, BKM120, GDC-0941, BAY80-6946, PX-866, CH5132799, XL756, BEZ235, and GDC-0980, wortmannin, LY294002, PI3K II, TGR-1202, AMG-319, GSK2269557, X-339, X-414, RP5090, KAR4141, XL499, OXY111A, IPI-145, IPI-443, GSK2636771, BAY 10824391, buparlisib, BYL719, RG7604, MLN1117, WX-037, AEZS-129, PA799, ZSTK474, AS252424, TGX221, TG100115, IC87114, (S)-2-(1-((9H-purin-6-yl)amino)propyl)-5-fluoro-3-phenylquinazolin-4(3H)-one, (S)-2-(1-((9H-purin-6-yl)amino)ethyl)-6-fluoro-3-phenylquinazolin-4(3H)-one, (S)-2,4-diamino-6-(((5-chloro-8-fluoro-4-oxo-3-(pyridin-3-yl)-3,4-dihydroquinazolin-2-yl)(cyclopropyl)methyl)amino) pyrimidine-5-carbonitrile; or a pharmaceutically acceptable salt thereof.

Methods of Gene Editing a Cell Using Megakaryocyte-Derived Extracellular Vesicles In various embodiments, the present invention relates to gene editing a cell using megakaryocyte-derived extracellular vesicles of the disclosure.

In some embodiments, the method for gene editing a cell comprises:

(a) contacting the cell with a composition comprising a plurality of substantially purified megakaryocyte-derived extracellular vesicles comprising a lipid bilayer membrane surrounding a lumen, wherein:

the megakaryocyte-derived extracellular vesicle lumen comprises cargo comprising an agent suitable for gene editing the cell and/or cargo comprising an agent suitable for gene editing the cell associated with the surface of the megakaryocyte-derived extracellular vesicle; and the lipid bilayer membrane comprises one or more proteins associated with or embedded within, and (b) gene editing the cell to alter a mutation in a JAK2 gene therein.

In some embodiments, the cell comprises a JAK2 gene comprising SEQ ID NO: 1, which refers to the wild-type JAK2 gene sequence, or fragment thereof:

(SEQ ID NO: 1)
TTGTATCCTCATCTATAGTCATGCTGAAAGTAGGAGAAAGTGCATCTTT

ATTATGGCAGAGAGAATTTTCTGAACTATTTATGGACAACAGTCAAACA

ACAATTCTTTGTACTTTTTTTTTTCCTTAGTCTTTCTTTGAAGCAGCAA

-continued

```
GTATGATGAGCAAGCTTTCTCACAAGCATTTGGTTTTAAATTATGGAGT

ATGTGTCTGTGGAGACGAGAGTAAGTAAAACTACAGGCTTTCTAATGCC

TTTCTCAGAGCATCTGTTTTTGTTTATATAGAAAATTCAGTTTCAGGAT

CACAGCTAGGTGTCAGTGTAAACTATAATTTAACAGGAGTTAAGTATTT

TTGAAACTGAAAACACTGTAGGACTATTCAGTTATATCTTGTGAAAAAG

GAAAGCAAT.
```

In some embodiments, SEQ ID NO: 1 comprises one or more mutations that cause abnormal production of JAK2 protein. In some embodiments, the mutation is a single-point mutation. Non-limiting examples of such a mutation include the V617F mutation, which has been identified in patients with myeloproliferative neoplasms (MPN). In one aspect, the method of the disclosure is useful for editing one or more mutations in the JAK2 gene, including the V617F mutation, to provide a functional JAK2 gene. In some embodiments, the mutation in a JAK2 gene comprises the V617F mutation.

Any agent suitable for gene editing a cell and/or capable of altering a mutation in the JAK2 gene is contemplated by the present disclosure. In some embodiments, the cargo comprising an agent suitable for gene editing the cell is in the lumen and/or associated with the surface of the megakaryocyte-derived extracellular vesicles.

In some embodiments, the agent is one or more therapeutic agents. In some embodiments, the agent is one or more therapeutic agents is suitable for gene editing a cell and/or capable of altering a mutation in the JAK2 gene. In some embodiments, the therapeutic agent is a nucleic acid therapeutic agent. In some embodiments, the nucleic acid therapeutic agent is selected from one or more non-autologous and/or recombinant nucleic acid constructs selected from mRNA, tRNA, rRNA, siRNA, microRNA, regulating RNA, non-coding and coding RNA, linear DNA, DNA fragments, or DNA plasmids. In some embodiments, the nucleic acid therapeutic agent is mRNA, and optionally: is in vitro transcribed or synthetic and/or comprises one or more non-canonical nucleotides, optionally selected from pseudouridine and 5-methoxyuridine. In some embodiments, the nucleic acid therapeutic agent encodes a functional protein. In embodiments, the nucleic acid therapeutic agent encodes a gene-editing protein and/or associated elements for gene-editing functionality. In embodiments, the gene-editing protein is selected from a zinc finger (ZF), transcription activator-like effector (TALE), meganuclease, and clustered regularly interspaced short palindromic repeat (CRISPR)-associated protein. In embodiments, the CRISPR-associated protein is selected from Cas9, CasX, CasY, Cpf1, and gRNA complexes thereof. In some embodiments, the CRISPR-associated protein is selected from Cas9, xCas9, Cas12a (Cpf1), Cas13a, Cas14, CasX, CasY, a Class 1 Cas protein, a Class 2 Cas protein, MAD7, and gRNA complexes thereof. In some embodiments, the CRISPR-associated protein is Cas9.

In some embodiments, in a population of cells comprising a mutation in a JAK2 gene, the gene editing alters and/or corrects the mutation in greater than about 10%, 15%, 20%, 25%, 30%, 35%, 40%, 45%, 50%, 55%, 60%, 65%, 70%, 75%, 80%, 85%, 90%, 95%, 96, 97%, 98%, or 99% of the cells in the population. In some embodiments, the mutation is the V617F mutation.

In some embodiments, the composition comprising megakaryocyte-derived extracellular vesicles is a pharmaceutical composition further comprising a pharmaceutically acceptable excipient or carrier.

Cargo of Megakaryocyte-Derived Extracellular Vesicles

Megakaryocyte-derived extracellular vesicles may contain diverse cargo that comprise molecules such as mRNAs, microRNAs, and cytokines that are capable of treating a myeloproliferative disease or disorder, such as a MPN. Megakaryocyte-derived extracellular vesicles are able to transfer their cargo to alter the function of target cells. They exert their influence on the target cells through surface receptor signaling, plasma membrane fusion, and internalization. By loading megakaryocytes or megakaryocyte-derived extracellular vesicles with cargo comprising biologic or therapeutic molecules useful for the treatment of a myeloproliferative disease or disorder, megakaryocyte-derived extracellular vesicles can be further used as delivery vehicles to achieve a targeted therapeutic effect for treating the myeloproliferative disease or disorder. Until now, small RNAs (siRNA and miRNA), small linear DNA, and plasmid DNA have all been successfully loaded into megakaryocyte-derived extracellular vesicles for a variety of delivery applications. Megakaryocyte-derived extracellular vesicles targeting is defined by their complement of surface proteins and can be further engineered to express or remove specific biomarkers of interest to refine biodistribution and cell-cell recognition. For instance, the present megakaryocyte-derived extracellular vesicles, with their unique biomarker profiles, are particularly suited for delivery of payloads, e.g. therapies useful for treating a myeloproliferative disease or disorder, such as a MPN.

In embodiments, the megakaryocyte-derived extracellular vesicles are suitable for loading with cargo into the lumen. In some embodiments, the cargo comprises one or more agents, such as one or more therapeutic agents, suitable for a myeloproliferative disease or disorder. In some embodiments, the cargo comprises one or more of a RNA, DNA, protein, carbohydrate, lipid, biomolecule, and small molecule. In some embodiments, the cargo comprises a biologically produced component. In some embodiments, the cargo comprises a synthetically produced component. In some embodiments, the cargo is pre-loaded into megakaryocyte-derived extracellular vesicles. In some embodiments, a biological component is overexpressed in megakaryocytes so that generated megakaryocyte-derived extracellular vesicles comprise the biological component. In some embodiments, the cargo is post-loaded into megakaryocyte-derived extracellular vesicles. In some embodiments, purified megakaryocyte-derived extracellular vesicles are mixed with cargo to generate cargo-loaded megakaryocyte-derived extracellular vesicles. In some embodiments, the cargo is hydrophobic. In some embodiments, the cargo is hydrophilic. In some embodiments, the cargo is integrated into the lipid bilayer of the megakaryocyte-derived extracellular vesicles. In some embodiments, the cargo is located in the lumen of the megakaryocyte-derived extracellular vesicles.

In some embodiments, in addition to or as an alternative to the cargo located in the lumen of the meg akaryocyte-derived extracellular vesicles, the cargo is associated with the meg akaryocyte-derived extracellular vesicles. In some embodiments, the cargo is associated with the surface and/or the exterior of the megakaryocyte-derived extracellular vesicles. Non-limiting examples of cargo associated with the megakaryocyte-derived extracellular vesicles includes cargo that is covalently conjugated to the surface of the vesicle, or cargo that is associated with the surface via electrostatic interactions. As would be understood by one of ordinary skill in the art, cargo associated with the megakaryocyte-derived extracellular vesicles can still be transported even when not loaded into the lumen of the vesicle.

In some embodiments, the cargo is loaded into the megakaryocyte-derived extracellular vesicle using an active loading strategy, which is physically-induced and/or chemically-induced. In some embodiments, the active loading strategy is physically-induced. In some embodiments, the physically-induced active loading strategy comprises the mechanical or physical disruption of the megakaryocyte-derived extracellular vesicle lipid bilayer through external forces, such as electroporation, sonication, freeze-thaw cycling, and extrusion. In some embodiments, the electroporation involves the use of an electric field to induce spontaneous pore formation in the megakaryocyte-derived extracellular vesicle lipid bilayer, wherein the presence of the electric field disrupts the lipid bilayer, while removal of the field enables closure of pores and reformation of the lipid layer after the cargo has been taken up by the megakaryocyte-derived extracellular vesicle. In some embodiments, the sonication involves ultrasound energy applied through a sonicator probe that decreases the rigidity of the megakaryocyte-derived extracellular vesicle lipid bilayer, enabling cargo diffusion. In some embodiments, the freeze-thaw cycling uses thermal energy to facilitate megakaryocyte-derived extracellular vesicle cargo loading. In some embodiments, extrusion is performed following established protocols for formation of synthetic liposomes, wherein megakaryocyte-derived extracellular vesicles are mixed with free cargo and passed through membranes containing nanoscale pores, wherein the sheer force disrupts the lipid bilayer, allowing exogenous cargo to enter megakaryocyte-derived extracellular vesicles.

In some embodiments, the active loading strategy is chemically-induced. In some embodiments, the chemically-induced active loading strategy comprises the use of chemical agents, such as saponin or transfection reagents, to bypass the megakaryocyte-derived extracellular vesicle lipid bilayer. In some embodiments, the chemical agent is a detergent, such as saponin. In some embodiments, the saponin is used to selectively remove cholesterol from the megakaryocyte-derived extracellular vesicle lipid bilayer, opening pores in the lipid bilayer. In some embodiments, the chemical agent is a transfection agent. In some embodiments, the transfection agent is used to deliver nucleic acids into the megakaryocyte-derived extracellular vesicle by exploiting cationic substances that promote interactions with the lipid bilayer and subsequent internalization. In some embodiments, the transfection agent is lipofectamine and/or a lipid-based agent.

In some embodiments, the loading ratio of a nucleic acid (i.e. copies of nucleic acid per vesicle) into megakaryocyte-derived extracellular vesicles of the disclosure ranges from about 1 to about 1000, about 1 to about 500, about 1 to about 100, about 10 to about 1000, about 100 to about 1000, about 500 to about 1000, about 100 to about 500,000, about 1000 to about 300,000, about 100,000 to about 300,000, about 1000, to about 10,000, or about 1000 to about 5000. In some embodiments, the loading ratio of a nucleic acid into megakaryocyte-derived extracellular vesicles of the disclosure ranges from about 100 to about 1000, about 600 to about 700, about 1000 to about 10,000, about 5000 to about 10,000, about 2000 to about 4000, about 5000 to about 7000, about 8000 to about 9000, or about 8000 to about 8500. In some embodiments, the loading ratio of a nucleic acid into megakaryocyte-derived extracellular vesicles of the disclosure is 500, about 3000, about 6000, or about 8300. In some embodiments, the nucleic acid is DNA. In some embodiments, the nucleic acid is plasmid DNA.

In some embodiments, the loading efficiency for loading cargo, such as cargo comprising a nucleic acid, into megakaryocyte-derived extracellular vesicles of the disclosure ranges from about 1% to about 99%, about 10% to about 90%, about 30% to about 70%, about 40% to about 60%, about 40% to about 50%, or about 50% to about 60%. In some embodiments, the cargo comprises a nucleic acid. In some embodiments, the nucleic acid is DNA. In some embodiments, the nucleic acid is plasmid DNA. In some embodiments, loading efficiency is calculated using the following equation:

$$\text{Loading efficiency (\%)} = \text{cargo} + \text{MV\#/Total MV\#}$$

In some embodiments, the surface of megakaryocyte-derived extracellular vesicles is modified to impact biodistribution and targeting capabilities of megakaryocyte-derived extracellular vesicles. In some embodiments, surface ligands are added to megakaryocyte-derived extracellular vesicles through genetic engineering. In some embodiments, the megakaryocyte-derived extracellular vesicles are generated that express fusion proteins in their lipid bilayers. In some embodiments, the endogenous proteins in megakaryocyte-derived extracellular vesicle lipid bilayers are fused with targeting ligands through cell engineering.

In embodiments, the cargo comprises one or more therapeutic agents useful for the treatment of a myeloproliferative disease or disorder, such as a MPN. In embodiments, the therapeutic agent is a nucleic acid therapeutic agent. In embodiments, the nucleic acid therapeutic agent encodes a functional protein.

In embodiments, the nucleic acid therapeutic agent is selected from one or more non-autologous and/or recombinant nucleic acid constructs selected from mRNA, tRNA, rRNA, siRNA, microRNA, regulating RNA, non-coding and coding RNA, linear DNA, DNA fragments, or DNA plasmids. In some embodiments, the nucleic acid therapeutic agent is selected from one or more of mRNA, miRNA, siRNA, and snoRNA.

In embodiments, the nucleic acid therapeutic agent encodes a wild type gene, which is defective in the patient. In embodiments, the nucleic acid therapeutic agent is mRNA, and optionally: is in vitro transcribed or synthetic and/or comprises one or more non-canonical nucleotides, optionally selected from pseudouridine and 5-methoxyuridine.

In some embodiments, the one or more non-canonical nucleotides are selected from 2-thiouridine, 5-azauridine, pseudouridine, 4-thiouridine, 5-methyluridine, 5-methylpseudouridine, 5-aminouridine, 5-aminopseudouridine, 5-hydroxyuridine, 5-hydroxypseudouridine, 5-methoxyuridine, 5-methoxypseudouridine, 5-ethoxyuridine, 5-ethoxypseudouridine, 5-hydroxymethyluridine, 5-hydroxymethylpseudouridine, 5-carboxyuridine, 5-carboxypseudouridine, 5-formyluridine, 5-formylpseudouridine, 5-methyl-5-azauridine, 5-amino-5-azauridine, 5-hydroxy-5-azauridine, 5-methylpseudouridine, 5-aminopseudouridine, 5-hydroxypseudouridine, 4-thio-5-azauridine, 4-thiopseudouridine, 4-thio-5-methyluridine, 4-thio-5-aminouridine, 4-thio-5-hydroxyuridine, 4-thio-5-methyl-5-azauridine, 4-thio-5-amino-5-azauridine, 4-thio-5-hydroxy-5-azauridine, 4-thio-5-methylpseudouridine, 4-thio-5-aminopseudouridine, 4-thio-5-hydroxypseudouridine, 2-thiocytidine, 5-azacytidine, pseudoisocytidine, N4-methylcytidine, N4-aminocytidine, N4-hydroxycytidine, 5-methylcytidine, 5-aminocytidine, 5-hydroxycytidine, 5-methoxycytidine, 5-ethoxycytidine, 5-hydroxymethylcytidine, 5-carboxycytidine, 5-formylcytidine, 5-methyl-5-azacytidine, 5-amino-5-azacytidine, 5-hydroxy-5-azacytidine, 5-methyl pseudoisocytidine, 5-aminopseudoisocytidine, 5-hydroxypseudoisocytidine, N4-methyl-5-azacytidine, N4-methylpseudoisocytidine, 2-thio-5-azacytidine, 2-thio-pseudoisocytidine, 2-thio-N4-methylcytidine, 2-thio-N4-aminocytidine, 2-thio-N4-hydroxycytidine, 2-thio-5-methylcytidine, 2-thio-5-aminocytidine, 2-thio-5-hydroxycytidine, 2-thio-5-methyl-5-azacytidine, 2-thio-5-amino-5-azacytidine, 2-thio-5-hydroxy-5-azacytidine, 2-thio-5-methylpseudoisocytidine, 2-thio-2-thio-5-hydroxypseudoisocytidine, 2-thio-N4-methyl-5-azacytidine, 2-thio-N4-methylpseudoisocytidine, N4-methyl-5-methyl-cytidine, N4-methyl-5-aminocytidine, N4-methyl-5-hydroxycytidine, N4-methyl-5-methyl-5-azacytidine, N4-methyl-5-amino-5-azacytidine, N4-methyl-5-hydroxy-5-azacytidine, N4-methyl-5-methylpseudoisocytidine, N4-methyl-5-aminopseudoisocytidine, N4-methyl-5-hydroxypseudoisocytidine, N4-amino-5-azacytidine, N4-aminopseudoisocytidine, N4-amino-5-methylcytidine, N4-amino-5-aminocytidine, N4-amino-5-hydroxycytidine, N4-amino-5-methyl-5-azacytidine, N4-amino-5-amino-5-azacytidine, N4-amino-5-hydroxy-5-azacytidine, N4-amino-5-methylpseudoisocytidine, N4-amino-5-aminopseudoisocytidine, N4-amino-5-hydroxypseudoisocytidine, N4-hydroxy-5-azacytidine, N4-hydroxypseudoisocytidine, N4-hydroxy-5-methylcytidine, N4-hydroxy-5-aminocytidine, N4-hydroxy-5-hydroxycytidine, N4-hydroxy-5-methyl-5-azacytidine, N4-hydroxy-5-amino-N4-hydroxy-5-hydroxy-5-azacytidine, N4-hydroxy-5-methylpseudoisocytidine, N4-hydroxy-5-aminopseudoisocytidine, N4-hydroxy-5-hydroxypseudoisocytidine, 2-thio-N4-methyl-5-methylcytidine, 2-thio-N4-methyl-5-aminocytidine, 2-thio-N4-methyl-5-hydroxycytidine, 2-thio-N4-methyl-2-thio-N4-methyl-5-amino-5-azacytidine, 2-thio-N4-methyl-5-hydroxy-5-azacytidine, 2-thio-N4-methyl-5-methylpseudoisocytidine, 2-thio-N4-methyl-5-aminopseudoisocytidine, 2-thio-N4-methyl-5-hydroxypseudoisocytidine, 2-thio-N4-amino-5-azacytidine, 2-thio-N4-aminopseudoisocytidine, 2-thio-N4-amino-5-methylcytidine, 2-thio-N4-amino-5-aminocytidine, 2-thio-N4-amino-5-hydroxycytidine, 2-thio-N4-amino-5-methyl-5-azacytidine, 2-thio-N4-amino-5-amino-5-azacytidine, 2-thio-N4-amino-5-hydroxy-5-azacytidine, 2-thio-N4-amino-5-methylpseudoisocytidine, 2-thio-N4-amino-5-aminopseudoisocytidine, 2-thio-N4-amino-5-hydroxypseudoisocytidine, 2-thio-N4-hydroxy-5-azacytidine, 2-thio-N4-hydroxypseudoisocytidine, 2-thio-N4-hydroxy-5-methylcytidine, N4-hydroxy-5-aminocytidine, 2-thio-N4-hydroxy-5-hydroxycytidine, 2-thio-N4-hydroxy-5-methyl-5-azacytidine, 2-thio-N4-hydroxy-5-amino-5-azacytidine, 2-thio-N4-hydroxy-5-hydroxy-5-azacytidine, 2-thio-N4-hydroxy-5-methylpseudoisocytidine, 2-thio-N4-hydroxy-5-aminopseudoisocytidine, 2-thio-N4-hydroxy-5-hydroxypseudoisocytidine, N6-methyladenosine, N6-aminoadenosine, N6-hydroxyadenosine, 7-deazaadenosine, 8-azaadenosine, N6-methyl-7-deazaadenosine, N6-methyl-8-azaadenosine, 7-deaza-8-azaadenosine, N6-methyl-7-deaza-8-azaadenosine, N6-amino-7-deazaadenosine, N6-amino-8-azaadenosine, N6-amino-7-deaza-8-azaadenosine, N6-hydroxyadenosine, N6-hydroxy-7-deazaadenosine, N6-hydroxy-8-azaadenosine, N6-hydroxy-7-deaza-8-azaadenosine, 6-thioguanosine, 7-deazaguanosine, 8-azaguanosine, 6-thio-7-deazaguanosine, 6-thio-8-azaguanosine, 7-deaza-8-azaguanosine, and 6-thio-7-deaza-8-azaguanosine.

In some embodiments, the present methods comprise gene-editing and/or gene correction. In some embodiments, the present methods encompass synthetic RNA-based gene-editing and/or gene correction, e.g. with RNA comprising non-canonical nucleotides, e.g. RNA encoding one or more of a nuclease, a transcription activator-like effector nuclease (TALEN), a zinc-finger nuclease, a meganuclease, a nickase, a clustered regularly interspaced short palindromic repeat (CRISPR)-associated protein a DNA-repair protein, a DNA-modification protein, a base-modification protein, a DNA methyltransferase, a protein that causes DNA demethylation, an enzyme for which DNA is a substrate or a natural or engineered variant, family-member, orthologue, fragment or fusion construct thereof. In some embodiments, the efficiency of the gene-editing and/or gene correction is high, for example, higher than DNA-based gene editing and/or gene correction. In some embodiments, the present methods of gene-editing and/or gene correction are efficient enough for in vivo application. In some embodiments, the present methods of gene-editing and/or gene correction are efficient enough to not require cellular selection (e.g. selection of cells that have been edited). In some embodiments, the efficiency of gene-editing of the present methods is about 1%, or about 2%, or about 3%, or about 4%, or about 5%, or about 6%, or about 7%, or about 8%, or about 9%, or about 10%, or about 20%, or about 30%, or about 40%, or about 50%, or about 60%, or about 70%, or about 80%, or about 90%, or about 100%. In some embodiments, the efficiency of gene-correction of the present methods is about 1%, or about 2%, or about 3%, or about 4%, or about 5%, or about 6%, or about 7%, or about 8%, or about 9%, or about 10%, or about 20%, or about 30%, or about 40%, or about 50%, or about 60%, or about 70%, or about 80%, or about 90%, or about 100%

In some embodiments, the present methods comprise high-efficiency gene-editing proteins comprising engineered nuclease cleavage or DNA-modification domains. In some embodiments, the methods comprise high-fidelity gene-editing proteins comprising engineered nuclease cleavage or DNA-modification domains. In some embodiments, the high-efficiency gene-editing proteins comprising engineered DNA-binding domains. In some embodiments, the high-fidelity gene-editing proteins comprising engineered DNA-binding domains. In some embodiments, the methods comprise gene-editing proteins comprising engineered repeat sequences. In some embodiments, the methods comprise gene-editing proteins comprising one or more CRISPR associated family members. In some embodiments, the methods comprise altering the DNA sequence of a cell by transfecting the cell with or inducing the cell to express a gene-editing protein. In some embodiments, the methods comprise altering the DNA sequence of a cell that is present in an in vitro culture. In some embodiments, the methods comprise altering the DNA sequence of a cell that is present in vivo.

In some embodiments, the methods comprise one or more steroids and/or one or more antioxidants in the transfection medium can increase in vivo transfection efficiency, in vivo reprogramming efficiency, and in vivo gene-editing efficiency. In some embodiments, the methods comprise contacting a cell or patient with a glucocorticoid, such as hydrocortisone, prednisone, prednisolone, methylprednisolone, dexamethasone or betamethasone. In some embodiments, the methods comprise inducing a cell to express a protein of interest by contacting a cell with a medium containing a steroid and contacting the cell with one or more nucleic acid molecules. In some embodiments, the nucleic acid molecule comprises synthetic RNA. In some embodiments, the steroid is hydrocortisone. In some embodiments, the hydrocortisone is present in the medium at a concentration of between about 0.1 uM and about 10 uM, or about 1 uM. In some embodiments, the methods comprise inducing a cell in vivo to express a protein of interest by contacting the cell with a medium containing an antioxidant and contacting the cell with one or more nucleic acid molecules. In some embodiments, the antioxidant is ascorbic acid or ascorbic-acid-2-phosphate. In some embodiments, the ascorbic acid or ascorbic-acid-2-phosphate is present in the medium at a concentration of between about 0.5 mg/L and about 500 mg/L, including about 50 mg/L. In some embodiments, the methods comprise reprogramming and/or gene-editing a cell in vivo by contacting the cell with a medium containing a steroid and/or an antioxidant and contacting the cell with one or more nucleic acid molecules, wherein the one or more nucleic acid molecules encodes one or more reprogramming and/or gene-editing proteins. In some embodiments, the cell is present in an organism, and the steroid and/or antioxidant are delivered to the organism.

In embodiments, the nucleic acid therapeutic agent is useful for the treatment of a myeloproliferative disease or disorder. In some embodiments, the nucleic acid therapeutic agent encodes a gene-editing protein and/or associated elements for gene-editing functionality useful for editing a cell to alter a mutation in a gene associated with a myeloproliferative disease or disorder, such as the JAK2 gene. In embodiments, the gene-editing protein is selected from a zinc finger (ZF), transcription activator-like effector (TALE), meganuclease, and clustered regularly interspaced short palindromic repeat (CRISPR)-associated protein. In embodiments, the CRISPR-associated protein is selected from Cas9, CasX, CasY, Cpf1, and gRNA complexes thereof. In some embodiments, the CRISPR-associated protein is selected from Cas9, xCas9, Cas12a (Cpf1), Cas13a, Cas14, CasX, CasY, a Class 1 Cas protein, a Class 2 Cas protein, MAD7, and gRNA complexes thereof.

In embodiments, the therapeutic agent is a biologic therapeutic agent useful for the treatment of a myeloproliferative disease or disorder. In embodiments, the biologic therapeutic agent is a protein. In some embodiments, the biologic therapeutic agent is an interferon, a monoclonal antibody, and/or an interleukin. In some embodiments, the biologic therapeutic agent is used to effect immunotherapy selected from one or more of specific active immunotherapy, non-specific active immunotherapy, passive immunotherapy, and cytotoxic therapy.

In embodiments, the biologic therapeutic agent is a recombinant protein useful for the treatment of a myeloproliferative disease or disorder.

In embodiments, the biologic therapeutic agent is a virus useful for the treatment of a myeloproliferative disease or disorder.

In embodiments, the biologic therapeutic agent is one of an antibody or an antibody fragment, fusion protein, gene-editing protein, cytokine, antigen, and peptide useful for the treatment of a myeloproliferative disease or disorder.

In embodiments, the therapeutic agent is a small molecule therapeutic agent useful for the treatment of a myeloproliferative disease or disorder. In some embodiments, the small molecule therapeutic agent is one or more of a drug, inhibitor, or cofactor. In some embodiments, the drug for use in cancer therapy. In some embodiments, the inhibitor is one or more of a kinase inhibitor, proteasome inhibitor, and inhibitor targeting apoptosis.

In embodiments, the therapeutic agent is a vaccine and/or an immunogenic antigen useful for the treatment of a myeloproliferative disease or disorder.

Megakaryocyte-Derived Extracellular Vesicles

In one aspect, the disclosure provides megakaryocyte-derived extracellular vesicles useful for the treatment of a myeloproliferative disease or disorder, such as MPN. In some embodiments, the megakaryocyte-derived extracellular vesicles comprise cargo useful for the treatment of a myeloproliferative disease or disorder, such as MPN.

Megakaryocyte-derived extracellular vesicles, which are relatively immune silent, can be repeatedly dosed; a distinct advantage when compared to immunogenic viral vectors. In some aspects, the megakaryocyte-derived extracellular vesicles are useful for in vivo genomic medicines that do not need conditioning treatments, so people can receive them in an outpatient setting. This platform is an important paradigm shift in gene therapy from ex vivo to in vivo delivery, that will democratize gene therapy by reducing time to treatment and cost.

In one aspect, the present invention relates to a composition comprising: a plurality of substantially purified megakaryocyte-derived extracellular vesicles comprising a lipid bilayer membrane surrounding a lumen and the lipid bilayer membrane comprises one or more proteins associated with or embedded within. In some embodiments, the megakaryocyte-derived extracellular vesicles are derived from a human pluripotent stem cell. In some embodiments, the megakaryocyte-derived extracellular vesicle lumen comprises one or more megakaryocyte-derived nucleic acid molecules selected from mRNA, tRNA, rRNA, siRNA, microRNA, regulating RNA, and non-coding and coding RNA. In some embodiments, the megakaryocyte-derived extracellular vesicles comprise cargo suitable for gene editing the cell and/or cargo associated with the surface of the megakaryocyte-derived extracellular vesicles. In some embodiments, in addition to or as an alternative to the cargo located in the lumen of the megakaryocyte-derived extracellular vesicles, the cargo is loaded into the megakaryocyte for packaging into the extracellular vesicles. In some embodiments, in addition to or as an alternative to the cargo located in the lumen of the megakaryocyte-derived extracellular vesicles, the cargo is loaded directly into the meg akaryocyte-derived extracellular vesicles.

In another aspect, the present invention relates to a composition comprising: a plurality of substantially purified megakaryocyte-derived extracellular vesicles comprising a lipid bilayer membrane surrounding a lumen and the lipid bilayer membrane comprises one or more proteins associated with or embedded within. In some embodiments, the megakaryocyte-derived extracellular vesicles are derived from a human pluripotent stem cell. In some embodiments, the megakaryocyte-derived extracellular vesicle comprises one or more nucleic acid molecules selected from mRNA, tRNA, rRNA, siRNA, microRNA, regulating RNA, and non-coding and coding RNA associated with the surface of the vesicle, and the lipid bilayer membrane comprises one or more proteins associated with or embedded within. In some embodiments, the nucleic acid molecule is exogenously derived. In some embodiments, the megakaryocyte-derived extracellular vesicles comprise cargo suitable for gene editing the cell and/or cargo associated with the surface of the megakaryocyte-derived extracellular vesicles. In some embodiments, in addition to or as an alternative to the cargo located in the lumen of the megakaryocyte-derived extracellular vesicles, the cargo is loaded into the megakaryocyte for packaging into the extracellular vesicles. In some embodiments, in addition to or as an alternative to the cargo located in the lumen of the megakaryocyte-derived extracellular vesicles, the cargo is loaded directly into the mega-karyocyte-derived extracellular vesicles.

In one aspect, the present invention relates to a composition comprising: a plurality of substantially purified mega-karyocyte-derived extracellular vesicles comprising a lipid bilayer membrane surrounding a lumen and the lipid bilayer membrane comprises one or more proteins associated with or embedded within. In some embodiments, the megakaryo-cyte-derived extracellular vesicles are derived from a human pluripotent stem cell. In some embodiments, the megakaryo-cyte-derived extracellular vesicles are suitable for loading with cargo into the lumen. In some embodiments, the cargo comprises one or more agent. In some embodiments, the agent is one or more therapeutic agents, including therapeu-tic agents described herein. In some embodiments, the cargo comprises one or more megakaryocyte-derived nucleic acid molecules selected from mRNA, tRNA, rRNA, siRNA, microRNA, regulating RNA, and non-coding and coding RNA. In some embodiments, in addition to or as an alter-native to the cargo located in the lumen of the megakaryo-cyte-derived extracellular vesicles, the cargo is loaded into the megakaryocyte for packaging into the extracellular vesicles. In some embodiments, in addition to or as an alternative to the cargo located in the lumen of the mega-karyocyte-derived extracellular vesicles, the cargo is loaded directly into the megakaryocyte-derived extracellular vesicles. In some embodiments, the megakaryocyte-derived extracellular vesicles are suitable for loading with cargo associated with the surface of the megakaryocyte-derived extracellular vesicles.

In another aspect, the present invention relates to a composition comprising: a plurality of substantially purified megakaryocyte-derived extracellular vesicles comprising a lipid bilayer membrane surrounding a lumen and derived from a human pluripotent stem cell, wherein: the mega-karyocyte-derived extracellular vesicle lumen comprises cargo and the lipid bilayer membrane comprises one or more proteins associated with or embedded within. In some embodiments, the cargo comprises one or more agents. In some embodiments, the agent is one or more therapeutic agents, including therapeutic agents described herein. In some embodiments, the cargo comprises one or more mega-karyocyte-derived nucleic acid molecules selected from mRNA, tRNA, rRNA, siRNA, microRNA, regulating RNA, and non-coding and coding RNA. In some embodiments, in addition to or as an alternative to the cargo located in the lumen of the megakaryocyte-derived extracellular vesicles, the cargo is loaded into the megakaryocyte for packaging into the extracellular vesicles. In some embodiments, in addition to or as an alternative to the cargo located in the lumen of the megakaryocyte-derived extracellular vesicles, the cargo is loaded directly into the megakaryocyte-derived extracellular vesicles. In some embodiments, the mega-karyocyte-derived extracellular vesicles are suitable for loading with cargo associated with the surface of the mega-karyocyte-derived extracellular vesicles.

In one aspect, the present invention relates to a compo-sition comprising: a plurality of substantially purified mega-karyocyte-derived extracellular vesicles comprising a lipid bilayer membrane surrounding a lumen and derived from a human pluripotent stem cell, wherein: the megakaryocyte-derived extracellular vesicle lumen comprises one or more megakaryocyte-derived nucleic acid molecules selected from mRNA, tRNA, rRNA, siRNA, microRNA, regulating RNA, and non-coding and coding RNA and the lipid bilayer membrane comprises one or more proteins associated with or embedded within.

In another aspect, the present invention relates to a pharmaceutical composition comprising a composition com-prising megakaryocyte-derived extracellular vesicles and/or a plurality of megakaryocyte-derived extracellular vesicles disclosed herein and a pharmaceutically acceptable excipi-ent or carrier.

In another aspect, the present invention relates to a method for transferring a deliverable therapeutic agent, comprising: (a) obtaining the megakaryocyte-derived extra-cellular vesicles of a composition comprising megakaryo-cyte-derived extracellular vesicles and/or a plurality of megakaryocyte-derived extracellular vesicles disclosed herein; (b) incubating the megakaryocyte-derived extracel-lular vesicle with a therapeutic agent to allow the therapeutic agent to populate the lumen of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient.

In another aspect, the present invention relates to a method for transferring a deliverable therapeutic agent, comprising: (a) obtaining the megakaryocyte-derived extra-cellular vesicles disclosed herein; (b) incubating the mega-karyocyte-derived extracellular vesicle with a therapeutic agent to allow the therapeutic agent to populate the lumen of the megakaryocyte-derived extracellular vesicle and/or associate with the surface of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient.

In another aspect, the present invention relates to a method of generating the megakaryocyte-derived extracel-lular vesicles disclosed herein, comprising: (a) obtaining a human pluripotent stem cell, the human pluripotent stem cell being a primary CD34+ hematopoietic stem cell sourced from peripheral blood or cord blood or bone marrow; (b) differentiating the human pluripotent stem cell to a mega-karyocyte in the absence of added erythropoietin and in the presence of added thrombopoietin; and (c) isolating mega-karyocyte-derived extracellular vesicles from the mega-karyocytes.

In another aspect, the present invention relates to a method for treating a myeloproliferative disease or disor-ders, such as MPN, with the present megakaryocyte-derived extracellular vesicles.

Biomarker Profile or Fingerprint

In various embodiments, the megakaryocyte-derived extracellular vesicles of the disclosure are characterized by a unique biomarker profile or fingerprint that distinguishes them from, for instance, naturally-occurring megakaryo-cyte-derived extracellular vesicles and/or vesicles or extra-cellular vesicles derived from platelets. In various embodi-ments, the present megakaryocyte-derived extracellular vesicles are characterized by a such a biomarker profile or fingerprint, which comprises the identity (e.g. the presence or absence) or amount (e.g. substantial presence or substan-tial absence of a biomarker in a megakaryocyte-derived extracellular vesicle population; or presence on or absence from a majority of megakaryocyte-derived extracellular vesicle in a population; or percentage megakaryocyte-de-rived extracellular vesicles having a biomarker).

In some embodiments, the substantially purified mega-karyocyte-derived extracellular vesicles comprise a lipid bilayer membrane surrounding a lumen and derived from a human pluripotent stem cell, wherein the lipid bilayer membrane comprises one or more proteins (a.k.a. biomarkers) associated with or embedded within.

In some embodiments, the substantially purified megakaryocyte-derived extracellular vesicles comprise a lipid bilayer membrane surrounding a lumen, wherein the lipid bilayer membrane comprises one or more proteins (a.k.a. biomarkers) associated with or embedded within. In some embodiments, the megakaryocyte-derived extracellular vesicles are derived from a human pluripotent stem cell.

In embodiments, the lipid bilayer membrane comprises proteins selected from CD54, CD18, CD43, CD11b, CD62P, CD41, CD61, CD21, CD51, phosphatidylserine (PS), CLEC-2, LAMP-1 (CD107a), CD63, CD42b, CD9, CD31, CD47, CD147, CD32a, and GPVI.

In embodiments, the lipid bilayer membrane comprises phosphatidylserine, e.g., without limitation by testing for Annexin V.

In embodiments, the lipid bilayer membrane comprises one or more proteins selected from CD62P, CD41, and CD61.

In embodiments, greater than about 40%, greater than about 50%, greater than about 60%, greater than about 70%, greater than about 80%, greater than about 90%, greater than about 95%, or greater than about 99% of the megakaryocyte-derived extracellular vesicles comprising a lipid bilayer membrane comprising CD41 also comprise CD61 in the lipid bilayer membrane.

In embodiments, the present megakaryocyte-derived extracellular vesicles are characterized by the expression and/or presence of one or more of CD54, CD18, CD43, CD11b, CD62P, CD41, CD61, CD21, CD51, and CLEC-2. In embodiments, the present megakaryocyte-derived extracellular vesicles are characterized by the expression and/or presence of one or more of PS, CD62P, LAMP-1 (CD107a), CD42b, CD9, CD43, CD31, and CD11b. In embodiments, the present megakaryocyte-derived extracellular vesicles are characterized by the expression and/or presence of one or more of PS, CD61, CD62P, LAMP-1 (CD107a), CLEC-2, and CD63. In embodiments, the present megakaryocyte-derived extracellular vesicles are characterized by the expression and/or presence of one or more of PS, CD62P, CLEC-2, CD9, CD31, CD147, CD32a, and GPVI. In embodiments, the present megakaryocyte-derived extracellular vesicles are characterized by the expression and/or presence of one or more of PS, CD62P, LAMP-1 (CD107a), CLEC-2, CD9, and CD31. In embodiments, the present megakaryocyte-derived extracellular vesicles are characterized by the expression and/or presence of one or more of CD62P, CD41, and CD61. In embodiments, the present megakaryocyte-derived extracellular vesicles are characterized by a substantial expression and/or presence of one or more of CD54, CD18, CD43, CD11b, CD62P, CD41, CD61, CD21, CD51, and CLEC-2. In embodiments, the present megakaryocyte-derived extracellular vesicles are characterized by a substantial expression and/or presence of one or more of CD62P, CD41, and CD61. In some embodiments, the present megakaryocyte-derived extracellular vesicles are characterized by not expressing and/or comprising a substantial amount of DRAQ5. In some embodiments, the present megakaryocyte-derived extracellular vesicles are characterized by being substantially free of DRAQ5.

In embodiments, greater than about 50% of the megakaryocyte-derived extracellular vesicles comprise a lipid bilayer membrane comprising CD62P. In some embodiments, greater than about 40% of the megakaryocyte-derived extracellular vesicles comprise a lipid bilayer membrane comprising CD62P. In some embodiments, greater than about 60% of the megakaryocyte-derived extracellular vesicles comprise a lipid bilayer membrane comprising CD62P. In some embodiments, greater than about 70% of the megakaryocyte-derived extracellular vesicles comprise a lipid bilayer membrane comprising CD62P. In some embodiments, greater than about 80% of the megakaryocyte-derived extracellular vesicles comprise a lipid bilayer membrane comprising CD62P. In some embodiments, greater than about 90% of the megakaryocyte-derived extracellular vesicles comprise a lipid bilayer membrane comprising CD62P. In some embodiments, greater than about 95% of the megakaryocyte-derived extracellular vesicles comprise a lipid bilayer membrane comprising CD62P. In some embodiments, greater than about 99% of the megakaryocyte-derived extracellular vesicles comprise a lipid bilayer membrane comprising CD62P.

In embodiments, about 50% or less of the megakaryocyte-derived extracellular vesicles comprise a lipid bilayer membrane comprising CD62P. In some embodiments, about 40% or less of the megakaryocyte-derived extracellular vesicles comprise a lipid bilayer membrane comprising CD62P. In some embodiments, about 60% or less of the megakaryocyte-derived extracellular vesicles comprise a lipid bilayer membrane comprising CD62P. In some embodiments, about 70% or less of the megakaryocyte-derived extracellular vesicles comprise a lipid bilayer membrane comprising CD62P. In some embodiments, about 80% or less of the megakaryocyte-derived extracellular vesicles comprise a lipid bilayer membrane comprising CD62P. In some embodiments, about 90% or less of the megakaryocyte-derived extracellular vesicles comprise a lipid bilayer membrane comprising CD62P. In some embodiments, about 95% or less of the megakaryocyte-derived extracellular vesicles comprise a lipid bilayer membrane comprising CD62P. In some embodiments, about 99% or less of the megakaryocyte-derived extracellular vesicles comprise a lipid bilayer membrane comprising CD62P.

In some embodiments, less than about 50% of the megakaryocyte-derived extracellular vesicles comprise a lipid bilayer membrane comprising CD62P. In embodiments, less than about 40% of the megakaryocyte-derived extracellular vesicles comprise a lipid bilayer membrane comprising CD62P. In some embodiments, less than about 30% of the megakaryocyte-derived extracellular vesicles comprise a lipid bilayer membrane comprising CD62P. In some embodiments, less than about 25% of the megakaryocyte-derived extracellular vesicles comprise a lipid bilayer membrane comprising CD62P. In some embodiments, less than about 20% of the megakaryocyte-derived extracellular vesicles comprise a lipid bilayer membrane comprising CD62P. In some embodiments, less than about 15% of the megakaryocyte-derived extracellular vesicles comprise a lipid bilayer membrane comprising CD62P. In some embodiments, less than about 10% of the megakaryocyte-derived extracellular vesicles comprise a lipid bilayer membrane comprising CD62P. In some embodiments, less than about 5% of the megakaryocyte-derived extracellular vesicles comprise a lipid bilayer membrane comprising CD62P. In some embodiments, less than about 1% of the megakaryocyte-derived extracellular vesicles comprise a lipid bilayer membrane comprising CD62P.

In some embodiments, between about 1% to about 99% of the megakaryocyte-derived extracellular vesicles comprise a lipid bilayer membrane comprising CD62P. In some embodiments, between about 1% to about 50% of the megakaryocyte-derived extracellular vesicles comprise a lipid bilayer membrane comprising CD62P. In some embodiments, between about 1% to about 25% of the megakaryocyte-derived extracellular vesicles comprise a lipid bilayer membrane comprising CD62P. In some embodiments, between about 1% to about 10% of the megakaryocyte-derived extracellular vesicles comprise a lipid bilayer membrane comprising CD62P. In some embodiments, between about 1% to about 5% of the mega-karyocyte-derived extracellular vesicles comprise a lipid bilayer membrane comprising CD62P. In some embodi-ments, between about 1% to about 2% of the megakaryo-cyte-derived extracellular vesicles comprise a lipid bilayer membrane comprising CD62P. In some embodiments, between about 50% to about 99% of the megakaryocyte-derived extracellular vesicles comprise a lipid bilayer mem-brane comprising CD62P. In some embodiments, between about 75% to about 99% of the megakaryocyte-derived extracellular vesicles comprise a lipid bilayer membrane comprising CD62P. In some embodiments, between about 90% to about 99% of the megakaryocyte-derived extracel-lular vesicles comprise a lipid bilayer membrane comprising CD62P. In some embodiments, between about 95% to about 99% of the megakaryocyte-derived extracellular vesicles comprise a lipid bilayer membrane comprising CD62P.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD62P.

In embodiments, the megakaryocyte-derived extracellular vesicles are free of, or substantially free of CD62P.

In embodiments, the megakaryocyte-derived extracellular vesicles of the disclosure are characterized by a higher expression and/or presence of CD62P than naturally-occur-ring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracel-lular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD62P than naturally-occurring megakaryocyte-derived extracellular vesicles, vesicles or extracellular vesicles derived from platelets such as platelet derived extracellular vesicles (PLT EVs), and/or platelet-free plasma (PPF) mega-karyocyte-derived extracellular vesicles.

In embodiments, the megakaryocyte-derived extracellular vesicles of the disclosure are characterized by a lower expression and/or presence of CD62P than naturally-occur-ring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracel-lular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD62P than naturally-occurring megakaryocyte-derived extracellular vesicles, vesicles or extracellular vesicles derived from platelets such as platelet derived extracellular vesicles (PLT EVs), and/or platelet-free plasma (PPF) mega-karyocyte-derived extracellular vesicles.

In embodiments, the megakaryocyte-derived extracellular vesicles have about a 4-fold to about a 32-fold or about an 8-fold to about a 16-fold lower amount of CD62P than platelet free plasma (PFP) MkEVs. In embodiments, the megakaryocyte-derived extracellular vesicles have about a 15-fold or about a 16-fold lower amount of CD62P than platelet free plasma (PFP) MkEVs. In embodiments, the megakaryocyte-derived extracellular vesicles have about a 32-fold to about a 128-fold, about a 50-fold to about a 75-fold, or about a 60-fold to about a 70-fold lower amount of CD62P than platelet derived extracellular vesicles (PLT EVs). In embodiments, the megakaryocyte-derived extra-cellular vesicles have about a 60-fold, about a 64-fold, or about a 70-fold lower amount of CD62P than platelet derived extracellular vesicles (PLT EVs).

In embodiments, greater than about 50% of the mega-karyocyte-derived extracellular vesicles comprise a lipid bilayer membrane comprising CD41. In some embodiments, greater than about 40% of the megakaryocyte-derived extra-cellular vesicles comprise a lipid bilayer membrane com-prising CD41. In some embodiments, greater than about 60% of the megakaryocyte-derived extracellular vesicles comprise a lipid bilayer membrane comprising CD41. In some embodiments, greater than about 70% of the mega-karyocyte-derived extracellular vesicles comprise a lipid bilayer membrane comprising CD41. In some embodiments, greater than about 80% of the megakaryocyte-derived extra-cellular vesicles comprise a lipid bilayer membrane com-prising CD41. In some embodiments, greater than about 90% of the megakaryocyte-derived extracellular vesicles comprise a lipid bilayer membrane comprising CD41. In some embodiments, greater than about 95% of the mega-karyocyte-derived extracellular vesicles comprise a lipid bilayer membrane comprising CD41. In some embodiments, greater than about 99% of the megakaryocyte-derived extra-cellular vesicles comprise a lipid bilayer membrane com-prising CD41.

In embodiments, about 50% or less of the megakaryocyte-derived extracellular vesicles comprise a lipid bilayer mem-brane comprising CD41. In some embodiments, about 40% or less of the megakaryocyte-derived extracellular vesicles comprise a lipid bilayer membrane comprising CD41. In some embodiments, about 60% or less of the megakaryo-cyte-derived extracellular vesicles comprise a lipid bilayer membrane comprising CD41. In some embodiments, about 70% or less of the megakaryocyte-derived extracellular vesicles comprise a lipid bilayer membrane comprising CD41. In some embodiments, about 80% or less of the megakaryocyte-derived extracellular vesicles comprise a lipid bilayer membrane comprising CD41. In some embodi-ments, about 90% or less of the megakaryocyte-derived extracellular vesicles comprise a lipid bilayer membrane comprising CD41. In some embodiments, about 95% or less of the megakaryocyte-derived extracellular vesicles comprise a lipid bilayer membrane comprising CD41. In some embodiments, about 99% or less of the megakaryocyte-derived extracellular vesicles comprise a lipid bilayer membrane comprising CD41.

In some embodiments, less than about 50% of the megakaryocyte-derived extracellular vesicles comprise a lipid bilayer membrane comprising CD41. In embodiments, less than about 40% of the megakaryocyte-derived extracellular vesicles comprise a lipid bilayer membrane comprising CD41. In some embodiments, less than about 30% of the megakaryocyte-derived extracellular vesicles comprise a lipid bilayer membrane comprising CD41. In some embodiments, less than about 25% of the megakaryocyte-derived extracellular vesicles comprise a lipid bilayer membrane comprising CD41. In some embodiments, less than about 20% of the megakaryocyte-derived extracellular vesicles comprise a lipid bilayer membrane comprising CD41. In some embodiments, less than about 15% of the megakaryocyte-derived extracellular vesicles comprise a lipid bilayer membrane comprising CD41. In some embodiments, less than about 10% of the megakaryocyte-derived extracellular vesicles comprise a lipid bilayer membrane comprising CD41. In some embodiments, less than about 5% of the megakaryocyte-derived extracellular vesicles comprise a lipid bilayer membrane comprising CD41. In some embodiments, less than about 1% of the megakaryocyte-derived extracellular vesicles comprise a lipid bilayer membrane comprising CD41.

In some embodiments, between about 1% to about 99% of the megakaryocyte-derived extracellular vesicles comprise a lipid bilayer membrane comprising CD41. In some embodiments, between about 1% to about 50% of the megakaryocyte-derived extracellular vesicles comprise a lipid bilayer membrane comprising CD41. In some embodiments, between about 1% to about 25% of the megakaryocyte-derived extracellular vesicles comprise a lipid bilayer membrane comprising CD41. In some embodiments, between about 1% to about 10% of the megakaryocyte-derived extracellular vesicles comprise a lipid bilayer membrane comprising CD41. In some embodiments, between about 1% to about 5% of the megakaryocyte-derived extracellular vesicles comprise a lipid bilayer membrane comprising CD41. In some embodiments, between about 1% to about 2% of the megakaryocyte-derived extracellular vesicles comprise a lipid bilayer membrane comprising CD41. In some embodiments, between about 50% to about 99% of the megakaryocyte-derived extracellular vesicles comprise a lipid bilayer membrane comprising CD41. In some embodiments, between about 75% to about 99% of the megakaryocyte-derived extracellular vesicles comprise a lipid bilayer membrane comprising CD41. In some embodiments, between about 90% to about 99% of the megakaryocyte-derived extracellular vesicles comprise a lipid bilayer membrane comprising CD41. In some embodiments, between about 95% to about 99% of the megakaryocyte-derived extracellular vesicles comprise a lipid bilayer membrane comprising CD41.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD41.

In embodiments, the megakaryocyte-derived extracellular vesicles comprise CD41.

In embodiments, the megakaryocyte-derived extracellular vesicles are characterized by a higher expression and/or presence or CD41 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD41 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence or CD41 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD41 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold or about a 2-fold to about a 4-fold greater amount of CD41/CD61 than platelet free plasma (PFP) MkEVs. In embodiments, the megakaryocyte-derived extracellular vesicles have about a 2-fold, about a 3-fold, or about a 4-fold greater amount of CD41/CD61 than platelet free plasma (PFP) MkEVs. In embodiments, the megakaryocyte-derived extracellular vesicles have about a 1.1-fold to about a 2-fold greater amount of CD41/CD61 than platelet derived extracellular vesicles (PLT EVs). In embodiments, the megakaryocyte-derived extracellular vesicles have about a 1.1-fold or about a 1.2-fold greater amount of CD41/CD61 than platelet derived extracellular vesicles (PLT EVs). In embodiments, the megakaryocyte-derived extracellular vesicles have an amount of CD41/CD61 that is substantially the same as platelet derived extracellular vesicles (PLT EVs).

In embodiments, greater than about 50% of the megakaryocyte-derived extracellular vesicles comprise a lipid bilayer membrane comprising CD61. In some embodiments, greater than about 40% of the megakaryocyte-derived extracellular vesicles comprise a lipid bilayer membrane comprising CD61. In some embodiments, greater than about 60% of the megakaryocyte-derived extracellular vesicles comprise a lipid bilayer membrane comprising CD61. In some embodiments, greater than about 70% of the megakaryocyte-derived extracellular vesicles comprise a lipid bilayer membrane comprising CD61. In some embodiments, greater than about 80% of the megakaryocyte-derived extracellular vesicles comprise a lipid bilayer membrane comprising CD61. In some embodiments, greater than about 90% of the megakaryocyte-derived extracellular vesicles comprise a lipid bilayer membrane comprising CD61. In some embodiments, greater than about 95% of the megakaryocyte-derived extracellular vesicles comprise a lipid bilayer membrane comprising CD61. In some embodiments, greater than about 99% of the megakaryocyte-derived extracellular vesicles comprise a lipid bilayer membrane comprising CD61.

In embodiments, about 50% or less of the megakaryocyte-derived extracellular vesicles comprise a lipid bilayer membrane comprising CD61. In some embodiments, less than about 40% of the megakaryocyte-derived extracellular vesicles comprise a lipid bilayer membrane comprising CD61. In some embodiments, about 60% or less of the megakaryocyte-derived extracellular vesicles comprise a lipid bilayer membrane comprising CD61. In some embodiments, about 70% or less of the megakaryocyte-derived extracellular vesicles comprise a lipid bilayer membrane comprising CD61. In some embodiments, about 80% or less of the megakaryocyte-derived extracellular vesicles comprise a lipid bilayer membrane comprising CD61. In some embodiments, less than about 90% of the megakaryocyte-derived extracellular vesicles comprise a lipid bilayer membrane comprising CD61. In some embodiments, about 95% or less of the megakaryocyte-derived extracellular vesicles comprise a lipid bilayer membrane comprising CD61. In some embodiments, about 99% or less of the megakaryocyte-derived extracellular vesicles comprise a lipid bilayer membrane comprising CD61.

In some embodiments, less than about 50% of the megakaryocyte-derived extracellular vesicles comprise a lipid bilayer membrane comprising CD61. In embodiments, less than about 40% of the megakaryocyte-derived extracellular vesicles comprise a lipid bilayer membrane comprising CD61. In some embodiments, less than about 30% of the megakaryocyte-derived extracellular vesicles comprise a lipid bilayer membrane comprising CD61. In some embodiments, less than about 25% of the megakaryocyte-derived extracellular vesicles comprise a lipid bilayer membrane comprising CD61. In some embodiments, less than about 20% of the megakaryocyte-derived extracellular vesicles comprise a lipid bilayer membrane comprising CD61. In some embodiments, less than about 15% of the megakaryocyte-derived extracellular vesicles comprise a lipid bilayer membrane comprising CD61. In some embodiments, less than about 10% of the megakaryocyte-derived extracellular vesicles comprise a lipid bilayer membrane comprising CD61. In some embodiments, less than about 5% of the megakaryocyte-derived extracellular vesicles comprise a lipid bilayer membrane comprising CD61. In some embodiments, less than about 1% of the megakaryocyte-derived extracellular vesicles comprise a lipid bilayer membrane comprising CD61.

In some embodiments, between about 1% to about 99% of the megakaryocyte-derived extracellular vesicles comprise a lipid bilayer membrane comprising CD61. In some embodiments, between about 1% to about 50% of the megakaryocyte-derived extracellular vesicles comprise a lipid bilayer membrane comprising CD61. In some embodiments, between about 1% to about 25% of the megakaryocyte-derived extracellular vesicles comprise a lipid bilayer membrane comprising CD61. In some embodiments, between about 1% to about 10% of the megakaryocyte-derived extracellular vesicles comprise a lipid bilayer membrane comprising CD61. In some embodiments, between about 1% to about 5% of the megakaryocyte-derived extracellular vesicles comprise a lipid bilayer membrane comprising CD61. In some embodiments, between about 1% to about 2% of the megakaryocyte-derived extracellular vesicles comprise a lipid bilayer membrane comprising CD61. In some embodiments, between about 50% to about 99% of the megakaryocyte-derived extracellular vesicles comprise a lipid bilayer membrane comprising CD61. In some embodiments, between about 75% to about 99% of the megakaryocyte-derived extracellular vesicles comprise a lipid bilayer membrane comprising CD61. In some embodiments, between about 80% to about 99% of the megakaryocyte-derived extracellular vesicles comprise a lipid bilayer membrane comprising CD61. In some embodiments, between about 85% to about 95% of the megakaryocyte-derived extracellular vesicles comprise a lipid bilayer membrane comprising CD61. In some embodiments, between about 90% to about 99% of the megakaryocyte-derived extracellular vesicles comprise a lipid bilayer membrane comprising CD61. In some embodiments, between about 95% to about 99% of the megakaryocyte-derived extracellular vesicles comprise a lipid bilayer membrane comprising CD61.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD61.

In embodiments, the megakaryocyte-derived extracellular vesicles are characterized by a higher expression and/or presence of CD61 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD61 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD61 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD61 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold or about a 2-fold to about a 4-fold greater amount of CD61 than platelet free plasma (PFP) MkEVs. In embodiments, the megakaryocyte-derived extracellular vesicles have about a 2-fold, about a 3-fold, or about a 4-fold greater amount of CD61 than platelet free plasma (PFP) MkEVs. In embodiments, the megakaryocyte-derived extracellular vesicles have about a 1.1-fold to about a 2-fold lower amount of CD61 than platelet derived extracellular vesicles (PLT EVs). In embodiments, the megakaryocyte-derived extracellular vesicles have about a 1.1-fold or about a 1.2-fold lower amount of CD61 than platelet derived extracellular vesicles (PLT EVs). In embodiments, the megakaryocyte-derived extracellular vesicles have an amount of CD61 that is substantially the same as platelet derived extracellular vesicles (PLT EVs).

In embodiments, greater than about 50% of the megakaryocyte-derived extracellular vesicles comprise a lipid bilayer membrane comprising CD54. In some embodiments, greater than about 40% of the megakaryocyte-derived extracellular vesicles comprise a lipid bilayer membrane comprising CD54. In some embodiments, greater than about 60% of the megakaryocyte-derived extracellular vesicles comprise a lipid bilayer membrane comprising CD54. In some embodiments, greater than about 70% of the megakaryocyte-derived extracellular vesicles comprise a lipid bilayer membrane comprising CD4. In some embodiments, greater than about 80% of the megakaryocyte-derived extracellular vesicles comprise a lipid bilayer membrane comprising CD54. In some embodiments, greater than about 90% of the megakaryocyte-derived extracellular vesicles comprise a lipid bilayer membrane comprising CD54.

In some embodiments, greater than about 95% of the megakaryocyte-derived extracellular vesicles comprise a lipid bilayer membrane comprising CD54. In some embodiments, greater than about 99% of the megakaryocyte-derived extracellular vesicles comprise a lipid bilayer membrane comprising CD54.

In embodiments, about 50% or less of the megakaryocyte-derived extracellular vesicles comprise a lipid bilayer membrane comprising CD54. In some embodiments, about 40% or less of the megakaryocyte-derived extracellular vesicles comprise a lipid bilayer membrane comprising CD54. In some embodiments, about 60% or less of the megakaryocyte-derived extracellular vesicles comprise a lipid bilayer membrane comprising CD54. In some embodiments, about 70% or less of the megakaryocyte-derived extracellular vesicles comprise a lipid bilayer membrane comprising CD54. In some embodiments, about 80% or less of the megakaryocyte-derived extracellular vesicles comprise a lipid bilayer membrane comprising CD54. In some embodiments, about 90% or less of the megakaryocyte-derived extracellular vesicles comprise a lipid bilayer membrane comprising CD54. In some embodiments, about 95% or less of the megakaryocyte-derived extracellular vesicles comprise a lipid bilayer membrane comprising CD54. In some embodiments, about 99% or less of the megakaryocyte-derived extracellular vesicles comprise a lipid bilayer membrane comprising CD54.

In some embodiments, less than about 50% of the megakaryocyte-derived extracellular vesicles comprise a lipid bilayer membrane comprising CD54. In embodiments, less than about 40% of the megakaryocyte-derived extracellular vesicles comprise a lipid bilayer membrane comprising CD54. In some embodiments, less than about 30% of the megakaryocyte-derived extracellular vesicles comprise a lipid bilayer membrane comprising CD54. In some embodiments, less than about 25% of the megakaryocyte-derived extracellular vesicles comprise a lipid bilayer membrane comprising CD54. In some embodiments, less than about 20% of the megakaryocyte-derived extracellular vesicles comprise a lipid bilayer membrane comprising CD54. In some embodiments, less than about 15% of the megakaryocyte-derived extracellular vesicles comprise a lipid bilayer membrane comprising CD54. In some embodiments, less than about 10% of the megakaryocyte-derived extracellular vesicles comprise a lipid bilayer membrane comprising CD54. In some embodiments, less than about 5% of the megakaryocyte-derived extracellular vesicles comprise a lipid bilayer membrane comprising CD54. In some embodiments, less than about 1% of the megakaryocyte-derived extracellular vesicles comprise a lipid bilayer membrane comprising CD54.

In some embodiments, between about 1% to about 99% of the megakaryocyte-derived extracellular vesicles comprise a lipid bilayer membrane comprising CD54. In some embodiments, between about 1% to about 50% of the megakaryocyte-derived extracellular vesicles comprise a lipid bilayer membrane comprising CD54. In some embodiments, between about 1% to about 25% of the megakaryocyte-derived extracellular vesicles comprise a lipid bilayer membrane comprising CD54. In some embodiments, between about 1% to about 10% of the megakaryocyte-derived extracellular vesicles comprise a lipid bilayer membrane comprising CD54. In some embodiments, between about 1% to about 5% of the megakaryocyte-derived extracellular vesicles comprise a lipid bilayer membrane comprising CD54. In some embodiments, between about 1% to about 2% of the megakaryocyte-derived extracellular vesicles comprise a lipid bilayer membrane comprising CD54. In some embodiments, between about 50% to about 99% of the megakaryocyte-derived extracellular vesicles comprise a lipid bilayer membrane comprising CD54. In some embodiments, between about 75% to about 99% of the megakaryocyte-derived extracellular vesicles comprise a lipid bilayer membrane comprising CD54. In some embodiments, between about 90% to about 99% of the megakaryocyte-derived extracellular vesicles comprise a lipid bilayer membrane comprising CD54. In some embodiments, between about 95% to about 99% of the megakaryocyte-derived extracellular vesicles comprise a lipid bilayer membrane comprising CD54.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD54.

In embodiments, the megakaryocyte-derived extracellular vesicles are characterized by a higher expression and/or presence of CD54 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD54 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about a 10-fold or about a 2-fold to about a 4-fold greater amount of CD54 than platelet free plasma (PFP) MkEVs. In embodiments, the megakaryocyte-derived extracellular vesicles have about a 3-fold greater amount of CD54 than platelet free plasma (PFP) MkEVs. In embodiments, the megakaryocyte-derived extracellular vesicles have about a 1.1-fold to about a 4-fold or about a 1.1-fold to about a 2-fold greater amount of CD54 than platelet derived extracellular vesicles (PLT EVs). In embodiments, the megakaryocyte-derived extracellular vesicles have about a 1.5-fold greater amount of CD54 than platelet derived extracellular vesicles (PLT EVs).

In embodiments, the megakaryocyte-derived extracellular vesicles are characterized by a lower expression and/or presence of CD54 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD54 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the megakaryocyte-derived extracellular vesicles comprise a lipid bilayer membrane comprising CD18. In some embodiments, greater than about 40% of the megakaryocyte-derived extracellular vesicles comprise a lipid bilayer membrane comprising CD18. In some embodiments, greater than about 60% of the megakaryocyte-derived extracellular vesicles comprise a lipid bilayer membrane comprising CD18. In some embodiments, greater than about 70% of the megakaryocyte-derived extracellular vesicles comprise a lipid bilayer membrane comprising CD18. In some embodiments, greater than about 80% of the megakaryocyte-derived extracellular vesicles comprise a lipid bilayer membrane comprising CD18. In some embodiments, greater than about 90% of the megakaryocyte-derived extracellular vesicles comprise a lipid bilayer membrane comprising CD18.

In some embodiments, greater than about 95% of the megakaryocyte-derived extracellular vesicles comprise a lipid bilayer membrane comprising CD18. In some embodiments, greater than about 99% of the megakaryocyte-derived extracellular vesicles comprise a lipid bilayer membrane comprising CD18.

In embodiments, about 50% or less of the megakaryocyte-derived extracellular vesicles comprise a lipid bilayer membrane comprising CD18. In some embodiments, about 40% or less of the megakaryocyte-derived extracellular vesicles comprise a lipid bilayer membrane comprising CD18. In some embodiments, about 60% or less of the megakaryocyte-derived extracellular vesicles comprise a lipid bilayer membrane comprising CD18. In some embodiments, about 70% or less of the megakaryocyte-derived extracellular vesicles comprise a lipid bilayer membrane comprising CD18. In some embodiments, about 80% or less of the megakaryocyte-derived extracellular vesicles comprise a lipid bilayer membrane comprising CD18. In some embodiments, about 90% or less of the megakaryocyte-derived extracellular vesicles comprise a lipid bilayer membrane comprising CD18. In some embodiments, about 95% or less of the megakaryocyte-derived extracellular vesicles comprise a lipid bilayer membrane comprising CD18. In some embodiments, about 99% or less of the megakaryocyte-derived extracellular vesicles comprise a lipid bilayer membrane comprising CD18.

In some embodiments, less than about 50% of the megakaryocyte-derived extracellular vesicles comprise a lipid bilayer membrane comprising CD18. In embodiments, less than about 40% of the megakaryocyte-derived extracellular vesicles comprise a lipid bilayer membrane comprising CD18. In some embodiments, less than about 30% of the megakaryocyte-derived extracellular vesicles comprise a lipid bilayer membrane comprising CD18. In some embodiments, less than about 25% of the megakaryocyte-derived extracellular vesicles comprise a lipid bilayer membrane comprising CD18. In some embodiments, less than about 20% of the megakaryocyte-derived extracellular vesicles comprise a lipid bilayer membrane comprising CD18. In some embodiments, less than about 15% of the megakaryocyte-derived extracellular vesicles comprise a lipid bilayer membrane comprising CD18. In some embodiments, less than about 10% of the megakaryocyte-derived extracellular vesicles comprise a lipid bilayer membrane comprising CD18. In some embodiments, less than about 5% of the megakaryocyte-derived extracellular vesicles comprise a lipid bilayer membrane comprising CD18. In some embodiments, less than about 1% of the megakaryocyte-derived extracellular vesicles comprise a lipid bilayer membrane comprising CD18.

In some embodiments, between about 1% to about 99% of the megakaryocyte-derived extracellular vesicles comprise a lipid bilayer membrane comprising CD18. In some embodiments, between about 1% to about 50% of the megakaryocyte-derived extracellular vesicles comprise a lipid bilayer membrane comprising CD18. In some embodiments, between about 1% to about 25% of the megakaryocyte-derived extracellular vesicles comprise a lipid bilayer membrane comprising CD18. In some embodiments, between about 1% to about 10% of the megakaryocyte-derived extracellular vesicles comprise a lipid bilayer membrane comprising CD18. In some embodiments, between about 1% to about 5% of the megakaryocyte-derived extracellular vesicles comprise a lipid bilayer membrane comprising CD18. In some embodiments, between about 1% to about 2% of the megakaryocyte-derived extracellular vesicles comprise a lipid bilayer membrane comprising CD18. In some embodiments, between about 50% to about 99% of the megakaryocyte-derived extracellular vesicles comprise a lipid bilayer membrane comprising CD18. In some embodiments, between about 75% to about 99% of the megakaryocyte-derived extracellular vesicles comprise a lipid bilayer membrane comprising CD18. In some embodiments, between about 90% to about 99% of the megakaryocyte-derived extracellular vesicles comprise a lipid bilayer membrane comprising CD18. In some embodiments, between about 95% to about 99% of the megakaryocyte-derived extracellular vesicles comprise a lipid bilayer membrane comprising CD18.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD18.

In embodiments, the megakaryocyte-derived extracellular vesicles are characterized by a higher expression and/or presence of CD18 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD18 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about a 10-fold, an 8-fold to about a 64-fold, or about a 16-fold to about a 32-fold, or about a 16-fold to about a 24-fold greater amount of CD18 than platelet free plasma (PFP) MkEVs. In embodiments, the megakaryocyte-derived extracellular vesicles have about a 20-fold greater amount of CD18 than platelet free plasma (PFP) MkEVs. In embodiments, the megakaryocyte-derived extracellular vesicles have about a 1.1-fold to about a 4-fold or about a 1.1-fold to about a 2-fold greater amount of CD18 than platelet derived extracellular vesicles (PLT EVs). In embodiments, the megakaryocyte-derived extracellular vesicles have about a 1.5-fold greater amount of CD18 than platelet derived extracellular vesicles (PLT EVs).

In embodiments, the megakaryocyte-derived extracellular vesicles are characterized by a lower expression and/or presence of CD18 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD18 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the megakaryocyte-derived extracellular vesicles comprise a lipid bilayer membrane comprising CD43. In some embodiments, greater than about 40% of the megakaryocyte-derived extracellular vesicles comprise a lipid bilayer membrane comprising CD43. In some embodiments, greater than about 60% of the megakaryocyte-derived extracellular vesicles comprise a lipid bilayer membrane comprising CD43. In some embodiments, greater than about 70% of the megakaryocyte-derived extracellular vesicles comprise a lipid bilayer membrane comprising CD43. In some embodiments, greater than about 80% of the megakaryocyte-derived extracellular vesicles comprise a lipid bilayer membrane comprising CD43. In some embodiments, greater than about 90% of the megakaryocyte-derived extracellular vesicles comprise a lipid bilayer membrane comprising CD43. In some embodiments, greater than about 95% of the megakaryocyte-derived extracellular vesicles comprise a lipid bilayer membrane comprising CD43. In some embodiments, greater than about 99% of the megakaryocyte-derived extracellular vesicles comprise a lipid bilayer membrane comprising CD43.

In embodiments, about 50% or less of the megakaryocyte-derived extracellular vesicles comprise a lipid bilayer membrane comprising CD43. In some embodiments, about 40% or less of the megakaryocyte-derived extracellular vesicles comprise a lipid bilayer membrane comprising CD43. In some embodiments, about 60% or less of the megakaryocyte-derived extracellular vesicles comprise a lipid bilayer membrane comprising CD43. In some embodiments, about 70% or less of the megakaryocyte-derived extracellular vesicles comprise a lipid bilayer membrane comprising CD43. In some embodiments, about 80% or less of the megakaryocyte-derived extracellular vesicles comprise a lipid bilayer membrane comprising CD43. In some embodiments, about 90% or less of the megakaryocyte-derived extracellular vesicles comprise a lipid bilayer membrane comprising CD43. In some embodiments, about 95% or less of the megakaryocyte-derived extracellular vesicles comprise a lipid bilayer membrane comprising CD43. In some embodiments, about 99% or less of the megakaryocyte-derived extracellular vesicles comprise a lipid bilayer membrane comprising CD43.

In some embodiments, less than about 50% of the megakaryocyte-derived extracellular vesicles comprise a lipid bilayer membrane comprising CD43. In embodiments, less than about 40% of the megakaryocyte-derived extracellular vesicles comprise a lipid bilayer membrane comprising CD43. In some embodiments, less than about 30% of the megakaryocyte-derived extracellular vesicles comprise a lipid bilayer membrane comprising CD43. In some embodiments, less than about 25% of the megakaryocyte-derived extracellular vesicles comprise a lipid bilayer membrane comprising CD43. In some embodiments, less than about 20% of the megakaryocyte-derived extracellular vesicles comprise a lipid bilayer membrane comprising CD43. In some embodiments, less than about 15% of the megakaryocyte-derived extracellular vesicles comprise a lipid bilayer membrane comprising CD43. In some embodiments, less than about 10% of the megakaryocyte-derived extracellular vesicles comprise a lipid bilayer membrane comprising CD43. In some embodiments, less than about 5% of the megakaryocyte-derived extracellular vesicles comprise a lipid bilayer membrane comprising CD43. In some embodiments, less than about 1% of the megakaryocyte-derived extracellular vesicles comprise a lipid bilayer membrane comprising CD43.

In some embodiments, between about 1% to about 99% of the megakaryocyte-derived extracellular vesicles comprise a lipid bilayer membrane comprising CD43. In some embodiments, between about 1% to about 50% of the megakaryocyte-derived extracellular vesicles comprise a lipid bilayer membrane comprising CD43. In some embodiments, between about 1% to about 25% of the megakaryocyte-derived extracellular vesicles comprise a lipid bilayer membrane comprising CD43. In some embodiments, between about 1% to about 10% of the megakaryocyte-derived extracellular vesicles comprise a lipid bilayer membrane comprising CD43. In some embodiments, between about 1% to about 5% of the megakaryocyte-derived extracellular vesicles comprise a lipid bilayer membrane comprising CD43. In some embodiments, between about 1% to about 2% of the megakaryocyte-derived extracellular vesicles comprise a lipid bilayer membrane comprising CD43. In some embodiments, between about 50% to about 99% of the megakaryocyte-derived extracellular vesicles comprise a lipid bilayer membrane comprising CD43. In some embodiments, between about 75% to about 99% of the megakaryocyte-derived extracellular vesicles comprise a lipid bilayer membrane comprising CD43. In some embodiments, between about 90% to about 99% of the megakaryocyte-derived extracellular vesicles comprise a lipid bilayer membrane comprising CD43. In some embodiments, between about 95% to about 99% of the megakaryocyte-derived extracellular vesicles comprise a lipid bilayer membrane comprising CD43.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD43.

In embodiments, the megakaryocyte-derived extracellular vesicles are characterized by a higher expression and/or presence of CD43 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD43 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about an 4-fold to about a 64-fold, or about a 8-fold to about a 32-fold, or about a 8-fold to about a 16-fold greater amount of CD43 than platelet free plasma (PFP) MkEVs. In embodiments, the megakaryocyte-derived extracellular vesicles have about a 10-fold or about a 12-fold greater amount of CD43 than platelet free plasma (PFP) MkEVs. In embodiments, the megakaryocyte-derived extracellular vesicles have about a 1.5-fold to about an 8-fold or about a 2-fold to about a 4-fold greater amount of CD43 than platelet derived extracellular vesicles (PLT EVs). In embodiments, the megakaryocyte-derived extracellular vesicles have about a 3-fold or about a 4-fold greater amount of CD43 than platelet derived extracellular vesicles (PLT EVs).

In embodiments, the megakaryocyte-derived extracellular vesicles are characterized by a lower expression and/or presence of CD43 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD43 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the megakaryocyte-derived extracellular vesicles comprise a lipid bilayer membrane comprising CD11b. In some embodiments, greater than about 40% of the megakaryocyte-derived extracellular vesicles comprise a lipid bilayer membrane comprising CD11b. In some embodiments, greater than about 60% of the megakaryocyte-derived extracellular vesicles comprise a lipid bilayer membrane comprising CD11b. In some embodiments, greater than about 70% of the megakaryocyte-derived extracellular vesicles comprise a lipid bilayer membrane comprising CD11b. In some embodiments, greater than about 80% of the megakaryocyte-derived extracellular vesicles comprise a lipid bilayer membrane comprising CD11b. In some embodiments, greater than about 90% of the megakaryocyte-derived extracellular vesicles comprise a lipid bilayer membrane comprising CD11b. In some embodiments, greater than about 95% of the megakaryocyte-derived extracellular vesicles comprise a lipid bilayer membrane comprising CD11b. In some embodiments, greater than about 99% of the megakaryocyte-derived extracellular vesicles comprise a lipid bilayer membrane comprising CD11b.

In embodiments, about 50% or less of the megakaryocyte-derived extracellular vesicles comprise a lipid bilayer membrane comprising CD11b. In some embodiments, about 40% or less of the megakaryocyte-derived extracellular vesicles comprise a lipid bilayer membrane comprising CD11b. In some embodiments, about 60% or less of the megakaryocyte-derived extracellular vesicles comprise a lipid bilayer membrane comprising CD11b. In some embodiments, about 70% or less of the megakaryocyte-derived extracellular vesicles comprise a lipid bilayer membrane comprising CD11b. In some embodiments, about 80% or less of the megakaryocyte-derived extracellular vesicles comprise a lipid bilayer membrane comprising CD11b. In some embodiments, about 90% or less of the megakaryocyte-derived extracellular vesicles comprise a lipid bilayer membrane comprising CD11b. In some embodiments, about 95% or less of the megakaryocyte-derived extracellular vesicles comprise a lipid bilayer membrane comprising CD11b. In some embodiments, about 99% or less of the megakaryocyte-derived extracellular vesicles comprise a lipid bilayer membrane comprising CD11b.

In some embodiments, less than about 50% of the megakaryocyte-derived extracellular vesicles comprise a lipid bilayer membrane comprising CD11b. In embodiments, less than about 40% of the megakaryocyte-derived extracellular vesicles comprise a lipid bilayer membrane comprising CD11b. In some embodiments, less than about 30% of the megakaryocyte-derived extracellular vesicles comprise a lipid bilayer membrane comprising CD11b. In some embodiments, less than about 25% of the megakaryocyte-derived extracellular vesicles comprise a lipid bilayer membrane comprising CD11b. In some embodiments, less than about 20% of the megakaryocyte-derived extracellular vesicles comprise a lipid bilayer membrane comprising CD11b. In some embodiments, less than about 15% of the megakaryocyte-derived extracellular vesicles comprise a lipid bilayer membrane comprising CD11b. In some embodiments, less than about 10% of the megakaryocyte-derived extracellular vesicles comprise a lipid bilayer membrane comprising CD11b. In some embodiments, less than about 5% of the megakaryocyte-derived extracellular vesicles comprise a lipid bilayer membrane comprising CD11b. In some embodiments, less than about 1% of the megakaryocyte-derived extracellular vesicles comprise a lipid bilayer membrane comprising CD11b.

In some embodiments, between about 1% to about 99% of the megakaryocyte-derived extracellular vesicles comprise a lipid bilayer membrane comprising CD11b. In some embodiments, between about 1% to about 50% of the megakaryocyte-derived extracellular vesicles comprise a lipid bilayer membrane comprising CD11b. In some embodiments, between about 1% to about 25% of the megakaryocyte-derived extracellular vesicles comprise a lipid bilayer membrane comprising CD11b. In some embodiments, between about 1% to about 10% of the megakaryocyte-derived extracellular vesicles comprise a lipid bilayer membrane comprising CD11b. In some embodiments, between about 1% to about 5% of the megakaryocyte-derived extracellular vesicles comprise a lipid bilayer membrane comprising CD11b. In some embodiments, between about 1% to about 2% of the megakaryocyte-derived extracellular vesicles comprise a lipid bilayer membrane comprising CD11b. In some embodiments, between about 50% to about 99% of the megakaryocyte-derived extracellular vesicles comprise a lipid bilayer membrane comprising CD11b. In some embodiments, between about 75% to about 99% of the megakaryocyte-derived extracellular vesicles comprise a lipid bilayer membrane comprising CD11b. In some embodiments, between about 90% to about 99% of the megakaryocyte-derived extracellular vesicles comprise a lipid bilayer membrane comprising CD11b. In some embodiments, between about 95% to about 99% of the megakaryocyte-derived extracellular vesicles comprise a lipid bilayer membrane comprising CD11b.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD11b.

In embodiments, the megakaryocyte-derived extracellular vesicles are characterized by a higher expression and/or presence of CD11b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD11b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold, or about a 2-fold to about a 4-fold greater amount of CD11b than platelet free plasma (PFP) MkEVs. In embodiments, the megakaryocyte-derived extracellular vesicles have about a 3-fold greater amount of CD11b than platelet free plasma (PFP) MkEVs. In embodiments, the megakaryocyte-derived extracellular vesicles have about a 1.1-fold to about a 4-fold, or about a 1.1-fold to about a 2-fold greater amount of CD11b than platelet derived extracellular vesicles (PLT EVs). In embodiments, the megakaryocyte-derived extracellular vesicles have about a 1.5-fold greater amount of CD11b than platelet derived extracellular vesicles (PLT EVs).

In embodiments, the megakaryocyte-derived extracellular vesicles are characterized by a higher expression and/or presence of CD11b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD11b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD11b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD11b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the megakaryocyte-derived extracellular vesicles comprise a lipid bilayer membrane comprising CD21. In some embodiments, greater than about 40% of the megakaryocyte-derived extracellular vesicles comprise a lipid bilayer membrane comprising CD21. In some embodiments, greater than about 60% of the megakaryocyte-derived extracellular vesicles comprise a lipid bilayer membrane comprising CD21. In some embodiments, greater than about 70% of the megakaryocyte-derived extracellular vesicles comprise a lipid bilayer membrane comprising CD21. In some embodiments, greater than about 80% of the megakaryocyte-derived extracellular vesicles comprise a lipid bilayer membrane comprising CD21. In some embodiments, greater than about 90% of the megakaryocyte-derived extracellular vesicles comprise a lipid bilayer membrane comprising CD21. In some embodiments, greater than about 95% of the megakaryocyte-derived extracellular vesicles comprise a lipid bilayer membrane comprising CD21. In some embodiments, greater than about 99% of the megakaryocyte-derived extracellular vesicles comprise a lipid bilayer membrane comprising CD21.

In embodiments, about 50% or less of the megakaryocyte-derived extracellular vesicles comprise a lipid bilayer membrane comprising CD21. In some embodiments, about 40% or less of the megakaryocyte-derived extracellular vesicles comprise a lipid bilayer membrane comprising CD21. In some embodiments, about 60% or less of the megakaryocyte-derived extracellular vesicles comprise a lipid bilayer membrane comprising CD21. In some embodiments, about 70% or less of the megakaryocyte-derived extracellular vesicles comprise a lipid bilayer membrane comprising CD21. In some embodiments, about 80% or less of the megakaryocyte-derived extracellular vesicles comprise a lipid bilayer membrane comprising CD21. In some embodiments, about 90% or less of the megakaryocyte-derived extracellular vesicles comprise a lipid bilayer membrane comprising CD21. In some embodiments, about 95% or less of the megakaryocyte-derived extracellular vesicles comprise a lipid bilayer membrane comprising CD21. In some embodiments, about 99% or less of the megakaryocyte-derived extracellular vesicles comprise a lipid bilayer membrane comprising CD21.

In some embodiments, less than about 50% of the megakaryocyte-derived extracellular vesicles comprise a lipid bilayer membrane comprising CD21. In embodiments, less than about 40% of the megakaryocyte-derived extracellular vesicles comprise a lipid bilayer membrane comprising CD21. In some embodiments, less than about 30% of the megakaryocyte-derived extracellular vesicles comprise a lipid bilayer membrane comprising CD21. In some embodiments, less than about 25% of the megakaryocyte-derived extracellular vesicles comprise a lipid bilayer membrane comprising CD21. In some embodiments, less than about 20% of the megakaryocyte-derived extracellular vesicles comprise a lipid bilayer membrane comprising CD21. In some embodiments, less than about 15% of the megakaryocyte-derived extracellular vesicles comprise a lipid bilayer membrane comprising CD21. In some embodiments, less than about 10% of the megakaryocyte-derived extracellular vesicles comprise a lipid bilayer membrane comprising CD21. In some embodiments, less than about 5% of the megakaryocyte-derived extracellular vesicles comprise a lipid bilayer membrane comprising CD21. In some embodiments, less than about 1% of the megakaryocyte-derived extracellular vesicles comprise a lipid bilayer membrane comprising CD21.

In some embodiments, between about 1% to about 99% of the megakaryocyte-derived extracellular vesicles comprise a lipid bilayer membrane comprising CD21. In some embodiments, between about 1% to about 50% of the megakaryocyte-derived extracellular vesicles comprise a lipid bilayer membrane comprising CD21. In some embodiments, between about 1% to about 25% of the megakaryocyte-derived extracellular vesicles comprise a lipid bilayer membrane comprising CD21. In some embodiments, between about 1% to about 10% of the megakaryocyte-derived extracellular vesicles comprise a lipid bilayer membrane comprising CD21. In some embodiments, between about 1% to about 5% of the megakaryocyte-derived extracellular vesicles comprise a lipid bilayer membrane comprising CD21. In some embodiments, between about 1% to about 2% of the megakaryocyte-derived extracellular vesicles comprise a lipid bilayer membrane comprising CD21. In some embodiments, between about 50% to about 99% of the megakaryocyte-derived extracellular vesicles comprise a lipid bilayer membrane comprising CD21. In some embodiments, between about 75% to about 99% of the megakaryocyte-derived extracellular vesicles comprise a lipid bilayer membrane comprising CD21. In some embodiments, between about 90% to about 99% of the megakaryocyte-derived extracellular vesicles comprise a lipid bilayer membrane comprising CD21. In some embodiments, between about 95% to about 99% of the megakaryocyte-derived extracellular vesicles comprise a lipid bilayer membrane comprising CD21.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD21.

In embodiments, the megakaryocyte-derived extracellular vesicles are characterized by a higher expression and/or presence of CD21 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about a 64-fold, about a 4-fold to about a 32-fold, or about an 8-fold to about a 16-fold greater amount of CD21 than platelet free plasma (PFP) MkEVs. In embodiments, the megakaryocyte-derived extracellular vesicles have about a 10-fold or about a 12-fold greater amount of CD21 than platelet free plasma (PFP) MkEVs. In embodiments, the megakaryocyte-derived extracellular vesicles have about a 2-fold to about an 8-fold, or about a 4-fold to about an 8-fold greater amount of CD21 than platelet derived extracellular vesicles (PLT EVs). In embodiments, the megakaryocyte-derived extracellular vesicles have about a 4-fold or about a 5-fold greater amount of CD21 than platelet derived extracellular vesicles (PLT EVs).

In embodiments, the megakaryocyte-derived extracellular vesicles are characterized by a lower expression and/or presence of CD21 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD21 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, greater than about 50% of the megakaryocyte-derived extracellular vesicles comprise a lipid bilayer membrane comprising CD51. In some embodiments, greater than about 40% of the megakaryocyte-derived extracellular vesicles comprise a lipid bilayer membrane comprising CD51. In some embodiments, greater than about 60% of the megakaryocyte-derived extracellular vesicles comprise a lipid bilayer membrane comprising CD51. In some embodiments, greater than about 70% of the megakaryocyte-derived extracellular vesicles comprise a lipid bilayer membrane comprising CD51. In some embodiments, greater than about 80% of the megakaryocyte-derived extracellular vesicles comprise a lipid bilayer membrane comprising CD51. In some embodiments, greater than about 90% of the megakaryocyte-derived extracellular vesicles comprise a lipid bilayer membrane comprising CD51. In some embodiments, greater than about 95% of the megakaryocyte-derived extracellular vesicles comprise a lipid bilayer membrane comprising CD51. In some embodiments, greater than about 99% of the megakaryocyte-derived extracellular vesicles comprise a lipid bilayer membrane comprising CD51.

In embodiments, about 50% or less of the megakaryocyte-derived extracellular vesicles comprise a lipid bilayer membrane comprising CD51. In some embodiments, about 40% or less of the megakaryocyte-derived extracellular vesicles comprise a lipid bilayer membrane comprising CD51. In some embodiments, about 60% or less of the megakaryocyte-derived extracellular vesicles comprise a lipid bilayer membrane comprising CD51. In some embodiments, about 70% or less of the megakaryocyte-derived extracellular vesicles comprise a lipid bilayer membrane comprising CD51. In some embodiments, about 80% or less of the megakaryocyte-derived extracellular vesicles comprise a lipid bilayer membrane comprising CD51. In some embodiments, about 90% or less of the megakaryocyte-derived extracellular vesicles comprise a lipid bilayer membrane comprising CD51. In some embodiments, about 95% or less of the megakaryocyte-derived extracellular vesicles comprise a lipid bilayer membrane comprising CD51. In some embodiments, about 99% or less of the megakaryocyte-derived extracellular vesicles comprise a lipid bilayer membrane comprising CD51.

In some embodiments, less than about 50% of the megakaryocyte-derived extracellular vesicles comprise a lipid bilayer membrane comprising CD51. In embodiments, less than about 40% of the megakaryocyte-derived extracellular vesicles comprise a lipid bilayer membrane comprising CD51. In some embodiments, less than about 30% of the megakaryocyte-derived extracellular vesicles comprise a lipid bilayer membrane comprising CD51. In some embodiments, less than about 25% of the megakaryocyte-derived extracellular vesicles comprise a lipid bilayer membrane comprising CD51. In some embodiments, less than about 20% of the megakaryocyte-derived extracellular vesicles comprise a lipid bilayer membrane comprising CD51. In some embodiments, less than about 15% of the megakaryocyte-derived extracellular vesicles comprise a lipid bilayer membrane comprising CD51. In some embodiments, less than about 10% of the megakaryocyte-derived extracellular vesicles comprise a lipid bilayer membrane comprising CD51. In some embodiments, less than about 5% of the megakaryocyte-derived extracellular vesicles comprise a lipid bilayer membrane comprising CD51. In some embodiments, less than about 1% of the megakaryocyte-derived extracellular vesicles comprise a lipid bilayer membrane comprising CD51.

In some embodiments, between about 1% to about 99% of the megakaryocyte-derived extracellular vesicles comprise a lipid bilayer membrane comprising CD51. In some embodiments, between about 1% to about 50% of the megakaryo-cyte-derived extracellular vesicles comprise a lipid bilayer membrane comprising CD51. In some embodiments, between about 1% to about 25% of the megakaryocyte-derived extracellular vesicles comprise a lipid bilayer membrane comprising CD51. In some embodiments, between about 1% to about 10% of the megakaryocyte-derived extracellular vesicles comprise a lipid bilayer membrane comprising CD51. In some embodiments, between about 1% to about 5% of the megakaryocyte-derived extracellular vesicles comprise a lipid bilayer membrane comprising CD51. In some embodiments, between about 1% to about 2% of the megakaryocyte-derived extracellular vesicles comprise a lipid bilayer membrane comprising CD51. In some embodiments, between about 50% to about 99% of the megakaryocyte-derived extracellular vesicles comprise a lipid bilayer membrane comprising CD51. In some embodiments, between about 75% to about 99% of the megakaryo-cyte-derived extracellular vesicles comprise a lipid bilayer membrane comprising CD51. In some embodiments, between about 90% to about 99% of the megakaryocyte-derived extracellular vesicles comprise a lipid bilayer membrane comprising CD51. In some embodiments, between about 95% to about 99% of the megakaryocyte-derived extracellular vesicles comprise a lipid bilayer membrane comprising CD51.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD51.

In embodiments, the megakaryocyte-derived extracellular vesicles are characterized by a higher expression and/or presence of CD51 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD51 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD51 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD51 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 1.1-fold to about a 4-fold, or about a 1.1-fold to about a 2-fold lower amount of CD51 than platelet free plasma (PFP) MkEVs. In embodiments, the megakaryocyte-derived extracellular vesicles have about a 1.5-fold lower amount of CD51 than platelet free plasma (PFP) MkEVs. In embodiments, the megakaryocyte-derived extracellular vesicles have about a 1.1-fold to about a 4-fold, or about a 1.1-fold to about a 2-fold lower amount of CD51 than platelet derived extracellular vesicles (PLT EVs). In embodiments, the megakaryocyte-derived extracellular vesicles have about a 1.5-fold lower amount of CD51 than platelet derived extracellular vesicles (PLT EVs).

In embodiments, greater than about 50% of the mega-karyocyte-derived extracellular vesicles comprise a lipid bilayer membrane comprising CLEC-2. In some embodiments, greater than about 40% of the megakaryocyte-de-rived extracellular vesicles comprise a lipid bilayer membrane comprising CLEC-2. In some embodiments, greater than about 60% of the megakaryocyte-derived extracellular vesicles comprise a lipid bilayer membrane comprising CLEC-2. In some embodiments, greater than about 70% of the megakaryocyte-derived extracellular vesicles comprise a lipid bilayer membrane comprising CLEC-2. In some embodiments, greater than about 80% of the megakaryo-cyte-derived extracellular vesicles comprise a lipid bilayer membrane comprising CLEC-2. In some embodiments, greater than about 90% of the megakaryocyte-derived extra-cellular vesicles comprise a lipid bilayer membrane com-prising CLEC-2. In some embodiments, greater than about 95% of the megakaryocyte-derived extracellular vesicles comprise a lipid bilayer membrane comprising CLEC-2. In some embodiments, greater than about 99% of the mega-karyocyte-derived extracellular vesicles comprise a lipid bilayer membrane comprising CLEC-2.

In embodiments, about 50% or less of the megakaryocyte-derived extracellular vesicles comprise a lipid bilayer mem-brane comprising CLEC-2. In some embodiments, about 40% or less of the megakaryocyte-derived extracellular vesicles comprise a lipid bilayer membrane comprising CLEC-2. In some embodiments, about 60% or less of the megakaryocyte-derived extracellular vesicles comprise a lipid bilayer membrane comprising CLEC-2. In some embodiments, about 70% or less of the megakaryocyte-derived extracellular vesicles comprise a lipid bilayer membrane comprising CLEC-2. In some embodiments, about 80% or less of the megakaryocyte-derived extracellular vesicles comprise a lipid bilayer membrane comprising CLEC-2. In some embodiments, about 90% or less of the megakaryocyte-derived extracellular vesicles comprise a lipid bilayer membrane comprising CLEC-2. In some embodiments, about 95% or less of the megakaryocyte-derived extracellular vesicles comprise a lipid bilayer membrane comprising CLEC-2. In some embodiments, about 99% or less of the megakaryocyte-derived extracellular vesicles comprise a lipid bilayer membrane comprising CLEC-2.

In some embodiments, less than about 50% of the megakaryocyte-derived extracellular vesicles comprise a lipid bilayer membrane comprising CLEC-2. In embodiments, less than about 40% of the megakaryocyte-derived extracellular vesicles comprise a lipid bilayer membrane comprising CLEC-2. In some embodiments, less than about 30% of the megakaryocyte-derived extracellular vesicles comprise a lipid bilayer membrane comprising CLEC-2. In some embodiments, less than about 25% of the megakaryocyte-derived extracellular vesicles comprise a lipid bilayer membrane comprising CLEC-2. In some embodiments, less than about 20% of the megakaryocyte-derived extracellular vesicles comprise a lipid bilayer membrane comprising CLEC-2. In some embodiments, less than about 15% of the megakaryocyte-derived extracellular vesicles comprise a lipid bilayer membrane comprising CLEC-2. In some embodiments, less than about 10% of the megakaryocyte-derived extracellular vesicles comprise a lipid bilayer membrane comprising CLEC-2. In some embodiments, less than about 5% of the megakaryocyte-derived extracellular vesicles comprise a lipid bilayer membrane comprising CLEC-2. In some embodiments, less than about 1% of the megakaryocyte-derived extracellular vesicles comprise a lipid bilayer membrane comprising CLEC-2.

In some embodiments, between about 1% to about 99% of the megakaryocyte-derived extracellular vesicles comprise a lipid bilayer membrane comprising CLEC-2. In some embodiments, between about 1% to about 50% of the megakaryocyte-derived extracellular vesicles comprise a lipid bilayer membrane comprising CLEC-2. In some embodiments, between about 1% to about 25% of the megakaryocyte-derived extracellular vesicles comprise a lipid bilayer membrane comprising CLEC-2. In some embodiments, between about 1% to about 10% of the megakaryocyte-derived extracellular vesicles comprise a lipid bilayer membrane comprising CLEC-2. In some embodiments, between about 1% to about 5% of the megakaryocyte-derived extracellular vesicles comprise a lipid bilayer membrane comprising CLEC-2. In some embodiments, between about 1% to about 2% of the megakaryocyte-derived extracellular vesicles comprise a lipid bilayer membrane comprising CLEC-2. In some embodiments, between about 50% to about 99% of the megakaryocyte-derived extracellular vesicles comprise a lipid bilayer membrane comprising CLEC-2. In some embodiments, between about 75% to about 99% of the megakaryocyte-derived extracellular vesicles comprise a lipid bilayer membrane comprising CLEC-2. In some embodiments, between about 90% to about 99% of the megakaryocyte-derived extracellular vesicles comprise a lipid bilayer membrane comprising CLEC-2. In some embodiments, between about 95% to about 99% of the megakaryocyte-derived extracellular vesicles comprise a lipid bilayer membrane comprising CLEC-2.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CLEC-2.

In embodiments, the megakaryocyte-derived extracellular vesicles are characterized by a higher expression and/or presence of CLEC-2 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CLEC-2 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CLEC-2 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CLEC-2 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about a 16-fold, or about a 4-fold to about an 8-fold lower amount of CLEC-2 than platelet free plasma (PFP) MkEVs. In embodiments, the megakaryocyte-derived extracellular vesicles have about a 4-fold or about a 5-fold lower amount of CLEC-2 than platelet free plasma (PFP) MkEVs. In embodiments, the megakaryocyte-derived extracellular vesicles have about a 4-fold to about a 32-fold, or about an 8-fold to about a 16-fold lower amount of CLEC-2 than platelet derived extracellular vesicles (PLT EVs). In embodiments, the megakaryocyte-derived extracellular vesicles have about a 10-fold or about a 12-fold lower amount of CLEC-2 than platelet derived extracellular vesicles (PLT EVs).

In embodiments, greater than about 50% of the megakaryocyte-derived extracellular vesicles comprise a lipid bilayer membrane comprising LAMP-1 (CD107A). In some embodiments, greater than about 40% of the megakaryocyte-derived extracellular vesicles comprise a lipid bilayer membrane comprising LAMP-1 (CD107A). In some embodiments, greater than about 60% of the megakaryocyte-derived extracellular vesicles comprise a lipid bilayer membrane comprising LAMP-1 (CD107A). In some embodiments, greater than about 70% of the megakaryocyte-derived extracellular vesicles comprise a lipid bilayer membrane comprising LAMP-1 (CD107A). In some embodiments, greater than about 80% of the megakaryocyte-derived extracellular vesicles comprise a lipid bilayer membrane comprising LAMP-1 (CD107A). In some embodiments, greater than about 90% of the megakaryocyte-derived extracellular vesicles comprise a lipid bilayer membrane comprising LAMP-1 (CD107A). In some embodiments, greater than about 95% of the megakaryocyte-derived extracellular vesicles comprise a lipid bilayer membrane comprising LAMP-1 (CD107A). In some embodiments, greater than about 99% of the megakaryocyte-derived extracellular vesicles comprise a lipid bilayer membrane comprising LAMP-1 (CD107A).

In embodiments, about 50% or less of the megakaryocyte-derived extracellular vesicles comprise a lipid bilayer membrane comprising LAMP-1 (CD107A). In some embodiments, about 40% or less of the megakaryocyte-derived extracellular vesicles comprise a lipid bilayer membrane comprising LAMP-1 (CD107A). In some embodiments, about 60% or less of the megakaryocyte-derived extracellular vesicles comprise a lipid bilayer membrane comprising LAMP-1 (CD107A). In some embodiments, about 70% or less of the megakaryocyte-derived extracellular vesicles comprise a lipid bilayer membrane comprising LAMP-1 (CD107A). In some embodiments, about 80% or less of the megakaryocyte-derived extracellular vesicles comprise a lipid bilayer membrane comprising LAMP-1 (CD107A). In some embodiments, about 90% or less of the megakaryocyte-derived extracellular vesicles comprise a lipid bilayer membrane comprising LAMP-1 (CD107A). In some embodiments, about 95% or less of the megakaryocyte-derived extracellular vesicles comprise a lipid bilayer membrane comprising LAMP-1 (CD107A). In some embodiments, about 99% or less of the megakaryocyte-derived extracellular vesicles comprise a lipid bilayer membrane comprising LAMP-1 (CD107A).

In some embodiments, less than about 50% of the megakaryocyte-derived extracellular vesicles comprise a lipid bilayer membrane comprising LAMP-1 (CD107A). In embodiments, less than about 40% of the megakaryocyte-derived extracellular vesicles comprise a lipid bilayer membrane comprising LAMP-1 (CD107A). In some embodiments, less than about 30% of the megakaryocyte-derived extracellular vesicles comprise a lipid bilayer membrane comprising LAMP-1 (CD107A). In some embodiments, less than about 25% of the megakaryocyte-derived extracellular vesicles comprise a lipid bilayer membrane comprising LAMP-1 (CD107A). In some embodiments, less than about 20% of the megakaryocyte-derived extracellular vesicles comprise a lipid bilayer membrane comprising LAMP-1 (CD107A). In some embodiments, less than about 15% of the megakaryocyte-derived extracellular vesicles comprise a lipid bilayer membrane comprising LAMP-1 (CD107A). In some embodiments, less than about 10% of the megakaryocyte-derived extracellular vesicles comprise a lipid bilayer membrane comprising LAMP-1 (CD107A). In some embodiments, less than about 5% of the megakaryocyte-derived extracellular vesicles comprise a lipid bilayer membrane comprising LAMP-1 (CD107A). In some embodiments, less than about 1% of the megakaryocyte-derived extracellular vesicles comprise a lipid bilayer membrane comprising LAMP-1 (CD107A).

In some embodiments, between about 1% to about 99% of the megakaryocyte-derived extracellular vesicles comprise a lipid bilayer membrane comprising LAMP-1 (CD107A). In some embodiments, between about 1% to about 50% of the megakaryocyte-derived extracellular vesicles comprise a lipid bilayer membrane comprising LAMP-1 (CD107A). In some embodiments, between about 1% to about 25% of the megakaryocyte-derived extracellular vesicles comprise a lipid bilayer membrane comprising LAMP-1 (CD107A). In some embodiments, between about 1% to about 10% of the megakaryocyte-derived extracellular vesicles comprise a lipid bilayer membrane comprising LAMP-1 (CD107A). In some embodiments, between about 1% to about 5% of the megakaryocyte-derived extracellular vesicles comprise a lipid bilayer membrane comprising LAMP-1 (CD107A). In some embodiments, between about 1% to about 2% of the megakaryocyte-derived extracellular vesicles comprise a lipid bilayer membrane comprising LAMP-1 (CD107A). In some embodiments, between about 50% to about 99% of the megakaryocyte-derived extracellular vesicles comprise a lipid bilayer membrane comprising LAMP-1 (CD107A). In some embodiments, between about 75% to about 99% of the megakaryocyte-derived extracellular vesicles comprise a lipid bilayer membrane comprising LAMP-1 (CD107A). In some embodiments, between about 90% to about 99% of the megakaryocyte-derived extracellular vesicles comprise a lipid bilayer membrane comprising LAMP-1 (CD107A). In some embodiments, between about 95% to about 99% of the megakaryocyte-derived extracellular vesicles comprise a lipid bilayer membrane comprising LAMP-1 (CD107A).

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising LAMP-1 (CD107A).

In embodiments, the megakaryocyte-derived extracellular vesicles are free of, or substantially free of LAMP-1 (CD107A).

In embodiments, the megakaryocyte-derived extracellular vesicles are characterized by a higher expression and/or presence of LAMP-1 (CD107A) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of LAMP-1 (CD107A) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of LAMP-1 (CD107A) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of LAMP-1 (CD107A) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 1-fold to about a 2-fold, lower amount of LAMP-1 (CD107A) than platelet free plasma (PFP) MkEVs. In embodiments, the megakaryocyte-derived extracellular vesicles have an amount of LAMP-1 (CD107A) that is substantially the same as platelet free plasma (PFP) MkEVs. In embodiments, the megakaryocyte-derived extracellular vesicles have about a 2-fold to about a 8-fold, or about a 2-fold to about a 4-fold lower amount of LAMP-1 (CD107A) than platelet derived extracellular vesicles (PLT EVs). In embodiments, the megakaryocyte-derived extracellular vesicles have about a 3-fold or about a 4-fold lower amount of LAMP-1 (CD107A) than platelet derived extracellular vesicles (PLT EVs).

In embodiments, greater than about 50% of the megakaryocyte-derived extracellular vesicles comprise a lipid bilayer membrane comprising CD63. In some embodiments, greater than about 40% of the megakaryocyte-derived extracellular vesicles comprise a lipid bilayer membrane comprising CD63. In some embodiments, greater than about 60% of the megakaryocyte-derived extracellular vesicles comprise a lipid bilayer membrane comprising CD63. In some embodiments, greater than about 70% of the megakaryocyte-derived extracellular vesicles comprise a lipid bilayer membrane comprising CD63. In some embodiments, greater than about 80% of the megakaryocyte-derived extracellular vesicles comprise a lipid bilayer membrane comprising CD63. In some embodiments, greater than about 90% of the megakaryocyte-derived extracellular vesicles comprise a lipid bilayer membrane comprising CD63.

In some embodiments, greater than about 95% of the megakaryocyte-derived extracellular vesicles comprise a lipid bilayer membrane comprising CD63. In some embodiments, greater than about 99% of the megakaryocyte-derived extracellular vesicles comprise a lipid bilayer membrane comprising CD63.

In embodiments, about 50% or less of the megakaryocyte-derived extracellular vesicles comprise a lipid bilayer membrane comprising CD63. In some embodiments, about 40% or less of the megakaryocyte-derived extracellular vesicles comprise a lipid bilayer membrane comprising CD63. In some embodiments, about 60% or less of the megakaryocyte-derived extracellular vesicles comprise a lipid bilayer membrane comprising CD63. In some embodiments, about 70% or less of the megakaryocyte-derived extracellular vesicles comprise a lipid bilayer membrane comprising CD63. In some embodiments, about 80% or less of the megakaryocyte-derived extracellular vesicles comprise a lipid bilayer membrane comprising CD63. In some embodiments, about 90% or less of the megakaryocyte-derived extracellular vesicles comprise a lipid bilayer membrane comprising CD63. In some embodiments, about 95% or less of the megakaryocyte-derived extracellular vesicles comprise a lipid bilayer membrane comprising CD63. In some embodiments, about 99% or less of the megakaryocyte-derived extracellular vesicles comprise a lipid bilayer membrane comprising CD63.

In some embodiments, less than about 50% of the megakaryocyte-derived extracellular vesicles comprise a lipid bilayer membrane comprising CD63. In embodiments, less than about 40% of the megakaryocyte-derived extracellular vesicles comprise a lipid bilayer membrane comprising CD63. In some embodiments, less than about 30% of the megakaryocyte-derived extracellular vesicles comprise a lipid bilayer membrane comprising CD63. In some embodiments, less than about 25% of the megakaryocyte-derived extracellular vesicles comprise a lipid bilayer membrane comprising CD63. In some embodiments, less than about 20% of the megakaryocyte-derived extracellular vesicles comprise a lipid bilayer membrane comprising CD63. In some embodiments, less than about 15% of the megakaryocyte-derived extracellular vesicles comprise a lipid bilayer membrane comprising CD63. In some embodiments, less than about 10% of the megakaryocyte-derived extracellular vesicles comprise a lipid bilayer membrane comprising CD63. In some embodiments, less than about 5% of the megakaryocyte-derived extracellular vesicles comprise a lipid bilayer membrane comprising CD63. In some embodiments, less than about 1% of the megakaryocyte-derived extracellular vesicles comprise a lipid bilayer membrane comprising CD63.

In some embodiments, between about 1% to about 99% of the megakaryocyte-derived extracellular vesicles comprise a lipid bilayer membrane comprising CD63. In some embodiments, between about 1% to about 50% of the megakaryocyte-derived extracellular vesicles comprise a lipid bilayer membrane comprising CD63. In some embodiments, between about 1% to about 25% of the megakaryocyte-derived extracellular vesicles comprise a lipid bilayer membrane comprising CD63. In some embodiments, between about 1% to about 10% of the megakaryocyte-derived extracellular vesicles comprise a lipid bilayer membrane comprising CD63. In some embodiments, between about 1% to about 5% of the megakaryocyte-derived extracellular vesicles comprise a lipid bilayer membrane comprising CD63. In some embodiments, between about 1% to about 2% of the megakaryocyte-derived extracellular vesicles comprise a lipid bilayer membrane comprising CD63. In some embodiments, between about 50% to about 99% of the megakaryocyte-derived extracellular vesicles comprise a lipid bilayer membrane comprising CD63. In some embodiments, between about 75% to about 99% of the megakaryocyte-derived extracellular vesicles comprise a lipid bilayer membrane comprising CD63. In some embodiments, between about 90% to about 99% of the megakaryocyte-derived extracellular vesicles comprise a lipid bilayer membrane comprising CD63. In some embodiments, between about 95% to about 99% of the megakaryocyte-derived extracellular vesicles comprise a lipid bilayer membrane comprising CD63.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD63.

In some embodiments, between about 1% to about 30% of the megakaryocyte-derived extracellular vesicles comprise a lipid bilayer membrane comprising CD63. In some embodiments, between about 5% to about 25% of the megakaryocyte-derived extracellular vesicles comprise a lipid bilayer membrane comprising CD63. In some embodiments, between about 10% to about 20% of the megakaryocyte-derived extracellular vesicles comprise a lipid bilayer membrane comprising CD63. In some embodiments, between about 13% to about 19% of the megakaryocyte-derived extracellular vesicles comprise a lipid bilayer membrane comprising CD63.

In embodiments, the megakaryocyte-derived extracellular vesicles are characterized by a higher expression and/or presence of CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold, or about a 2-fold to about a 4-fold greater amount of CD63 than platelet free plasma (PFP) MkEVs. In embodiments, the megakaryocyte-derived extracellular vesicles have about a 2-fold or about a 3-fold greater amount of CD63 than platelet free plasma (PFP) MkEVs. In embodiments, the megakaryocyte-derived extracellular vesicles have about a 1.1-fold to about a 2-fold lower amount of CD63 than platelet derived extracellular vesicles (PLT EVs). In embodiments, the megakaryocyte-derived extracellular vesicles have about a 1.1-fold or about a 1.2-fold lower amount of CD63 than platelet derived extracellular vesicles (PLT EVs). In embodiments, the megakaryocyte-derived extracellular vesicles have an amount of CD63 that is substantially the same as platelet derived extracellular vesicles (PLT EVs).

In embodiments, greater than about 50% of the megakaryocyte-derived extracellular vesicles comprise a lipid bilayer membrane comprising CD42b. In some embodiments, greater than about 40% of the megakaryocyte-derived extracellular vesicles comprise a lipid bilayer membrane comprising CD42b. In some embodiments, greater than about 60% of the megakaryocyte-derived extracellular vesicles comprise a lipid bilayer membrane comprising CD42b. In some embodiments, greater than about 70% of the megakaryocyte-derived extracellular vesicles comprise a lipid bilayer membrane comprising CD42b. In some embodiments, greater than about 80% of the megakaryocyte-derived extracellular vesicles comprise a lipid bilayer membrane comprising CD42b. In some embodiments, greater than about 90% of the megakaryocyte-derived extracellular vesicles comprise a lipid bilayer membrane comprising CD42b. In some embodiments, greater than about 95% of the megakaryocyte-derived extracellular vesicles comprise a lipid bilayer membrane comprising CD42b. In some embodiments, greater than about 99% of the megakaryocyte-derived extracellular vesicles comprise a lipid bilayer membrane comprising CD42b.

In embodiments, about 50% or less of the megakaryocyte-derived extracellular vesicles comprise a lipid bilayer membrane comprising CD42b. In some embodiments, about 40% or less of the megakaryocyte-derived extracellular vesicles comprise a lipid bilayer membrane comprising CD42b. In some embodiments, about 60% or less of the megakaryocyte-derived extracellular vesicles comprise a lipid bilayer membrane comprising CD42b. In some embodiments, about 70% or less of the megakaryocyte-derived extracellular vesicles comprise a lipid bilayer membrane comprising CD42b. In some embodiments, about 80% or less of the megakaryocyte-derived extracellular vesicles comprise a lipid bilayer membrane comprising CD42b. In some embodiments, about 90% or less of the megakaryocyte-derived extracellular vesicles comprise a lipid bilayer membrane comprising CD42b. In some embodiments, about 95% or less of the megakaryocyte-derived extracellular vesicles comprise a lipid bilayer membrane comprising CD42b. In some embodiments, about 99% or less of the megakaryocyte-derived extracellular vesicles comprise a lipid bilayer membrane comprising CD42b.

In some embodiments, less than about 50% of the mega-karyocyte-derived extracellular vesicles comprise a lipid bilayer membrane comprising CD42b. In embodiments, less than about 40% of the megakaryocyte-derived extracellular vesicles comprise a lipid bilayer membrane comprising CD42b. In some embodiments, less than about 30% of the megakaryocyte-derived extracellular vesicles comprise a lipid bilayer membrane comprising CD42b. In some embodiments, less than about 25% of the megakaryocyte-derived extracellular vesicles comprise a lipid bilayer membrane comprising CD42b. In some embodiments, less than about 20% of the megakaryocyte-derived extracellular vesicles comprise a lipid bilayer membrane comprising CD42b. In some embodiments, less than about 15% of the megakaryocyte-derived extracellular vesicles comprise a lipid bilayer membrane comprising CD42b. In some embodiments, less than about 10% of the megakaryocyte-derived extracellular vesicles comprise a lipid bilayer membrane comprising CD42b. In some embodiments, less than about 5% of the megakaryocyte-derived extracellular vesicles comprise a lipid bilayer membrane comprising CD42b. In some embodiments, less than about 1% of the megakaryocyte-derived extracellular vesicles comprise a lipid bilayer membrane comprising CD42b.

In some embodiments, between about 1% to about 99% of the megakaryocyte-derived extracellular vesicles comprise a lipid bilayer membrane comprising CD42b. In some embodiments, between about 1% to about 50% of the megakaryocyte-derived extracellular vesicles comprise a lipid bilayer membrane comprising CD42b. In some embodiments, between about 1% to about 25% of the megakaryocyte-derived extracellular vesicles comprise a lipid bilayer membrane comprising CD42b. In some embodiments, between about 1% to about 10% of the megakaryocyte-derived extracellular vesicles comprise a lipid bilayer membrane comprising CD42b. In some embodiments, between about 1% to about 5% of the mega-karyocyte-derived extracellular vesicles comprise a lipid bilayer membrane comprising CD42b. In some embodiments, between about 1% to about 2% of the megakaryo-cyte-derived extracellular vesicles comprise a lipid bilayer membrane comprising CD42b. In some embodiments, between about 50% to about 99% of the megakaryocyte-derived extracellular vesicles comprise a lipid bilayer membrane comprising CD42b. In some embodiments, between about 75% to about 99% of the megakaryocyte-derived extracellular vesicles comprise a lipid bilayer membrane comprising CD42b. In some embodiments, between about 90% to about 99% of the megakaryocyte-derived extracellular vesicles comprise a lipid bilayer membrane comprising CD42b. In some embodiments, between about 95% to about 99% of the megakaryocyte-derived extracellular vesicles comprise a lipid bilayer membrane comprising CD42b.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD42b.

In embodiments, the megakaryocyte-derived extracellular vesicles are characterized by a higher expression and/or presence of CD42b than naturally-occurring megakaryo-cyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD42b than naturally-occurring megakaryocyte-derived extracellu-lar vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD42b than naturally-occurring megakaryo-cyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD42b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about an 8-fold to about a 32-fold, or about a 10-fold to about a 20-fold lower amount of CD42b than platelet free plasma (PFP) MkEVs. In embodiments, the megakaryocyte-derived extracellular vesicles have about a 16-fold or about a 20-fold lower amount of CD42b than platelet free plasma (PFP) MkEVs. In embodiments, the megakaryocyte-derived extracellular vesicles have about a 64-fold to about a 128-fold, or about a 50-fold to about a 75-fold lower amount of CD42b than platelet derived extra-cellular vesicles (PLT EVs). In embodiments, the mega-karyocyte-derived extracellular vesicles have about a 64-fold or about a 70-fold lower amount of CD42b than platelet derived extracellular vesicles (PLT EVs).

In embodiments, greater than about 50% of the mega-karyocyte-derived extracellular vesicles comprise a lipid bilayer membrane comprising CD9. In some embodiments, greater than about 40% of the megakaryocyte-derived extra-cellular vesicles comprise a lipid bilayer membrane com-prising CD9. In some embodiments, greater than about 60% of the megakaryocyte-derived extracellular vesicles com-prise a lipid bilayer membrane comprising CD9. In some embodiments, greater than about 70% of the megakaryo-cyte-derived extracellular vesicles comprise a lipid bilayer membrane comprising CD9. In some embodiments, greater than about 80% of the megakaryocyte-derived extracellular vesicles comprise a lipid bilayer membrane comprising CD9. In some embodiments, greater than about 90% of the megakaryocyte-derived extracellular vesicles comprise a lipid bilayer membrane comprising CD9. In some embodiments, greater than about 95% of the megakaryocyte-derived extracellular vesicles comprise a lipid bilayer membrane comprising CD9. In some embodiments, greater than about 99% of the megakaryocyte-derived extracellular vesicles comprise a lipid bilayer membrane comprising CD9.

In embodiments, about 50% or less of the megakaryocyte-derived extracellular vesicles comprise a lipid bilayer membrane comprising CD9. In some embodiments, about 40% or less of the megakaryocyte-derived extracellular vesicles comprise a lipid bilayer membrane comprising CD9. In some embodiments, about 60% or less of the megakaryocyte-derived extracellular vesicles comprise a lipid bilayer membrane comprising CD9. In some embodiments, about 70% or less of the megakaryocyte-derived extracellular vesicles comprise a lipid bilayer membrane comprising CD9. In some embodiments, about 80% or less of the megakaryocyte-derived extracellular vesicles comprise a lipid bilayer membrane comprising CD9. In some embodiments, about 90% or less of the megakaryocyte-derived extracellular vesicles comprise a lipid bilayer membrane comprising CD9. In some embodiments, about 95% or less of the megakaryocyte-derived extracellular vesicles comprise a lipid bilayer membrane comprising CD9. In some embodiments, about 99% or less of the megakaryocyte-derived extracellular vesicles comprise a lipid bilayer membrane comprising CD9.

In some embodiments, less than about 50% of the megakaryocyte-derived extracellular vesicles comprise a lipid bilayer membrane comprising CD9. In embodiments, less than about 40% of the megakaryocyte-derived extracellular vesicles comprise a lipid bilayer membrane comprising CD9. In some embodiments, less than about 30% of the megakaryocyte-derived extracellular vesicles comprise a lipid bilayer membrane comprising CD9. In some embodiments, less than about 25% of the megakaryocyte-derived extracellular vesicles comprise a lipid bilayer membrane comprising CD9. In some embodiments, less than about 20% of the megakaryocyte-derived extracellular vesicles comprise a lipid bilayer membrane comprising CD9. In some embodiments, less than about 15% of the megakaryocyte-derived extracellular vesicles comprise a lipid bilayer membrane comprising CD9. In some embodiments, less than about 10% of the megakaryocyte-derived extracellular vesicles comprise a lipid bilayer membrane comprising CD9. In some embodiments, less than about 5% of the megakaryocyte-derived extracellular vesicles comprise a lipid bilayer membrane comprising CD9. In some embodiments, less than about 1% of the megakaryocyte-derived extracellular vesicles comprise a lipid bilayer membrane comprising CD9.

In some embodiments, between about 1% to about 99% of the megakaryocyte-derived extracellular vesicles comprise a lipid bilayer membrane comprising CD9. In some embodiments, between about 1% to about 50% of the megakaryocyte-derived extracellular vesicles comprise a lipid bilayer membrane comprising CD9. In some embodiments, between about 1% to about 25% of the megakaryocyte-derived extracellular vesicles comprise a lipid bilayer membrane comprising CD9. In some embodiments, between about 1% to about 10% of the megakaryocyte-derived extracellular vesicles comprise a lipid bilayer membrane comprising CD9. In some embodiments, between about 1% to about 5% of the megakaryocyte-derived extracellular vesicles comprise a lipid bilayer membrane comprising CD9. In some embodiments, between about 1% to about 2% of the megakaryocyte-derived extracellular vesicles comprise a lipid bilayer membrane comprising CD9. In some embodiments, between about 20% to about 60% of the megakaryocyte-derived extracellular vesicles comprise a lipid bilayer membrane comprising CD9. In some embodiments, between about 35% to about 55% of the megakaryocyte-derived extracellular vesicles comprise a lipid bilayer membrane comprising CD9. In some embodiments, between about 50% to about 99% of the megakaryocyte-derived extracellular vesicles comprise a lipid bilayer membrane comprising CD9. In some embodiments, between about 75% to about 99% of the megakaryocyte-derived extracellular vesicles comprise a lipid bilayer membrane comprising CD9. In some embodiments, between about 90% to about 99% of the megakaryocyte-derived extracellular vesicles comprise a lipid bilayer membrane comprising CD9. In some embodiments, between about 95% to about 99% of the megakaryocyte-derived extracellular vesicles comprise a lipid bilayer membrane comprising CD9.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD9.

In some embodiments, between about 50% to about 70% of the megakaryocyte-derived extracellular vesicles comprise a lipid bilayer membrane comprising CD9. In some embodiments, between about 60% to about 70% of the megakaryocyte-derived extracellular vesicles comprise a lipid bilayer membrane comprising CD9. In some embodiments, between about 62% to about 68% of the megakaryocyte-derived extracellular vesicles comprise a lipid bilayer membrane comprising CD9. In some embodiments, between about 65% to about 66% of the megakaryocyte-derived extracellular vesicles comprise a lipid bilayer membrane comprising CD9.

In some embodiments, between about 50% to about 99% of the megakaryocyte-derived extracellular vesicles comprise a lipid bilayer membrane comprising CD9.

In embodiments, the megakaryocyte-derived extracellular vesicles are characterized by a higher expression and/or presence of CD9 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD9 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD9 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD9 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 1.5-fold to about a 4-fold, or about a 2-fold to about a 4-fold greater amount of CD9 than platelet free plasma (PFP) MkEVs. In embodiments, the megakaryocyte-derived extracellular vesicles have about a 2-fold greater amount of CD9 than platelet free plasma (PFP) MkEVs. In embodiments, the megakaryocyte-derived extracellular vesicles have about a 1.1-fold to about a 2-fold lower amount of CD9 than platelet derived extracellular vesicles (PLT EVs). In embodiments, the megakaryocyte-derived extracellular vesicles have about a 1.1-fold or about a 1.2-fold lower amount of CD9 than platelet derived extracellular vesicles (PLT EVs). In embodiments, the megakaryocyte-derived extracellular vesicles have an amount of CD9 that is substantially the same as platelet derived extracellular vesicles (PLT EVs).

In embodiments, greater than about 50% of the megakaryocyte-derived extracellular vesicles comprise a lipid bilayer membrane comprising CD31. In some embodiments, greater than about 40% of the megakaryocyte-derived extracellular vesicles comprise a lipid bilayer membrane comprising CD31. In some embodiments, greater than about 60% of the megakaryocyte-derived extracellular vesicles comprise a lipid bilayer membrane comprising CD31. In some embodiments, greater than about 70% of the megakaryocyte-derived extracellular vesicles comprise a lipid bilayer membrane comprising CD31. In some embodiments, greater than about 80% of the megakaryocyte-derived extracellular vesicles comprise a lipid bilayer membrane comprising CD31. In some embodiments, greater than about 90% of the megakaryocyte-derived extracellular vesicles comprise a lipid bilayer membrane comprising CD31. In some embodiments, greater than about 95% of the megakaryocyte-derived extracellular vesicles comprise a lipid bilayer membrane comprising CD31. In some embodiments, greater than about 99% of the megakaryocyte-derived extracellular vesicles comprise a lipid bilayer membrane comprising CD31.

In embodiments, about 50% or less of the megakaryocyte-derived extracellular vesicles comprise a lipid bilayer membrane comprising CD31. In some embodiments, about 40% or less of the megakaryocyte-derived extracellular vesicles comprise a lipid bilayer membrane comprising CD31. In some embodiments, about 60% or less of the megakaryocyte-derived extracellular vesicles comprise a lipid bilayer membrane comprising CD31. In some embodiments, about 70% or less of the megakaryocyte-derived extracellular vesicles comprise a lipid bilayer membrane comprising CD31. In some embodiments, about 80% or less of the megakaryocyte-derived extracellular vesicles comprise a lipid bilayer membrane comprising CD31. In some embodiments, about 90% or less of the megakaryocyte-derived extracellular vesicles comprise a lipid bilayer membrane comprising CD31. In some embodiments, about 95% or less of the megakaryocyte-derived extracellular vesicles comprise a lipid bilayer membrane comprising CD31. In some embodiments, about 99% or less of the megakaryocyte-derived extracellular vesicles comprise a lipid bilayer membrane comprising CD31.

In some embodiments, less than about 50% of the megakaryocyte-derived extracellular vesicles comprise a lipid bilayer membrane comprising CD31. In embodiments, less than about 40% of the megakaryocyte-derived extracellular vesicles comprise a lipid bilayer membrane comprising CD31. In some embodiments, less than about 30% of the megakaryocyte-derived extracellular vesicles comprise a lipid bilayer membrane comprising CD31. In some embodiments, less than about 25% of the megakaryocyte-derived extracellular vesicles comprise a lipid bilayer membrane comprising CD31. In some embodiments, less than about 20% of the megakaryocyte-derived extracellular vesicles comprise a lipid bilayer membrane comprising CD31. In some embodiments, less than about 15% of the megakaryocyte-derived extracellular vesicles comprise a lipid bilayer membrane comprising CD31. In some embodiments, less than about 10% of the megakaryocyte-derived extracellular vesicles comprise a lipid bilayer membrane comprising CD31. In some embodiments, less than about 5% of the megakaryocyte-derived extracellular vesicles comprise a lipid bilayer membrane comprising CD31. In some embodiments, less than about 1% of the megakaryocyte-derived extracellular vesicles comprise a lipid bilayer membrane comprising CD31.

In some embodiments, between about 1% to about 99% of the megakaryocyte-derived extracellular vesicles comprise a lipid bilayer membrane comprising CD31. In some embodiments, between about 1% to about 50% of the megakaryocyte-derived extracellular vesicles comprise a lipid bilayer membrane comprising CD31. In some embodiments, between about 1% to about 25% of the megakaryocyte-derived extracellular vesicles comprise a lipid bilayer membrane comprising CD31. In some embodiments, between about 1% to about 10% of the megakaryocyte-derived extracellular vesicles comprise a lipid bilayer membrane comprising CD31. In some embodiments, between about 1% to about 5% of the megakaryocyte-derived extracellular vesicles comprise a lipid bilayer membrane comprising CD31. In some embodiments, between about 1% to about 2% of the megakaryocyte-derived extracellular vesicles comprise a lipid bilayer membrane comprising CD31. In some embodiments, between about 50% to about 99% of the megakaryocyte-derived extracellular vesicles comprise a lipid bilayer membrane comprising CD31. In some embodiments, between about 75% to about 99% of the megakaryocyte-derived extracellular vesicles comprise a lipid bilayer membrane comprising CD31. In some embodiments, between about 90% to about 99% of the megakaryocyte-derived extracellular vesicles comprise a lipid bilayer membrane comprising CD31. In some embodiments, between about 95% to about 99% of the megakaryocyte-derived extracellular vesicles comprise a lipid bilayer membrane comprising CD31.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD31.

In some embodiments, between about 5% to about 50% of the megakaryocyte-derived extracellular vesicles comprise a lipid bilayer membrane comprising CD31. In some embodiments, between about 10% to about 40% of the megakaryocyte-derived extracellular vesicles comprise a lipid bilayer membrane comprising CD31. In some embodiments, between about 10% to about 35% of the megakaryocyte-derived extracellular vesicles comprise a lipid bilayer membrane comprising CD31. In some embodiments, between about 13% to about 31% of the megakaryocyte-derived extracellular vesicles comprise a lipid bilayer membrane comprising CD31.

In embodiments, the megakaryocyte-derived extracellular vesicles are characterized by a higher expression and/or presence of CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 1.1-fold to about a 4-fold, or about a 1.1-fold to about a 2-fold lower amount of CD31 than platelet free plasma (PFP) MkEVs. In embodiments, the megakaryocyte-derived extracellular vesicles have about a 1.5-fold lower amount of CD31 than platelet free plasma (PFP) MkEVs. In embodiments, the megakaryocyte-derived extracellular vesicles have about a 2-fold to about a 4-fold lower amount of CD31 than platelet derived extracellular vesicles (PLT EVs). In embodiments, the megakaryocyte-derived extracellular vesicles have about a 2-fold or about a 3-fold lower amount of CD31 than platelet derived extracellular vesicles (PLT EVs).

In embodiments, greater than about 50% of the megakaryocyte-derived extracellular vesicles comprise a lipid bilayer membrane comprising CD47. In some embodiments, greater than about 40% of the megakaryocyte-derived extracellular vesicles comprise a lipid bilayer membrane comprising CD47. In some embodiments, greater than about 60% of the megakaryocyte-derived extracellular vesicles comprise a lipid bilayer membrane comprising CD47. In some embodiments, greater than about 70% of the megakaryocyte-derived extracellular vesicles comprise a lipid bilayer membrane comprising CD47. In some embodiments, greater than about 80% of the megakaryocyte-derived extracellular vesicles comprise a lipid bilayer membrane comprising CD47. In some embodiments, greater than about 90% of the megakaryocyte-derived extracellular vesicles comprise a lipid bilayer membrane comprising CD47. In some embodiments, greater than about 95% of the megakaryocyte-derived extracellular vesicles comprise a lipid bilayer membrane comprising CD47. In some embodiments, greater than about 99% of the megakaryocyte-derived extracellular vesicles comprise a lipid bilayer membrane comprising CD47.

In embodiments, about 50% or less of the megakaryocyte-derived extracellular vesicles comprise a lipid bilayer membrane comprising CD47. In some embodiments, about 40% or less of the megakaryocyte-derived extracellular vesicles comprise a lipid bilayer membrane comprising CD47. In some embodiments, about 60% or less of the megakaryocyte-derived extracellular vesicles comprise a lipid bilayer membrane comprising CD47. In some embodiments, about 70% or less of the megakaryocyte-derived extracellular vesicles comprise a lipid bilayer membrane comprising CD47. In some embodiments, about 80% or less of the megakaryocyte-derived extracellular vesicles comprise a lipid bilayer membrane comprising CD47. In some embodiments, about 90% or less of the megakaryocyte-derived extracellular vesicles comprise a lipid bilayer membrane comprising CD47. In some embodiments, about 95% or less of the megakaryocyte-derived extracellular vesicles comprise a lipid bilayer membrane comprising CD47. In some embodiments, about 99% or less of the megakaryocyte-derived extracellular vesicles comprise a lipid bilayer membrane comprising CD47.

In some embodiments, less than about 50% of the megakaryocyte-derived extracellular vesicles comprise a lipid bilayer membrane comprising CD47. In embodiments, less than about 40% of the megakaryocyte-derived extracellular vesicles comprise a lipid bilayer membrane comprising CD47. In some embodiments, less than about 30% of the megakaryocyte-derived extracellular vesicles comprise a lipid bilayer membrane comprising CD47. In some embodiments, less than about 25% of the megakaryocyte-derived extracellular vesicles comprise a lipid bilayer membrane comprising CD47. In some embodiments, less than about 20% of the megakaryocyte-derived extracellular vesicles comprise a lipid bilayer membrane comprising CD47. In some embodiments, less than about 15% of the megakaryocyte-derived extracellular vesicles comprise a lipid bilayer membrane comprising CD47. In some embodiments, less than about 10% of the megakaryocyte-derived extracellular vesicles comprise a lipid bilayer membrane comprising CD47. In some embodiments, less than about 5% of the megakaryocyte-derived extracellular vesicles comprise a lipid bilayer membrane comprising CD47. In some embodiments, less than about 1% of the megakaryocyte-derived extracellular vesicles comprise a lipid bilayer membrane comprising CD47.

In some embodiments, between about 1% to about 99% of the megakaryocyte-derived extracellular vesicles comprise a lipid bilayer membrane comprising CD47. In some embodiments, between about 1% to about 50% of the megakaryocyte-derived extracellular vesicles comprise a lipid bilayer membrane comprising CD47. In some embodiments, between about 1% to about 25% of the megakaryocyte-derived extracellular vesicles comprise a lipid bilayer membrane comprising CD47. In some embodiments, between about 1% to about 10% of the megakaryocyte-derived extracellular vesicles comprise a lipid bilayer membrane comprising CD47. In some embodiments, between about 1% to about 5% of the megakaryocyte-derived extracellular vesicles comprise a lipid bilayer membrane comprising CD47. In some embodiments, between about 1% to about 2% of the megakaryocyte-derived extracellular vesicles comprise a lipid bilayer membrane comprising CD47. In some embodiments, between about 50% to about 99% of the megakaryocyte-derived extracellular vesicles comprise a lipid bilayer membrane comprising CD47. In some embodiments, between about 75% to about 99% of the megakaryocyte-derived extracellular vesicles comprise a lipid bilayer membrane comprising CD47. In some embodiments, between about 90% to about 99% of the megakaryocyte-derived extracellular vesicles comprise a lipid bilayer membrane comprising CD47. In some embodiments, between about 95% to about 99% of the megakaryocyte-derived extracellular vesicles comprise a lipid bilayer membrane comprising CD47.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD47.

In some embodiments, between about 1% to about 50% of the megakaryocyte-derived extracellular vesicles comprise a lipid bilayer membrane comprising CD47. In some embodiments, between about 10% to about 40% of the megakaryocyte-derived extracellular vesicles comprise a lipid bilayer membrane comprising CD47. In some embodiments, between about 20% to about 40% of the megakaryocyte-derived extracellular vesicles comprise a lipid bilayer membrane comprising CD47. In some embodiments, between about 25% to about 35% of the megakaryocyte-derived extracellular vesicles comprise a lipid bilayer membrane comprising CD47.

In embodiments, the megakaryocyte-derived extracellular vesicles are characterized by a higher expression and/or presence of CD47 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD47 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD47 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD47 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 128-fold to about a 512-fold, or about a 256-fold to about a 512-fold, or about a 250-fold to about a 300-fold greater amount of CD47 than platelet free plasma (PFP) MkEVs. In embodiments, the megakaryocyte-derived extracellular vesicles have about a 256-fold or about a 300-fold greater amount of CD47 than platelet free plasma (PFP) MkEVs. In embodiments, the megakaryocyte-derived extracellular vesicles have about a 1.1-fold to about a 2-fold lower amount of CD47 than platelet derived extracellular vesicles (PLT EVs). In embodiments, the megakaryocyte-derived extracellular vesicles have about a 1.1-fold or about a 1.5-fold lower amount of CD47 than platelet derived extracellular vesicles (PLT EVs). In embodiments, the megakaryocyte-derived extracellular vesicles have an amount of CD47 that is substantially the same as platelet derived extracellular vesicles (PLT EVs).

In embodiments, greater than about 50% of the mega-karyocyte-derived extracellular vesicles comprise a lipid bilayer membrane comprising CD147. In some embodiments, greater than about 40% of the megakaryocyte-derived extracellular vesicles comprise a lipid bilayer membrane comprising CD147. In some embodiments, greater than about 60% of the megakaryocyte-derived extracellular vesicles comprise a lipid bilayer membrane comprising CD147. In some embodiments, greater than about 70% of the megakaryocyte-derived extracellular vesicles comprise a lipid bilayer membrane comprising CD147. In some embodiments, greater than about 80% of the megakaryocyte-derived extracellular vesicles comprise a lipid bilayer membrane comprising CD147. In some embodiments, greater than about 90% of the megakaryocyte-derived extracellular vesicles comprise a lipid bilayer membrane comprising CD147. In some embodiments, greater than about 95% of the megakaryocyte-derived extracellular vesicles comprise a lipid bilayer membrane comprising CD147. In some embodiments, greater than about 99% of the megakaryocyte-derived extracellular vesicles comprise a lipid bilayer membrane comprising CD147.

In embodiments, about 50% or less of the megakaryocyte-derived extracellular vesicles comprise a lipid bilayer membrane comprising CD147. In some embodiments, about 40% or less of the megakaryocyte-derived extracellular vesicles comprise a lipid bilayer membrane comprising CD147. In some embodiments, about 60% or less of the megakaryocyte-derived extracellular vesicles comprise a lipid bilayer membrane comprising CD147. In some embodiments, about 70% or less of the megakaryocyte-derived extracellular vesicles comprise a lipid bilayer membrane comprising CD147. In some embodiments, about 80% or less of the megakaryocyte-derived extracellular vesicles comprise a lipid bilayer membrane comprising CD147. In some embodiments, about 90% or less of the megakaryocyte-derived extracellular vesicles comprise a lipid bilayer membrane comprising CD147. In some embodiments, about 95% or less of the megakaryocyte-derived extracellular vesicles comprise a lipid bilayer membrane comprising CD147. In some embodiments, about 99% or less of the megakaryocyte-derived extracellular vesicles comprise a lipid bilayer membrane comprising CD147.

In some embodiments, less than about 50% of the megakaryocyte-derived extracellular vesicles comprise a lipid bilayer membrane comprising CD147. In embodiments, less than about 40% of the megakaryocyte-derived extracellular vesicles comprise a lipid bilayer membrane comprising CD147. In some embodiments, less than about 30% of the megakaryocyte-derived extracellular vesicles comprise a lipid bilayer membrane comprising CD147. In some embodiments, less than about 25% of the megakaryocyte-derived extracellular vesicles comprise a lipid bilayer membrane comprising CD147. In some embodiments, less than about 20% of the megakaryocyte-derived extracellular vesicles comprise a lipid bilayer membrane comprising CD147. In some embodiments, less than about 15% of the megakaryocyte-derived extracellular vesicles comprise a lipid bilayer membrane comprising CD147. In some embodiments, less than about 10% of the megakaryocyte-derived extracellular vesicles comprise a lipid bilayer membrane comprising CD147. In some embodiments, less than about 5% of the megakaryocyte-derived extracellular vesicles comprise a lipid bilayer membrane comprising CD147. In some embodiments, less than about 1% of the megakaryocyte-derived extracellular vesicles comprise a lipid bilayer membrane comprising CD147.

In some embodiments, between about 1% to about 99% of the megakaryocyte-derived extracellular vesicles comprise a lipid bilayer membrane comprising CD147. In some embodiments, between about 1% to about 50% of the megakaryocyte-derived extracellular vesicles comprise a lipid bilayer membrane comprising CD147. In some embodiments, between about 1% to about 25% of the megakaryocyte-derived extracellular vesicles comprise a lipid bilayer membrane comprising CD147. In some embodiments, between about 1% to about 10% of the megakaryocyte-derived extracellular vesicles comprise a lipid bilayer membrane comprising CD147. In some embodiments, between about 1% to about 5% of the megakaryocyte-derived extracellular vesicles comprise a lipid bilayer membrane comprising CD147. In some embodiments, between about 1% to about 2% of the megakaryocyte-derived extracellular vesicles comprise a lipid bilayer membrane comprising CD147. In some embodiments, between about 50% to about 99% of the megakaryocyte-derived extracellular vesicles comprise a lipid bilayer membrane comprising CD147. In some embodiments, between about 75% to about 99% of the megakaryocyte-derived extracellular vesicles comprise a lipid bilayer membrane comprising CD147. In some embodiments, between about 90% to about 99% of the megakaryocyte-derived extracellular vesicles comprise a lipid bilayer membrane comprising CD147. In some embodiments, between about 95% to about 99% of the megakaryocyte-derived extracellular vesicles comprise a lipid bilayer membrane comprising CD147.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD147.

In some embodiments, between about 1% to about 15% of the megakaryocyte-derived extracellular vesicles comprise a lipid bilayer membrane comprising CD147. In some embodiments, between about 1% to about 10% of the megakaryocyte-derived extracellular vesicles comprise a lipid bilayer membrane comprising CD147. In some embodiments, between about 3% to about 8% of the megakaryocyte-derived extracellular vesicles comprise a lipid bilayer membrane comprising CD147. In some embodiments, between about 4% to about 7% of the megakaryocyte-derived extracellular vesicles comprise a lipid bilayer membrane comprising CD147.

In embodiments, the megakaryocyte-derived extracellular vesicles are characterized by a higher expression and/or presence of CD147 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD147 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD147 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD147 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 2-fold to about an 8-fold, or about a 2-fold to about a 4-fold lower amount of CD147 than platelet free plasma (PFP) MkEVs. In embodiments, the megakaryocyte-derived extracellular vesicles have about a 2-fold or about a 3-fold lower amount of CD147 than platelet free plasma (PFP) MkEVs. In embodiments, the megakaryocyte-derived extracellular vesicles have about a 1.1-fold to about a 2-fold lower amount of CD147 than platelet derived extracellular vesicles (PLT EVs). In embodiments, the megakaryocyte-derived extracellular vesicles have about a 1.1-fold or about a 1.2-fold lower amount of CD147 than platelet derived extracellular vesicles (PLT EVs). In embodiments, the megakaryocyte-derived extracellular vesicles have an amount of CD147 that is substantially the same as platelet derived extracellular vesicles (PLT EVs).

In embodiments, greater than about 50% of the megakaryocyte-derived extracellular vesicles comprise a lipid bilayer membrane comprising CD32a. In some embodiments, greater than about 40% of the megakaryocyte-derived extracellular vesicles comprise a lipid bilayer membrane comprising CD32a. In some embodiments, greater than about 60% of the megakaryocyte-derived extracellular vesicles comprise a lipid bilayer membrane comprising CD32a. In some embodiments, greater than about 70% of the megakaryocyte-derived extracellular vesicles comprise a lipid bilayer membrane comprising CD32a. In some embodiments, greater than about 80% of the megakaryocyte-derived extracellular vesicles comprise a lipid bilayer membrane comprising CD32a. In some embodiments, greater than about 90% of the megakaryocyte-derived extracellular vesicles comprise a lipid bilayer membrane comprising CD32a. In some embodiments, greater than about 95% of the megakaryocyte-derived extracellular vesicles comprise a lipid bilayer membrane comprising CD32a. In some embodiments, greater than about 99% of the megakaryocyte-derived extracellular vesicles comprise a lipid bilayer membrane comprising CD32a.

In embodiments, about 50% or less of the megakaryocyte-derived extracellular vesicles comprise a lipid bilayer membrane comprising CD32a. In some embodiments, about 40% or less of the megakaryocyte-derived extracellular vesicles comprise a lipid bilayer membrane comprising CD32a. In some embodiments, about 60% or less of the megakaryocyte-derived extracellular vesicles comprise a lipid bilayer membrane comprising CD32a. In some embodiments, about 70% or less of the megakaryocyte-derived extracellular vesicles comprise a lipid bilayer membrane comprising CD32a. In some embodiments, about 80% or less of the megakaryocyte-derived extracellular vesicles comprise a lipid bilayer membrane comprising CD32a. In some embodiments, about 90% or less of the megakaryocyte-derived extracellular vesicles comprise a lipid bilayer membrane comprising CD32a. In some embodiments, about 95% or less of the megakaryocyte-derived extracellular vesicles comprise a lipid bilayer membrane comprising CD32a. In some embodiments, about 99% or less of the megakaryocyte-derived extracellular vesicles comprise a lipid bilayer membrane comprising CD32a.

In some embodiments, less than about 50% of the megakaryocyte-derived extracellular vesicles comprise a lipid bilayer membrane comprising CD32a. In embodiments, less than about 40% of the megakaryocyte-derived extracellular vesicles comprise a lipid bilayer membrane comprising CD32a. In some embodiments, less than about 30% of the megakaryocyte-derived extracellular vesicles comprise a lipid bilayer membrane comprising CD32a. In some embodiments, less than about 25% of the megakaryocyte-derived extracellular vesicles comprise a lipid bilayer membrane comprising CD32a. In some embodiments, less than about 20% of the megakaryocyte-derived extracellular vesicles comprise a lipid bilayer membrane comprising CD32a. In some embodiments, less than about 15% of the megakaryocyte-derived extracellular vesicles comprise a lipid bilayer membrane comprising CD32a. In some embodiments, less than about 10% of the megakaryocyte-derived extracellular vesicles comprise a lipid bilayer membrane comprising CD32a. In some embodiments, less than about 5% of the megakaryocyte-derived extracellular vesicles comprise a lipid bilayer membrane comprising CD32a. In some embodiments, less than about 1% of the megakaryocyte-derived extracellular vesicles comprise a lipid bilayer membrane comprising CD32a.

In some embodiments, between about 1% to about 99% of the megakaryocyte-derived extracellular vesicles comprise a lipid bilayer membrane comprising CD32a. In some embodiments, between about 1% to about 50% of the megakaryocyte-derived extracellular vesicles comprise a lipid bilayer membrane comprising CD32a. In some embodiments, between about 1% to about 25% of the megakaryocyte-derived extracellular vesicles comprise a lipid bilayer membrane comprising CD32a. In some embodiments, between about 1% to about 10% of the megakaryocyte-derived extracellular vesicles comprise a lipid bilayer membrane comprising CD32a. In some embodiments, between about 1% to about 5% of the megakaryocyte-derived extracellular vesicles comprise a lipid bilayer membrane comprising CD32a. In some embodiments, between about 1% to about 2% of the megakaryocyte-derived extracellular vesicles comprise a lipid bilayer membrane comprising CD32a. In some embodiments, between about 50% to about 99% of the megakaryocyte-derived extracellular vesicles comprise a lipid bilayer membrane comprising CD32a. In some embodiments, between about 75% to about 99% of the megakaryocyte-derived extracellular vesicles comprise a lipid bilayer membrane comprising CD32a. In some embodiments, between about 90% to about 99% of the megakaryocyte-derived extracellular vesicles comprise a lipid bilayer membrane comprising CD32a. In some embodiments, between about 95% to about 99% of the megakaryocyte-derived extracellular vesicles comprise a lipid bilayer membrane comprising CD32a.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising CD32a.

In embodiments, the megakaryocyte-derived extracellular vesicles are free of, or substantially free of CD32a.

In embodiments, the megakaryocyte-derived extracellular vesicles are characterized by a higher expression and/or presence of CD32a than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD32a than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of CD32a than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD32a than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about a 50-fold to about 100-fold, 128-fold to about a 512-fold, or about a 256-fold to about a 512-fold, or about a 250-fold to about a 300-fold lower amount of CD32a than platelet free plasma (PFP) MkEVs. In embodiments, the megakaryocyte-derived extracellular vesicles have about a 250-fold or about a 256-fold lower amount of CD32a than platelet free plasma (PFP) MkEVs. In embodiments, the megakaryocyte-derived extracellular vesicles have about a 250-fold to about a 400-fold, or a 256-fold to about a 512-fold lower amount of CD32a than platelet derived extracellular vesicles (PLT EVs). In embodiments, the megakaryocyte-derived extracellular vesicles have about a 256-fold or about a 300-fold lower amount of CD32a than platelet derived extracellular vesicles (PLT EVs).

In embodiments, greater than about 50% of the megakaryocyte-derived extracellular vesicles comprise a lipid bilayer membrane comprising GPVI. In some embodiments, greater than about 40% of the megakaryocyte-derived extracellular vesicles comprise a lipid bilayer membrane comprising GPVI. In some embodiments, greater than about 60% of the megakaryocyte-derived extracellular vesicles comprise a lipid bilayer membrane comprising GPVI. In some embodiments, greater than about 70% of the megakaryocyte-derived extracellular vesicles comprise a lipid bilayer membrane comprising GPVI a. In some embodiments, greater than about 80% of the megakaryocyte-derived extracellular vesicles comprise a lipid bilayer membrane comprising GPVI. In some embodiments, greater than about 90% of the megakaryocyte-derived extracellular vesicles comprise a lipid bilayer membrane comprising GPVI. In some embodiments, greater than about 95% of the megakaryocyte-derived extracellular vesicles comprise a lipid bilayer membrane comprising GVPI. In some embodiments, greater than about 99% of the megakaryocyte-derived extracellular vesicles comprise a lipid bilayer membrane comprising GVPI.

In embodiments, about 50% or less of the megakaryocyte-derived extracellular vesicles comprise a lipid bilayer membrane comprising GVPI. In some embodiments, about 40% or less of the megakaryocyte-derived extracellular vesicles comprise a lipid bilayer membrane comprising GVPI. In some embodiments, about 60% or less of the megakaryocyte-derived extracellular vesicles comprise a lipid bilayer membrane comprising GVPI. In some embodiments, about 70% or less of the megakaryocyte-derived extracellular vesicles comprise a lipid bilayer membrane comprising GVPI. In some embodiments, about 80% or less of the megakaryocyte-derived extracellular vesicles comprise a lipid bilayer membrane comprising GVPI. In some embodiments, about 90% or less of the megakaryocyte-derived extracellular vesicles comprise a lipid bilayer membrane comprising GVPI. In some embodiments, about 95% or less of the megakaryocyte-derived extracellular vesicles comprise a lipid bilayer membrane comprising GVPI. In some embodiments, about 99% or less of the megakaryocyte-derived extracellular vesicles comprise a lipid bilayer membrane comprising GVPI.

In some embodiments, less than about 50% of the megakaryocyte-derived extracellular vesicles comprise a lipid bilayer membrane comprising GVPI. In embodiments, less than about 40% of the megakaryocyte-derived extracellular vesicles comprise a lipid bilayer membrane comprising GVPI. In some embodiments, less than about 30% of the megakaryocyte-derived extracellular vesicles comprise a lipid bilayer membrane comprising GVPI. In some embodiments, less than about 25% of the megakaryocyte-derived extracellular vesicles comprise a lipid bilayer membrane comprising GVPI. In some embodiments, less than about 20% of the megakaryocyte-derived extracellular vesicles comprise a lipid bilayer membrane comprising GVPI. In some embodiments, less than about 15% of the megakaryocyte-derived extracellular vesicles comprise a lipid bilayer membrane comprising GVPI. In some embodiments, less than about 10% of the megakaryocyte-derived extracellular vesicles comprise a lipid bilayer membrane comprising GVPI. In some embodiments, less than about 5% of the megakaryocyte-derived extracellular vesicles comprise a lipid bilayer membrane comprising GVPI. In some embodiments, less than about 1% of the megakaryocyte-derived extracellular vesicles comprise a lipid bilayer membrane comprising GVPI.

In some embodiments, between about 1% to about 99% of the megakaryocyte-derived extracellular vesicles comprise a lipid bilayer membrane comprising GVPI. In some embodiments, between about 1% to about 50% of the megakaryocyte-derived extracellular vesicles comprise a lipid bilayer membrane comprising GVPI. In some embodiments, between about 1% to about 25% of the megakaryocyte-derived extracellular vesicles comprise a lipid bilayer membrane comprising GVPI. In some embodiments, between about 1% to about 10% of the megakaryocyte-derived extracellular vesicles comprise a lipid bilayer membrane comprising GVPI. In some embodiments, between about 1% to about 5% of the megakaryocyte-derived extracellular vesicles comprise a lipid bilayer membrane comprising GVPI. In some embodiments, between about 1% to about 2% of the megakaryocyte-derived extracellular vesicles comprise a lipid bilayer membrane comprising GVPI. In some embodiments, between about 50% to about 99% of the megakaryocyte-derived extracellular vesicles comprise a lipid bilayer membrane comprising GVPI. In some embodiments, between about 75% to about 99% of the megakaryocyte-derived extracellular vesicles comprise a lipid bilayer membrane comprising GVPI. In some embodiments, between about 90% to about 99% of the megakaryocyte-derived extracellular vesicles comprise a lipid bilayer membrane comprising GVPI. In some embodiments, between about 95% to about 99% of the megakaryocyte-derived extracellular vesicles comprise a lipid bilayer membrane comprising GVPI.

In some embodiments, less than about 1%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or greater than about 99% of the megakaryocyte-derived extracellular vesicles comprise a lipid bilayer membrane comprising GVPI.

In embodiments, the megakaryocyte-derived extracellular vesicles are characterized by a higher expression and/or presence of GPVI than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of GPVI than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by a lower expression and/or presence of GPVI than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of GPVI than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles have about an 8-fold to about a 64-fold, or about a 16-fold to about a 32-fold greater amount of GPVI than platelet free plasma (PFP) MkEVs. In embodiments, the megakaryocyte-derived extracellular vesicles have about a 30-fold or about a 32-fold greater amount of GPVI than platelet free plasma (PFP) MkEVs. In embodiments, the megakaryocyte-derived extracellular vesicles have about a 2-fold to about a 16-fold, or about a 4-fold to about an 8-fold lower amount of GPVI than platelet derived extracellular vesicles (PLT EVs). In embodiments, the megakaryocyte-derived extracellular vesicles have about a 4-fold or about a 5-fold lower amount of GPVI than platelet derived extracellular vesicles (PLT EVs).

In embodiments, the megakaryocyte-derived extracellular vesicles are free of, or substantially free of LAMP-1 (CD107A). In embodiments, the megakaryocyte-derived extracellular vesicles have less LAMP-1 (CD107A) than naturally-occurring megakaryocyte-derived extracellular vesicles and/or vesicles or extracellular vesicles derived from platelets.

In embodiments, less than about 20%, or less than about 15%, or less than about 10%, or less than about 5% of the megakaryocyte-derived extracellular vesicles comprise a lipid bilayer membrane comprising LAMP-1 (CD107A).

In embodiments, the megakaryocyte-derived extracellular vesicles are characterized by having CD62P and being free of, or substantially free of LAMP-1 (CD107A).

In embodiments, the megakaryocyte-derived extracellular vesicles are characterized by a population of megakaryocyte-derived extracellular vesicles wherein less than about 20%, or less than about 15%, or less than about 10%, or less than about 5% of the megakaryocyte-derived extracellular vesicles comprise a lipid bilayer membrane comprising LAMP-1 (CD107A) and greater than about 40%, greater than about 50%, greater than about 60%, greater than about 70%, greater than about 80%, greater than about 90%, greater than about 95%, or greater than about 99% comprises a lipid bilayer membrane comprising CD62P.

In some embodiments, less than about 70%, or less than about 60%, or less than about 50%, less than about 40%, less than about 30%, less than about 20%, less than about 15%, less than about 10%, less than about 5%, or less than about 1% of the megakaryocyte-derived extracellular vesicles comprise a lipid bilayer membrane comprising phosphatidylserine (PS).

In embodiments, the megakaryocyte-derived extracellular vesicles are characterized by a lower expression and/or presence of phosphatidylserine (PS) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of phosphatidylserine (PS) than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles.

In embodiments, the megakaryocyte-derived extracellular vesicles are characterized by being free of, or substantially free of phosphatidylserine (PS).

In some embodiments, the megakaryocyte-derived extracellular vesicles are characterized by a population of megakaryocyte-derived extracellular vesicles wherein less than about 50%, less than about 40%, less than about 30%, less than about 20%, less than about 15%, less than about 10%, less than about 5%, or less than about 1% of the megakaryocyte-derived extracellular vesicles comprise a lipid bilayer membrane comprising phosphatidylserine (PS), and greater than about 40%, greater than about 50%, greater than about 60%, greater than about 70%, greater than about 80%, greater than about 90%, greater than about 95%, or greater than about 99% of the megakaryocyte-derived extracellular vesicles comprise a lipid bilayer membrane comprising CD47.

In some embodiments, the megakaryocyte-derived extracellular vesicles are characterized by a population of megakaryocyte-derived extracellular vesicles wherein about 20% to about 40% of the megakaryocyte-derived extracellular vesicles comprise a lipid bilayer membrane comprising and/or test positive for phosphatidylserine (PS), about 80% to about 99%, or about 85% to about 99% of the megakaryocyte-derived extracellular vesicles comprise a lipid bilayer membrane comprising CD61, and about 25% to about 55%, or about 35% to about 55% of the megakaryocyte-derived extracellular vesicles comprise a lipid bilayer membrane comprising CD9.

In embodiments, the megakaryocyte-derived extracellular vesicles are characterized by a higher expression and/or presence or CD41 than naturally-occurring meg akaryocyte-derived extracellular vesicles and/or vesicles or extracellular vesicles derived from platelets. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of CD41 than naturally-occurring megakaryocyte-derived extracellular vesicles and/or vesicles or extracellular vesicles derived from platelets.

In embodiments, the megakaryocyte-derived extracellular vesicles are characterized by a lower expression and/or presence or CD41 than naturally-occurring meg akaryocyte-derived extracellular vesicles and/or vesicles or extracellular vesicles derived from platelets. In embodiments, the megakaryocyte-derived extracellular vesicles have about a 2-fold, or about a 10-fold, or about a 50-fold, or about a 100-fold, or about a 300-fold, or about a 500-fold, or about a 1000-fold lower amount of CD41 than naturally-occurring megakaryocyte-derived extracellular vesicles and/or vesicles or extracellular vesicles derived from platelets.

In embodiments, the megakaryocyte-derived extracellular vesicles contain full-length filamin A.

In embodiments, the megakaryocyte-derived extracellular vesicles comprise a lipid bilayer membrane that comprises phosphatidylserine. In embodiments, the megakaryocyte-derived extracellular vesicles are characterized by a population of megakaryocyte-derived extracellular vesicles of which greater than about 40%, greater than about 50%, greater than about 60%, greater than about 70%, greater than about 80%, greater than about 90%, greater than about 95%, or greater than about 99% comprises a lipid bilayer membrane that comprises phosphatidylserine.

In embodiments, the megakaryocyte-derived extracellular vesicles comprise a lipid bilayer membrane positive for Annexin V. For instance, Annexin V, which interacts with phosphatidylserine (PS), can be used as a surrogate for phosphatidylserine expression and/or presence or absence. In embodiments, the megakaryocyte-derived extracellular vesicles are characterized by a population of megakaryocyte-derived extracellular vesicles of which greater than about 40%, greater than about 50%, greater than about 60%, greater than about 70%, greater than about 80%, greater than about 90%, or greater than about 95% are positive for PS.

In some embodiments, the megakaryocyte-derived extracellular vesicles are characterized by a population of megakaryocyte-derived extracellular vesicles of which about 20% to about 40% comprises a lipid bilayer membrane that comprises phosphatidylserine and/or are positive for phosphatidylserine.

In some embodiments, substantially all of the megakaryocyte-derived extracellular vesicles in the population comprise 2, 3, 4, 5, 6, 7, or 8 of Phosphatidylserine (PS), CD62P, LAMP-1 (CD107a), CD42b, CD9, CD43, CD31, and CD11b. In some embodiments, substantially all of the megakaryocyte-derived extracellular vesicles in the population comprise 2, 3, or 4 of PS, CD62P, CD9, and CD11b. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of one or more of Phosphatidylserine (PS), CD62P, LAMP-1 (CD107a), CD42b, CD9, CD43, CD31, and CD11b than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In some embodiments, the megakaryocyte-derived extracellular vesicles are characterized by not expressing a substantial amount of DRAQ5. In some embodiments, the megakaryocyte-derived extracellular vesicles are characterized by being substantially free of DRAQ5.

In some embodiments, substantially all of the megakaryocyte-derived extracellular vesicles in the population comprise 2, 3, 4, 5, or 6 of Phosphatidylserine (PS), CD61, CD62P, LAMP-1 (CD107a), CLEC-2, and CD63. In some embodiments, substantially all of the megakaryocyte-derived extracellular vesicles in the population comprise 2 or 3 of PS, CD61, and CD63. In some embodiments, substantially all of the megakaryocyte-derived extracellular vesicles in the population comprise Phosphatidylserine (PS) and CD61. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of one or more of Phosphatidylserine (PS), CD61, CD62P, LAMP-1 (CD107a), CLEC-2, and CD63 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In some embodiments, the megakaryocyte-derived extracellular vesicles are characterized by not expressing a substantial amount of DRAQ5. In some embodiments, the megakaryocyte-derived extracellular vesicles are characterized by being substantially free of DRAQ5.

In some embodiments, substantially all of the megakaryocyte-derived extracellular vesicles in the population comprise 2, 3, 4, 5, 6, 7, or 8 of Phosphatidylserine (PS), CD62P, CLEC-2, CD9, CD31, CD147, CD32a, and GPVI. In some embodiments, substantially all of the megakaryocyte-derived extracellular vesicles in the population comprise 2, 3, or 4 of Phosphatidylserine (PS), CD9, CD31, and CD147. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of one or more of Phosphatidylserine (PS), CD62P, CLEC-2, CD9, CD31, CD147, CD32a, and GPVI than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In some embodiments, the megakaryocyte-derived extracellular vesicles are characterized by not expressing a substantial amount of DRAQ5. In some embodiments, the megakaryocyte-derived extracellular vesicles are characterized by being substantially free of DRAQ5.

In some embodiments, substantially all of the megakaryocyte-derived extracellular vesicles in the population comprise 2, 3, 4, 5, of 6 of Phosphatidylserine (PS), CD62P, LAMP-1 (CD107a), CLEC-2, CD9, and CD31. In some embodiments, substantially all of the megakaryocyte-derived extracellular vesicles in the population comprise 2 or 3 of Phosphatidylserine (PS), CD62P, and CD9. In some embodiments, substantially all of the megakaryocyte-derived extracellular vesicles in the population comprise PS and CD9. In embodiments, the megakaryocyte-derived extracellular vesicles have about a 2-fold, or about a 10-fold, or about a 50-fold, or about a 100-fold, or about a 300-fold, or about a 500-fold, or about a 1000-fold greater amount of one or more of Phosphatidylserine (PS), CD62P, LAMP-1 (CD107a), CLEC-2, CD9, and CD31 than naturally-occurring megakaryocyte-derived extracellular vesicles, vesicles or extracellular vesicles derived from platelets such as platelet derived extracellular vesicles (PLT EVs), and/or platelet-free plasma (PPF) megakaryocyte-derived extracellular vesicles. In some embodiments, the megakaryocyte-derived extracellular vesicles are characterized by not expressing a substantial amount of DRAQ5. In some embodiments, the megakaryocyte-derived extracellular vesicles are characterized by being substantially free of DRAQ5.

In some embodiments, the megakaryocyte-derived extracellular vesicles and/or plurality of megakaryocyte-derived extracellular vesicles and/or population of megakaryocyte-derived extracellular vesicles comprise a lipid bilayer membrane, wherein less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD54, and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD18 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD43 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD11b and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD62P and/or greater than about 40%, or greater than about 50%, or greater than about 60%, or greater than about 70%, or greater than about 80%, or greater than about 90%, greater than about 95%, or greater than about 99% of the megakaryocyte-derived extracellular vesicles comprise a lipid bilayer membrane comprising CD41 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD21 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD51 and/or greater than about 40%, or greater than about 50%, or greater than about 60%, or greater than about 70%, or greater than about 80%, or greater than about 90%, greater than about 95%, or greater than about 99% of the megakaryocyte-derived extracellular vesicles comprise a lipid bilayer membrane comprising CD61 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD147 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD31 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD47 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD32a and/or greater than about 40%, or greater than about 50%, or greater than about 60%, or greater than about 70%, or greater than about 80%, or greater than about 90%, greater than about 95%, or greater than about 99% of the megakaryocyte-derived extracellular vesicles comprise a lipid bilayer membrane comprising CD9 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CLEC-2 and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising LAMP-1 (CD107a) and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD24b and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising GVPI and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising CD63, and/or less than about 50%, or less than about 40%, or less than about 30%, or less than about 20%, or less than about 10%, or less than about 5% or less than about 1% of the megakaryocyte-derived extracellular vesicles comprise a lipid bilayer membrane comprising phosphatidylserine (PS). In some embodiments, greater than about 40%, greater than about 50%, or greater than about 60%, or greater than about 70%, or greater than about 80%, or greater than about 90%, greater than about 95%, or greater than about 99% of the megakaryocyte-derived extracellular vesicles and/or plurality of megakaryocyte-derived extracellular vesicles and/or population of megakaryocyte-derived extracellular vesicles comprise a lipid bilayer membrane comprising CD41.

Size Profile or Fingerprint

In various embodiments, the megakaryocyte-derived extracellular vesicles of the disclosure are characterized by a unique size (e.g. vesicle diameter) profile or fingerprint that distinguishes them from, for instance, naturally-occurring megakaryocyte-derived extracellular vesicles and/or vesicles or extracellular vesicles derived from platelets. In various embodiments, the present megakaryocyte-derived extracellular vesicles are characterized by a such a size profile or fingerprint, which favors larger particles, e.g. as compared to naturally-occurring megakaryocyte-derived extracellular vesicles and/or vesicles or extracellular vesicles derived from platelets, that are desirable for, e.g., their higher carrying capacity.

In various embodiments, the present megakaryocyte-derived extracellular vesicles are characterized by a bias for particles of about 30 nm to about 100 nm.

In various embodiments, the present megakaryocyte-derived extracellular vesicles are characterized by a bias for particles of about 30 nm to about 400 nm.

In various embodiments, the present megakaryocyte-derived extracellular vesicles are characterized by a bias for particles of about 100 nm to about 200 nm.

In various embodiments, the present megakaryocyte-derived extracellular vesicles are characterized by a bias for particles of about 100 nm to about 300 nm.

In various embodiments, the present megakaryocyte-derived extracellular vesicles are characterized by a bias for particles of about 100 nm to about 500 nm.

In various embodiments, the present megakaryocyte-derived extracellular vesicles are characterized by a bias for particles of about 100 nm to about 600 nm.

In various embodiments, the present megakaryocyte-derived extracellular vesicles are characterized by a bias for particles of about 200 nm in diameter, on average.

In various embodiments, the present megakaryocyte-derived extracellular vesicles are characterized by a bias for particles of about 250 nm in diameter, on average.

In embodiments, the megakaryocyte-derived extracellular vesicles are substantially of a diameter of less than about 100 nm. In embodiments, the megakaryocyte-derived extracellular vesicles are substantially of a diameter in the range between about 30 nm to about 300 nm. In embodiments, the megakaryocyte-derived extracellular vesicles are substantially of a diameter in the range between about 30 nm to about 400 nm. In embodiments, the megakaryocyte-derived extracellular vesicles are substantially of a diameter in the range between about 100 nm to about 300 nm. In embodiments, the megakaryocyte-derived extracellular vesicles are substantially of a diameter in the range between about 200 nm to about 300 nm. In embodiments, the megakaryocyte-derived extracellular vesicles are substantially of a diameter in the range between about 300 nm to about 400 nm. In embodiments, the megakaryocyte-derived extracellular vesicles are substantially of a diameter in the range between about 400 nm to about 500 nm. In embodiments, the megakaryocyte-derived extracellular vesicles are substantially of a diameter in the range between about 500 nm to about 600 nm. In embodiments, the megakaryocyte-derived extracellular vesicles are substantially of a diameter in the range between about 600 nm to about 700 nm. In embodiments, the megakaryocyte-derived extracellular vesicles are substantially of a diameter in the range between about 700 nm to about 800 nm. In embodiments, the megakaryocyte-derived extracellular vesicles are substantially of a diameter in the range between about 800 nm to about 900 nm. In embodiments, the megakaryocyte-derived extracellular vesicles are substantially of a diameter in the range between about 900 nm to about 1000 nm. In embodiments, the megakaryocyte-derived extracellular vesicles are substantially of a diameter in the range between about 500 nm to about 1000 nm. In embodiments, the megakaryocyte-derived extracellular vesicles are substantially of a diameter in the range between about 600 nm to about 1000 nm. In embodiments, the megakaryocyte-derived extracellular vesicles are substantially of a diameter in the range between about 100 nm to about 500 nm. In embodiments, the megakaryocyte-derived extracellular vesicles are substantially of a diameter in the range between about 100 nm to about 600 nm. In embodiments, the megakaryocyte-derived extracellular vesicles are substantially of a diameter in the range between about 150 nm to about 500 nm. In embodiments, the megakaryocyte-derived extracellular vesicles are substantially of a diameter in the range between about 100 nm to about 200 nm. In embodiments, the megakaryocyte-derived extracellular vesicles are substantially of a diameter in the range between about 100 nm to about 200 nm. In embodiments, the megakaryocyte-derived extracellular vesicles are substantially of a diameter in the range between about 200 nm to about 600 nm. In some embodiments, the megakaryocyte-derived extracellular vesicles are substantially of a diameter in the range between about 30 nm to 100 nm, or between about 30 nm to 400 nm, or between about 100 nm to about 200 nm, or between about 100 nm to about 500 nm, or between about 200 nm to about 350 nm, or between about 400 nm to about 600 nm.

In embodiments, about 90% or more, or about 95% or more, or about 97% or more, or about 99% or more of the megakaryocyte-derived extracellular vesicles are of a diameter of between about 30 to 100 nm.

In embodiments, about 90% or more, or about 95% or more, or about 97% or more, or about 99% or more of the megakaryocyte-derived extracellular vesicles are of a diameter of between about 30 to 400 nm.

In embodiments, about 90% or more, or about 95% or more, or about 97% or more, or about 99% or more of the megakaryocyte-derived extracellular vesicles are of a diameter of between about 100 nm to about 200 nm.

In embodiments, about 90% or more, or about 95% or more, or about 97% or more, or about 99% or more of the megakaryocyte-derived extracellular vesicles are of a diameter of between about 100 nm to about 300 nm.

In some embodiments, about 90% or more, or about 95% or more, or about 97% or more, or about 99% or more of the megakaryocyte-derived extracellular vesicles are of a diameter of between about 200 nm to about 350 nm.

In some embodiments, about 90% or more, or about 95% or more, or about 97% or more, or about 99% or more of the megakaryocyte-derived extracellular vesicles are of a diameter of between about 100 nm to about 600 nm.

In some embodiments, about 90% or more, or about 95% or more, or about 97% or more, or about 99% or more of the megakaryocyte-derived extracellular vesicles are of a diameter of between about 400 nm to about 600 nm.

In some embodiments, about 90% or more, or about 95% or more, or about 97% or more, or about 99% or more of the megakaryocyte-derived extracellular vesicles are of a diameter of between about 200 nm to about 600 nm.

In some embodiments, about 90% or more, or about 95% or more, or about 97% or more, or about 99% or more of the megakaryocyte-derived extracellular vesicles are of a diameter of between about 30 to about 100 nm and/or about 30 to about 400 nm and/or about 100 nm to about 200 nm and/or about 100 nm to about 300 nm and/or between about 200 nm to about 350 nm and/or between about 400 nm to about 600 nm.

In embodiments, the megakaryocyte-derived extracellular vesicles of the disclosure comprise various subpopulations of vesicles of different diameter. For example, in embodiments, megakaryocyte-derived extracellular vesicles of the disclosure comprise one or more of (e.g. one, or two, or three, or four of): a subpopulation of about 50 nm in diameter, a subpopulation of about 150 nm in diameter, a subpopulation of about 200 nm in diameter, a subpopulation of about 250 nm in diameter, a subpopulation of about 300 nm in diameter, a subpopulation of about 400 nm in diameter, a subpopulation of about 500 nm in diameter and a subpopulation of about 600 nm in diameter. In embodiments, megakaryocyte-derived extracellular vesicles of the disclosure comprise one or more of (e.g. one, or two, or three, or four of): a subpopulation of about 45 nm in diameter, a subpopulation of about 135 nm in diameter, a subpopulation of about 285 nm in diameter, and a subpopulation of about 525 nm in diameter.

In some embodiments, about 90% or more, or about 95% or more, or about 97% or more, or about 99% or more of the megakaryocyte-derived extracellular vesicles are of about 50 nm in diameter and/or about 150 nm in diameter and/or about 300 nm in diameter and/or about 500 nm in diameter.

In some embodiments, the population of megakaryocyte-derived extracellular vesicles exhibits the following characteristics:

a) about 80% or more, about 85% or more, about 90% or more, about 95% or more, about 97% or more, or about 99% or more of the megakaryocyte-derived extracellular vesicles in the population are substantially free of nuclei;

b) about 90% or more, or about 95% or more, or about 97% or more, or about 99% or more of the megakaryocyte-derived extracellular vesicles are of a diameter of between about 100 nm to about 600 nm.;

c) about 40% or more, about 50% or more, about 60% or more, about 70% or more, about 80% or more, or about 90% or more of the megakaryocyte-derived extracellular vesicles in the population comprise CD41; and d) the population comprises about $1 \times 10^7$ or more, about $1.5 \times 10^7$ or more, about $5 \times 10^7$ or more, about $1 \times 10^8$ or more, about $1.5 \times 10^8$ or more, about $5 \times 10^8$ or more, about $1 \times 10^9$ or more, about 9 or more, about $1 \times 10^{10}$ or more, or about $1 \times 10^{10}$ or more megakaryocyte-derived extracellular vesicles.

In some embodiments, the population of megakaryocyte-derived extracellular vesicles exhibits the following characteristics:

a) about 80% or more, about 85% or more, about 90% or more, about 95% or more, about 97% or more, or about 99% or more of the megakaryocyte-derived extracellular vesicles in the population are substantially free of nuclei;

b) about 90% or more, or about 95% or more, or about 97% or more, or about 99% or more of the megakaryocyte-derived extracellular vesicles are of a diameter of between about 100 nm to about 600 nm.;

c) about 40% or more, about 50% or more, about 60% or more, about 70% or more, about 80% or more, or about 90% or more of the megakaryocyte-derived extracellular vesicles in the population comprise CD61; and d) the population comprises about $1 \times 10^7$ or more, about $1.5 \times 10^7$ or more, about $5 \times 10^7$ or more, about $1 \times 10^8$ or more, about $1.5 \times 10^8$ or more, about $5 \times 10^8$ or more, about $1 \times 10^9$ or more, about $5 \times 10^9$ or more, about $1 \times 10^{10}$ or more, or about $1 \times 10^{10}$ or more megakaryocyte-derived extracellular vesicles.

Any method for determining the amount of nuclei in the population of megakaryocyte-derived extracellular vesicles is contemplated by the present disclosure. Non-limiting examples of methods include staining the megakaryocyte-derived extracellular vesicles with a nuclear stain such as DRAQ5, wherein a lack of staining indicates that the megakaryocyte-derived extracellular vesicles are substantially free of nuclei.

Sources and Characterization of Megakaryocyte-Derived Extracellular Vesicles

Megakaryocytes are large, polyploid cells derived from hematopoietic stem and progenitor cells, contained within the CD34$^+$-cell compartment. In embodiments, the mega-karyocyte is characterized by the expression and/or presence of one or more of CD41, CD62P, GPVI, CLEC-2, CD42b and CD61. In embodiments, the megakaryocyte is one or more of CD42b+, CD61+, and DNA+. One morphological characteristic of mature megakaryocytes is the development of a large, multi-lobed nucleus. Mature megakaryocytes can stop proliferating, but continue to increase their DNA content through endomitosis, with a parallel increase in cell size.

In some embodiments, in addition to extracellular vesicles, megakaryocytes can shed pre- and proplatelets and platelet-like particles. These shed moieties can mature into platelets. In some embodiments, the pre- and proplatelets and platelet-like particles are all different products, which can be differentiated by size, morphology, biomarker expression and/or presence, and function.

Megakaryocytes are derived from pluripotent hematopoietic stem cell (HSC) precursors. HSCs are produced primarily by the liver, kidney, spleen, and bone marrow and are capable of producing a variety of blood cells depending on the signals they receive.

Thrombopoietin (TPO) is a primary signal for inducing an HSC to differentiate into a megakaryocyte. Other molecular signals for inducing megakaryocyte differentiation include granulocyte-macrophage colony-stimulating factor (GM-CSF), Interleukin-3 (IL-3), IL-6, IL-11, SCF, fms-like tyrosine kinase 3 ligand (FLT3L), interleukin 9 (IL-9), and the like. Production details are also described elsewhere herein.

In some embodiments, the substantially purified megakaryocyte-derived extracellular vesicles are derived from a human pluripotent stem cell.

In embodiments, the human pluripotent stem cell is a primary CD34+ hematopoietic stem cell. In embodiments, the primary CD34+ hematopoietic stem cell is sourced from peripheral blood or cord blood. In embodiments, the peripheral blood is granulocyte colony-stimulating factor-mobilized adult peripheral blood (mPB). In some embodiments, the human pluripotent stem cell is an HSC produced by the liver, kidney, spleen, or bone marrow. In some embodiments, the HSC is produced by the liver. In some embodiments, the HSC is produced by the kidney. In some embodiments, the HSC is produced by the spleen. In some embodiments, the HSC is produced by the bone marrow. In some embodiments, the HSC is induced to differentiate into a megakaryocyte by receiving a molecular signal selected from one or more of TPO, GM-CSF, IL-3, IL-6, IL-11, SCF, Flt3L, IL-9, and the like. In some embodiments, the molecular signal is TPO. In some embodiments, the molecular signal is GM-CSF. In some embodiments, the molecular signal is IL-3. In some embodiments, the molecular signal is IL-6. In some embodiments, the molecular signal is IL-11. In some embodiments, the molecular signal is SCF. In some embodiments, the molecular signal is Flt3L. In some embodiments, the molecular signal is IL-9.

In some embodiments, the molecular signal is a chemokine.

In some embodiments, the molecular signal promotes cell fate decision toward megakaryopoiesis.

In some embodiments, the molecular signal is devoid of erythropoietin (EPO).

In embodiments, the human pluripotent stem cell is an embryonic stem cell (ESC). ESCs have the capacity to form cells from all three germ layers of the body, regardless of the method by which the ESCs are derived. ESCs are functionally stem cells that can have one or more of the following characteristics: (a) be capable of inducing teratomas when transplanted in immunodeficient mice; (b) be capable of differentiating to cell types of all three germ layers (i.e. ectodermal, mesodermal, and endodermal cell types); and (c) express one or more markers of embryonic stem cells (e.g., Oct 4, alkaline phosphatase. SSEA-3 surface antigen, SSEA-4 surface antigen, SSEA-5 surface antigen, Nanog, TRA-I-60, TRA-1-81, SOX2, REX1, and the like).

In embodiments, the human pluripotent stem cell is an induced pluripotent stem cell (iPCs). Mature differentiated cells can be reprogrammed and dedifferentiated into embryonic-like cells, with embryonic stem cell-like properties. iPSCs can be generated using fetal, postnatal, newborn, juvenile, or adult somatic cells. Fibroblast cells can be reversed into pluripotency via, for example, retroviral transduction of certain transcription factors, resulting in iPSs. In some embodiments, iPSs are generated from various tissues, including fibroblasts, keratinocytes, melanocyte blood cells, bone marrow cells, adipose cells, and tissue-resident progenitor cells. In some embodiments, iPSCs are generated via one or more reprogramming or Yamanaka factors, e.g. Oct3/4, Sox2, Klf4, and c-Myc. In certain embodiments, at least two, three, or four reprogramming factors are expressed in a somatic cell to reprogram the somatic cell.

Once a pluripotent cell has completed differentiation and become a mature megakaryocyte, it begins the process of producing platelets, which do not contain a nucleus and may be about 1-3 um in diameter. Megakaryocytes also produce extracellular vesicles.

In embodiments, the present megakaryocytes are induced to favor production of megakaryocyte-derived extracellular vesicles over platelets. That is, in embodiments, the present megakaryocytes produce substantially more megakaryocyte-derived extracellular vesicles than platelets. In embodiments, the megakaryocyte-derived extracellular vesicles of the disclosure are substantially free of platelets. In some embodiments, the megakaryocyte-derived extracellular vesicles of the disclosure contain less than about 10%, or less than about 7%, or less than about 5%, or less than about 3%, or less than about 2%, or less than about 1% platelets.

In embodiments, the megakaryocyte-derived extracellular vesicles of the disclosure are substantially free of extracellular vesicles derived from platelets. In some embodiments, the megakaryocyte-derived extracellular vesicles of the disclosure contain less than about 10%, or less than about 7%, or less than about 5%, or less than about 3%, or less than about 2%, or less than about 1% of extracellular vesicles derived from platelets.

In some embodiments, the megakaryocyte-derived extracellular vesicles of the disclosure are substantially free of organelles. Non-limiting examples of contaminating organelles include, but are not limited to, mitochondria, and nuclei. In some embodiments, the megakaryocyte-derived extracellular vesicles of the disclosure are substantially free of mitochondria. In some embodiments, the preparation comprising the megakaryocyte-derived extracellular vesicles of the disclosure is substantially free of exosomes. In some embodiments, megakaryocyte-derived extracellular vesicles of the disclosure comprise organelles.

In some embodiments, the megakaryocyte-derived extracellular vesicles of the disclosure are substantially free of nuclei. In some embodiments, about 80% to about 100%, about 85% to about 100%, about 90% to about 100%, or about 95% to about 100% of the megakaryocyte-derived extracellular vesicles in the population are substantially free of nuclei. In some embodiments, greater than about 80%, greater than about 85%, greater than about 90%, greater than about 95%, greater than about 99%, or about 100% of the megakaryocyte-derived extracellular vesicles in the population are substantially free of nuclei.

Targeting

Megakaryocyte-derived extracellular vesicles can home to a range of target cells. When megakaryocyte-derived extracellular vesicles bind to a target cell, they can release their cargo via various mechanisms of megakaryocyte-derived extracellular vesicle internalization by the target cell.

In embodiments, the megakaryocyte-derived extracellular vesicles are suitable for homing to bone marrow in vivo. In embodiments, the megakaryocyte-derived extracellular vesicles are suitable for homing to bone marrow in vitro. In some embodiments, the megakaryocyte-derived extracellular vesicles home in vivo to bone marrow with about a 2-fold, or about a 3-fold, or about a 4-fold, or about a 5-fold, or about a 6-fold, or about a 7-fold, or about a 8-fold, or about a 9-fold, or about a 10-fold greater specificity than to another cell type, or to another organ, or to all other cell types combined.

In some embodiments, the megakaryocyte-derived extracellular vesicles home in vivo to one or more myelopoeitic cells in bone marrow. In some embodiments, the one or more myelopoeitic cells are selected from myeloblasts, promyelocytes, neutrophilic myelocytes, eosinophilic myelocytes, neutrophilic metamyelocytes, eosinophilic metamyelocytes, neutrophilic band cells, eosinophilic band cells, segmented neutrophils, segmented eosinophils, segmented basophils, and mast cells. In some embodiments, the megakaryocyte-derived extracellular vesicles home in vivo to one or more erythropoietic cells in bone marrow. In some embodiments, the one or more erythropoietic cells are selected from pronormoblasts, basophilic normoblasts, polychromatic normoblasts, and orthochromatic normoblasts. In some embodiments, the megakaryocyte-derived extracellular vesicles home in vivo to one or more of plasma cells, reticular cells, lymphocytes, monocytes, and megakaryocytes.

In some embodiments, the megakaryocyte-derived extracellular vesicles home in vivo to one or more hematopoietic cells in bone marrow. In some embodiments, the megakaryocyte-derived extracellular vesicles home in vivo to one or more hematopoietic cells in bone marrow, e.g. thrombopoietic cells.

In some embodiments, the megakaryocyte-derived extracellular vesicles home in vivo to one or more hematopoietic stem cells in bone marrow.

In embodiments, the megakaryocyte-derived extracellular vesicles are suitable for homing to an HSC in vivo. In embodiments, the megakaryocyte-derived extracellular vesicles are suitable for homing to an HSC in vitro. In some embodiments, the megakaryocyte-derived extracellular vesicles home in vivo to an HSC with about a 2-fold greater specificity than to another cell type, or than to another organ, or than to all other cell types combined. In some embodiments, the megakaryocyte-derived extracellular vesicles home in vivo to an HSC with about a 3-fold greater specificity than to another cell type, or than to another organ, or than to all other cell types combined. In some embodiments, the megakaryocyte-derived extracellular vesicles home in vivo to an HSC with about a 4-fold greater specificity than to another cell type, or to another organ, or to all other cell types combined. In some embodiments, the megakaryocyte-derived extracellular vesicles home in vivo to an HSC with about a 5-fold greater specificity than to another cell type, or to another organ, or to all other cell types combined. In some embodiments, the megakaryocyte-derived extracellular vesicles home in vivo to an HSC with about a 6-fold greater specificity than to another cell type, or to another organ, or to all other cell types combined. In some embodiments, the megakaryocyte-derived extracellular vesicles home in vivo to an HSC with about a 7-fold greater specificity than to another cell type, or to another organ, or to all other cell types combined. In some embodiments, the megakaryocyte-derived extracellular vesicles home in vivo to an HSC with about a 8-fold greater specificity than to another cell type, or to another organ, or to all other cell types combined. In some embodiments, the megakaryocyte-derived extracellular vesicles home in vivo to an HSC with about a 9-fold greater specificity than to another cell type, or to another organ, or to all other cell types combined. In some embodiments, the megakaryocyte-derived extracellular vesicles home in vivo to an HSC with about a 10-fold greater specificity than to another cell type, or to another organ, or to all other cell types combined.

In embodiments, the megakaryocyte-derived extracellular vesicles are suitable for homing to a lymphatic cell in vivo. In embodiments, the megakaryocyte-derived extracellular vesicles are suitable for homing to a lymphatic cell in vitro. In some embodiments, the megakaryocyte-derived extracellular vesicles home in vivo to a lymphatic cell with about a 2-fold greater specificity than to another cell type, or to another organ, or to all other cell types combined. In some embodiments, the megakaryocyte-derived extracellular vesicles home in vivo to a lymphatic cell with about a 3-fold greater specificity than to another cell type, or to another organ, or to all other cell types combined. In some embodiments, the megakaryocyte-derived extracellular vesicles home in vivo to a lymphatic cell with about a 4-fold greater specificity than to another cell type, or to another organ, or to all other cell types combined. In some embodiments, the megakaryocyte-derived extracellular vesicles home in vivo to a lymphatic cell with about a 5-fold greater specificity than to another cell type, or to another organ, or to all other cell types combined. In some embodiments, the megakaryocyte-derived extracellular vesicles home in vivo to a lymphatic cell with about a 6-fold greater specificity than to another cell type, or to another organ, or to all other cell types combined. In some embodiments, the megakaryocyte-derived extracellular vesicles home in vivo to a lymphatic cell with about a 7-fold greater specificity than to another cell type, or to another organ, or to all other cell types combined. In some embodiments, the megakaryocyte-derived extracellular vesicles home in vivo to a lymphatic cell with about a 8-fold greater specificity than to another cell type, or to another organ, or to all other cell types combined. In some embodiments, the megakaryocyte-derived extracellular vesicles home in vivo to a lymphatic cell with about a 9-fold greater specificity than to another cell type, or to another organ, or to all other cell types combined. In some embodiments, the megakaryocyte-derived extracellular vesicles home in vivo to a lymphatic cell with about a 10-fold greater specificity than to another cell type, or to another organ, or to all other cell types combined.

In embodiments, the megakaryocyte-derived extracellular vesicles are suitable for homing to a regulatory T cell in vivo. In embodiments, the megakaryocyte-derived extracellular vesicles are suitable for homing to a regulatory T cell in vitro. In some embodiments, the megakaryocyte-derived extracellular vesicles home in vivo to a regulatory T cell with about a 2-fold greater specificity than to another cell type, or to another organ, or to all other cell types combined. In some embodiments, the megakaryocyte-derived extracellular vesicles home in vivo to a regulatory T cell with about a 3-fold greater specificity than to another cell type, or to another organ, or to all other cell types combined. In some embodiments, the megakaryocyte-derived extracellular vesicles home in vivo to a regulatory T cell with about a 4-fold greater specificity than to another cell type, or to another organ, or to all other cell types combined. In some embodiments, the megakaryocyte-derived extracellular vesicles home in vivo to a regulatory T cell with about a 5-fold greater specificity than to another cell type, or to another organ, or to all other cell types combined. In some embodiments, the megakaryocyte-derived extracellular vesicles home in vivo to a regulatory T cell with about a 6-fold greater specificity than to another cell type, or to another organ, or to all other cell types combined. In some embodiments, the megakaryocyte-derived extracellular vesicles home in vivo to a regulatory T cell with about a 7-fold greater specificity than to another cell type, or to another organ, or to all other cell types combined. In some embodiments, the megakaryocyte-derived extracellular vesicles home in vivo to a regulatory T cell with about a 8-fold greater specificity than to another cell type, or to another organ, or to all other cell types combined. In some embodiments, the megakaryocyte-derived extracellular vesicles home in vivo to a regulatory T cell with about a 9-fold greater specificity than to another cell type, or to another organ, or to all other cell types combined. In some embodiments, the megakaryocyte-derived extracellular vesicles home in vivo to a regulatory T cell with about a 10-fold greater specificity than to another cell type, or to another organ, or to all other cell types combined.

In one aspect, the disclosure provides methods of treating a myeloproliferative disease or disorder that comprise methods for transferring a deliverable therapeutic agent.

In some embodiments, the present methods for transferring a deliverable therapeutic agent, comprise: (a) obtaining an megakaryocyte-derived extracellular vesicle; (b) incubating the megakaryocyte-derived extracellular vesicle with a therapeutic agent capable of treating a myeloproliferative disease or disorder to allow the therapeutic agent to populate the lumen of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient.

In some embodiments, the present methods for transferring a deliverable therapeutic agent comprise: (a) obtaining an megakaryocyte-derived extracellular vesicle; (b) incubating the megakaryocyte-derived extracellular vesicle with a therapeutic agent capable of treating a myeloproliferative disease or disorder to allow the therapeutic agent to associate with the surface of the megakaryocyte-derived extracellular vesicle and yield a deliverable therapeutic agent; and (c) administering the deliverable therapeutic agent to a patient or contacting the deliverable therapeutic agent with a biological cell in vitro and administering the contacted biological cell to a patient.

In one aspect, the disclosure provides ex vivo methods for transferring a deliverable therapeutic agent useful for treating a myeloproliferative disease or disorder. In some embodiments, the method comprises: (a) obtaining an megakaryocyte-derived extracellular vesicle; (b) incubating the megakaryocyte-derived extracellular vesicle with a therapeutic agent capable of treating a myeloproliferative disease or disorder to allow the therapeutic agent to populate the lumen of the megakaryocyte-derived extracellular vesicle and yield a deliverable therapeutic agent; (c) obtaining a biological cell from a patient; and (d) contacting the deliverable therapeutic agent with the biological cell in vitro and administering the contacted biological cell to the patient.

In one aspect, the disclosure provides in vivo methods for transferring a deliverable therapeutic agent. In some embodiments, the method comprises: (a) obtaining an megakaryocyte-derived extracellular vesicle; (b) incubating the megakaryocyte-derived extracellular vesicle with a therapeutic agent capable of treating a myeloproliferative disease or disorder to allow the therapeutic agent to associate with the surface of the megakaryocyte-derived extracellular vesicle and yield a deliverable therapeutic agent; (c) obtaining a biological cell from a patient; and (d) contacting the deliverable therapeutic agent with the biological cell in vitro and administering the contacted biological cell to the patient.

In some embodiments, the contacting of a deliverable therapeutic agent capable of treating a myeloproliferative disease or disorder, with the biological cell comprises co-culturing the deliverable therapeutic agent with the biological cell to provide a transfer of the cargo from the deliverable therapeutic agent to the biological cell.

In embodiments, the megakaryocyte-derived extracellular vesicles bind to a cell surface receptor on a cell of the patient. In embodiments, the megakaryocyte-derived extracellular vesicles bind to a cell surface receptor on the contacted biological cell of step (c). In some embodiments, the biological cell is one or more of a cancer cell, a tumor cell, a cell infected by a virus, an epithelial cell, an endothelial cell, a nerve cell, a muscle cell, a connective tissue cell, a healthy cell, a diseased cell, a differentiated cell, and a pluripotent cell.

In embodiments, the megakaryocyte-derived extracellular vesicles fuse with the extracellular membrane of a cell of the patient. In embodiments, the megakaryocyte-derived extracellular vesicles fuse with the extracellular membrane of the biological cells of step (c). In some embodiments, the biological cell is one or more of a cancer cell, a tumor cell, a cell infected by a virus, an epithelial cell, an endothelial cell, a nerve cell, a muscle cell, a connective tissue cell, a healthy cell, a diseased cell, a differentiated cell, and a pluripotent cell.

In embodiments, the megakaryocyte-derived extracellular vesicles are endocytosed by a cell of the patient. In embodiments, the megakaryocyte-derived extracellular vesicles are endocytosed by the biological cells of step (c). In some embodiments, the biological cell is one or more of a cancer cell, a tumor cell, a cell infected by a virus, an epithelial cell, an endothelial cell, a nerve cell, a muscle cell, a connective tissue cell, a healthy cell, a diseased cell, a differentiated cell, and a pluripotent cell.

Methods of Producing Megakaryocyte-Derived Extracellular Vesicles

In some embodiments, a cell culture process is adapted to produce allogeneic megakaryocyte-derived extracellular vesicles from primary human peripheral blood CD34+ HSCs. In some embodiments, the megakaryocyte-derived extracellular vesicles are produced by a method comprising obtaining primary human peripheral blood CD34+ HSCs sourced from a commercial supplier and transitioning from a stem cell maintenance medium to an HSC expansion medium. In some embodiments, the megakaryocyte-derived extracellular vesicles are produced by a method comprising obtaining primary human cord blood CD34+ HSCs. In some embodiments, the megakaryocyte-derived extracellular vesicles are produced by a method comprising obtaining primary human bone marrow CD34+ HSCs. In embodiments, the method further involves placing HSC cultures in a megakaryocyte differentiation medium and collecting megakaryocyte-derived extracellular vesicles from culture supernatant. Accordingly, in embodiments, the present megakaryocyte-derived extracellular vesicles are produced from starting CD34+ HSCs.

In some embodiments, the megakaryocyte differentiation is confirmed by biomarker expression and/or presence of one or more of CD41, CD61, CD42b, megakaryocyte-specific cytoskeletal proteins β1-tubulin, alpha granule components (e.g. platelet factor 4 and von Willebrand Factor), secretory granules, and ultrastructural characteristics (e.g. invaginated membrane system, dense tubular system, multivesicular bodies).

In some embodiments, the megakaryocytes yield between about 10 to about 3000, about 50 to about 2600, about 80 to about 500, about 500 to about 2600, or about 500 to about 1500 megakaryocyte-derived extracellular vesicles/cell.

In some embodiments, nanoparticle analysis, electron microscopy, flow cytometry, and/or western blots are used to confirm biomarker expression and/or presence and composition of megakaryocyte-derived extracellular vesicles.

In embodiments, the megakaryocyte-derived extracellular vesicles are isolated from megakaryocytes, which are generated in the absence of added erythropoietin. In embodiments, the megakaryocyte-derived extracellular vesicles are isolated from megakaryocytes which are generated in the presence of added thrombopoietin.

In some embodiments, the megakaryocyte-derived extracellular vesicles are substantially free of nucleic acids. In some embodiments, the megakaryocyte-derived extracellular vesicles are substantially free of autologous nucleic acids. In some embodiments, the megakaryocyte-derived extracellular vesicles are substantially free of RNA. In some embodiments, the megakaryocyte-derived extracellular vesicles comprise nucleic acids. In some embodiments, the megakaryocyte-derived extracellular vesicles comprise autologous nucleic acids. In some embodiments, the megakaryocyte-derived extracellular vesicles comprise autologous RNA. Non-limiting examples of RNA include rRNA, siRNA, microRNA, regulating RNA, and/or non-coding and coding RNA. In some embodiments, the megakaryocyte-derived extracellular vesicles are substantially free of RNA from the cell from which the vesicles are derived. In non-limiting examples, the megakaryocyte-derived extracellular vesicles do not contain RNA due to the method of preparing the vesicles and/or due to the use of RNase to remove native RNAs.

In some embodiments, the megakaryocyte-derived extracellular vesicles are substantially free of autologous DNA. In some embodiments, the megakaryocyte-derived extracellular vesicles are substantially free of DNA from the cell from which the vesicles are derived. In non-limiting examples, the megakaryocyte-derived extracellular vesicles do not contain DNA due to the method of preparing the vesicles and/or due to the use of DNase to remove native DNAs. In embodiments, the megakaryocyte-derived extracellular vesicles are substantially free of one or more of: (a) megakaryocytes, (b) megakaryocyte-derived platelets, and (c) extracellular vesicles derived from platelets.

In some embodiments, frozen granulocyte colony-stimulating factor (G-CSF) mobilized human peripheral blood CD34+ cells are obtained and cultured to megakaryocytes before subsequently enriching CD41+ cells (megakaryocytes) prior to culturing, and then measuring the CD41 expression and/or presence and concentration of megakaryocyte-derived extracellular vesicles in the cell culture by flow cytometer or nanoparticle analysis. In some embodiments, the megakaryocyte-derived extracellular vesicles are generated by a series of centrifugations, e.g. at escalating speeds/force. In some embodiments, the megakaryocyte-derived extracellular vesicles are generated by: (a) removing cells from culture medium at, e.g., about 150×g centrifugation for, e.g., about 10 min; (b) removing platelet-like particles (PLPs) and cell debris by centrifugation at, e.g., about 1000×g for, e.g., about 10 min; and (c) enriching the megakaryocyte-derived extracellular vesicles from the supernatant by ultracentrifugation at, e.g., about rpm (38000×g) for, e.g., about 1 hour at, e.g., about 4° C.

In some embodiments, a multi-phase culture process with differing pH and $pO_2$ or $pCO_2$ and different cytokine cocktails is used to greatly increase megakaryocyte production.

In some embodiments, the megakaryocytes are generated by: (a) culturing CD34+ HSCs with a molecular signal/factor/cytokine cocktail that promotes megakaryocyte progenitor production; and (b) shifting cells to different conditions to expand mature megakaryocytes from progenitors. In some embodiments, commercial media is used. In some embodiments, serum-free media is used. In some embodiments, pH is shifted to increase megakaryocyte production. In some embodiments, percent $CO_2$ is shifted to increase megakaryocyte production. In some embodiments, the identity of the molecular signals/factors/cytokines is altered to increase megakaryocyte production. In embodiments, the molecular signal/factor/cytokine cocktail contains one or more of TPO, GM-CSF, IL-3, IL-6, IL-11, SCF, Flt3L, IL-9, and the like.

In embodiments, the present production methods further involve the step of characterizing the resultant megakaryocyte-derived extracellular vesicles for one or more of CD54, CD18, CD43, CD11b, CD62P, CD41, CD61, CD21, CD51, CLEC-2, LAMP-1 (CD107a), CD63, CD42b, CD9, CD31, CD47, CD147, CD32a, and GPVI. e.g., without limitation by nanoparticle analysis, electron microscopy, flow cytometry, and/or western blot analysis. In embodiments, the present production methods further involve the step of characterizing the resultant megakaryocyte-derived extracellular vesicles for phosphatidylserine, e.g., without limitation by testing for Annexin V, e.g., without limitation by nanoparticle analysis, electron microscopy, flow cytometry, and/or western blot analysis.

In some embodiments, the megakaryocyte-derived extracellular vesicles are generated from mature megakaryocytes. In some embodiments, the megakaryocyte-derived extracellular vesicles are generated from immature megakaryocytes.

In some embodiments, methods to generate megakaryocyte-derived extracellular vesicles are standardized to enable large-scale production.

In some embodiments, the present methods to generate megakaryocyte-derived extracellular vesicles inter-batch/donor variability is of less than about 20%, or less than about 15%, or less than about 10%, or less than about 5%. In some embodiments, methods to generate megakaryocyte-derived extracellular vesicles are developed such that inter-batch/donor variability is less than 12.5%. In some embodiments, methods to generate megakaryocyte-derived extracellular vesicles are developed such that inter-batch/donor variability is less than 10%. In some embodiments, methods to generate megakaryocyte-derived extracellular vesicles are developed such that inter-batch/donor variability is less than 7.5%. In some embodiments, methods to generate megakaryocyte-derived extracellular vesicles are developed such that inter-batch/donor variability is less than 5%. In some embodiments, methods to generate megakaryocyte-derived extracellular vesicles are developed such that inter-batch/donor variability is less than 2.5%.

In some embodiments, the population comprises about $1\times10^7$ or more, about $1.5\times10^7$ or more, about $5\times10^7$ or more, $1\times10^8$ or more, about $1.5\times10^8$ or more, about $5\times10^8$ or more, about $1\times10^9$ or more, about $5\times10^9$ or more, about $1\times10^{10}$ or more, or about $1\times10^{10}$ or more megakaryocyte-derived extracellular vesicles.

In some embodiments, the population comprises between about $2\times10^{10}$ to about $1\times10^{11}$, about $4\times10^{10}$ to about $9\times10^{11}$, or about $5\times10^{10}$ to about $8.5\times10^{11}$ megakaryocyte-derived extracellular vesicles.

In some embodiments, the megakaryocyte-derived extracellular vesicles are isolated as a population. In some embodiments, the population of megakaryocyte-derived extracellular vesicles is substantially homogenous.

In some embodiments, substantially all of the megakaryocyte-derived extracellular vesicles in the population comprise CD54. In some embodiments, about 0% to about 5%, about 0% to about 10%, about 15% to about 90%, about 30% to about 80%, or about 50% to about 70% of the megakaryocyte-derived extracellular vesicles in the population comprise CD54. In some embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD54. In some embodiments, less than about 30%, less than about 25%, less than about 20%, less than about 15%, less than about 10%, less than about 5%, or less than about 1% of the megakaryocyte-derived extracellular vesicles in the population comprise CD54. In some embodiments, all of the megakaryocyte-derived extracellular vesicles in the population are free of, or substantially free of CD54.

In some embodiments, substantially all of the megakaryocyte-derived extracellular vesicles in the population comprise CD18. In some embodiments, about 0% to about 5%, about 0% to about 10%, about 15% to about 90%, about 30% to about 80%, or about 50% to about 70% of the megakaryocyte-derived extracellular vesicles in the population comprise CD18. In some embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD18. In some embodiments, less than about 30%, less than about 25%, less than about 20%, less than about 15%, less than about 10%, less than about 5%, or less than about 1% of the megakaryocyte-derived extracellular vesicles in the population comprise CD18. In some embodiments, all of the megakaryocyte-derived extracellular vesicles in the population are free of, or substantially free of CD18.

In some embodiments, substantially all of the megakaryocyte-derived extracellular vesicles in the population comprise CD43. In some embodiments, about 1% to about 30%, about 1% to about 25%, about 1% to about 20%, or about 1% to about 15%, about 0% to about 5% or about 0% to about 10% of the megakaryocyte-derived extracellular vesicles in the population comprise CD43. In some embodiments, less than about 30%, less than about 25%, less than about 20%, less than about 15%, less than about 10%, less than about 5%, or less than about 1% of the megakaryocyte-derived extracellular vesicles in the population comprise CD43. In some embodiments, all of the megakaryocyte-derived extracellular vesicles in the population are free of, or substantially free of CD43.

In some embodiments, substantially all of the megakaryocyte-derived extracellular vesicles in the population comprise CD11b. In some embodiments, about 0% to about 5%, about 0% to about 10%, about 1% to about 50%, about 5% to about 40%, or about 10% to about 35% of the megakaryocyte-derived extracellular vesicles in the population comprise CD11b. In some embodiments, less than about 50%, less than about 45%, less than about 40%, less than about 35%, less than about 30%, less than about 25%, less than about 20%, less than about 15%, less than about 10%, or less than about 5% of the megakaryocyte-derived extracellular vesicles in the population comprise CD11b. In some embodiments, all of the megakaryocyte-derived extracellular vesicles in the population are free of, or substantially free of CD11b.

In some embodiments, substantially all of the megakaryocyte-derived extracellular vesicles in the population comprise CD62P. In some embodiments, about 0% to about 40%, about 0% to about 30%, about 0% to about 20%, about 0% to about 10%, or about 0% to about 5%, of the megakaryocyte-derived extracellular vesicles in the population comprise CD62P. In some embodiments, less than about 40%, less than about 30%, less than about 20%, less than about 10% of the megakaryocyte-derived extracellular vesicles in the population comprise CD62P. In some embodiments, all of the megakaryocyte-derived extracellular vesicles in the population are free of, or substantially free of CD62P.

In some embodiments, substantially all of the megakaryocyte-derived extracellular vesicles in the population comprise CD41. In some embodiments, about 15% to about 90%, about 30% to about 80%, or about 50% to about 70% of the megakaryocyte-derived extracellular vesicles in the population comprise CD41. In some embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD41.

In some embodiments, substantially all of the megakaryocyte-derived extracellular vesicles in the population comprise CD61. In some embodiments, about 40% to about 100%, about 60% to about 100%, or about 85% to about 10% of the megakaryocyte-derived extracellular vesicles in the population comprise CD61. In some embodiments, greater than about 40%, greater than about 50%, greater than about 60%, greater than about 70%, greater than about 80%, greater than about 85%, greater than about 90%, or greater than about 95%, or greater than about 99% of the megakaryocyte-derived extracellular vesicles in the population comprise CD61.

In some embodiments, substantially all of the megakaryocyte-derived extracellular vesicles in the population comprise CD21. In some embodiments, about 0% to about 10%, about 0% to about 5%, about 15% to about 90%, about 30% to about 80%, or about 50% to about 70% of the megakaryocyte-derived extracellular vesicles in the population comprise CD21. In some embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD21. In some embodiments, less than about 50%, less than about 45%, less than about 40%, less than about 35%, less than about 30%, less than about 25%, less than about 20%, less than about 15%, less than about 10%, or less than about 5% of the megakaryocyte-derived extracellular vesicles in the population comprise CD21. In some embodiments, all of the megakaryocyte-derived extracellular vesicles in the population are free of, or substantially free of CD21.

In some embodiments, substantially all of the megakaryocyte-derived extracellular vesicles in the population comprise CD51. In some embodiments, about 0% to about 10%, about 0% to about 5%, about 15% to about 90%, about 30% to about 80%, or about 50% to about 70% of the megakaryocyte-derived extracellular vesicles in the population comprise CD51. In some embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD51. In some embodiments, less than about 50%, less than about 45%, less than about 40%, less than about 35%, less than about 30%, less than about 25%, less than about 20%, less than about 15%, less than about 10%, or less than about 5% of the megakaryocyte-derived extracellular vesicles in the population comprise CD51. In some embodiments, all of the megakaryocyte-derived extracellular vesicles in the population are free of, or substantially free of CD51.

In some embodiments, substantially all of the megakaryocyte-derived extracellular vesicles in the population comprise CLEC-2. In some embodiments, about 0% to about 10%, about 0% to about 5%, or about 0% to about 12% of the megakaryocyte-derived extracellular vesicles in the population comprise CLEC-2. In some embodiments, less than about 10%, less than about 5%, or less than about 2% of the megakaryocyte-derived extracellular vesicles in the population comprise CLEC-2. In some embodiments, all of the megakaryocyte-derived extracellular vesicles in the population are free of, or substantially free of CLEC-2.

In some embodiments, substantially all of the megakaryocyte-derived extracellular vesicles in the population comprise LAMP-1 (CD107a). In some embodiments, about 0% to about 20%, about 1% to about 15%, about 2% to about 10%, about 0% to about 5%, or about 0% to about 5% of the megakaryocyte-derived extracellular vesicles in the population comprise LAMP-1 (CD107a). In some embodiments, less than about 20%, less than about 15%, less than about 10%, or less than about 5% of the megakaryocyte-derived extracellular vesicles in the population comprise LAMP-1 (CD107a). In some embodiments, all of the megakaryocyte-derived extracellular vesicles in the population are free of, or substantially free of LAMP-1 (CD107a).

In some embodiments, less than about 20%, less than about 15%, less than about 10%, or less than about 5% of a population of CD41+ megakaryocyte-derived extracellular vesicles comprise LAMP-1 (CD107a).

In some embodiments, the megakaryocyte-derived extracellular vesicles in the population are substantially free of DRAQ5. In some embodiments, about 0% to about 20%, about 0% to about 15%, about 0% to about 10%, or about 0% to about 5% of the megakaryocyte-derived extracellular vesicles in the population comprise DRAQ5. In some embodiments, less than about 20%, less than about 15%, less than about 10%, or less than about 5% of the megakaryocyte-derived extracellular vesicles in the population comprise DRAQ5.

In some embodiments, substantially all of the megakaryocyte-derived extracellular vesicles in the population comprise CD63. In some embodiments, about 1% to about 20%, about 1% to about 15%, or about 1% to about 10% of the megakaryocyte-derived extracellular vesicles in the population comprise CD63. In some embodiments, less than about 20%, less than about 15%, less than about 10%, less than about 5%, or less than about 1% of the megakaryocyte-derived extracellular vesicles in the population comprise CD63. In some embodiments, all of the megakaryocyte-derived extracellular vesicles in the population are free of, or substantially free of CD63.

In some embodiments, substantially all of the megakaryocyte-derived extracellular vesicles in the population comprise CD42b. In some embodiments, about 0% to about 20%, about 0% to about 15%, about 0% to about 10%, or about 0% to about 5% of the megakaryocyte-derived extracellular vesicles in the population comprise CD42b. In some embodiments, less than about 20%, less than about 15%, less than about 10%, less than about 5%, or less than about 1% of the megakaryocyte-derived extracellular vesicles in the population comprise CD42b. In some embodiments, all of the megakaryocyte-derived extracellular vesicles in the population are free of, or substantially free of CD42b In some embodiments, substantially all of the megakaryocyte-derived extracellular vesicles in the population comprise CD9. In some embodiments, about 40% to about 100%, about 50% to about 80%, or about 60% to about 70% of the megakaryocyte-derived extracellular vesicles in the population comprise CD9. In some embodiments, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise CD9.

In some embodiments, substantially all of the megakaryocyte-derived extracellular vesicles in the population comprise CD31. In some embodiments, about 1% to about 30%, about 1% to about 25%, about 1% to about 20%, or about 1% to about 15% of the megakaryocyte-derived extracellular vesicles in the population comprise CD31. In some embodiments, less than about 30%, less than about 25%, less than about 20%, less than about 15%, less than about 10%, less than about 5%, or less than about 1% of the megakaryocyte-derived extracellular vesicles in the population comprise CD31. In some embodiments, all of the megakaryocyte-derived extracellular vesicles in the population are free of, or substantially free of CD31.

In some embodiments, substantially all of the megakaryocyte-derived extracellular vesicles in the population comprise CD47. In some embodiments, about 1% to about 40%, about 1% to about 35%, about 1% to about 20%, about 20% to about 30%, about 30% to about 40%, or about 1% to about 15% of the megakaryocyte-derived extracellular vesicles in the population comprise CD47. In some embodiments, less than about 40%, less than about 30%, less than about 25%, less than about 20%, less than about 15%, less than about 10%, less than about 5%, or less than about 1% of the megakaryocyte-derived extracellular vesicles in the population comprise CD47. In some embodiments, all of the megakaryocyte-derived extracellular vesicles in the population are free of, or substantially free of CD47.

In some embodiments, substantially all of the megakaryo-cyte-derived extracellular vesicles in the population comprise CD147. In some embodiments, about 1% to about 30%, about 1% to about 25%, about 1% to about 20%, about 20% to about 30%, or about 1% to about 15% of the megakaryocyte-derived extracellular vesicles in the population comprise CD147. In some embodiments, less than about 30%, less than about 25%, less than about 20%, less than about 15%, less than about 10%, less than about 5%, or less than about 1% of the megakaryocyte-derived extracellular vesicles in the population comprise CD147. In some embodiments, all of the megakaryocyte-derived extracellular vesicles in the population are free of, or substantially free of CD147.

In some embodiments, substantially all of the megakaryo-cyte-derived extracellular vesicles in the population comprise CD32a. In some embodiments, about 0% to about 20%, about 1% to about 15%, or about 1% to about 10% of the megakaryocyte-derived extracellular vesicles in the population comprise CD32a. In some embodiments, less than about 20%, less than about 15%, less than about 10%, less than about 5%, or less than about 1% of the megakaryo-cyte-derived extracellular vesicles in the population comprise CD32a. In some embodiments, all of the megakaryo-cyte-derived extracellular vesicles in the population are free of, or substantially free of CD32a.

In some embodiments, substantially all of the megakaryo-cyte-derived extracellular vesicles in the population comprise GVPI. In some embodiments, about 0% to about 5%, about 0% to about 10%, about 0% to about 30%, about 0% to about 15%, or about 0% to about 10% of the megakaryo-cyte-derived extracellular vesicles in the population comprise GVPI. In some embodiments, less than about 30%, less than about 25%, less than about 20%, less than about 15%, less than about 10%, less than about 5%, or less than about 1% of the megakaryocyte-derived extracellular vesicles in the population comprise GVPI. In some embodiments, all of the megakaryocyte-derived extracellular vesicles in the population are free of, or substantially free of GVPI.

In some embodiments, substantially all of the megakaryo-cyte-derived extracellular vesicles in the population comprise phosphatidylserine. In some embodiments, about 15% to about 90%, about 30% to about 80%, or about 50% to about 70% of the megakaryocyte-derived extracellular vesicles in the population comprise phosphatidylserine. In some embodiments, greater than about 20%, greater than about 30%, greater than about 40%, greater than about 50%, greater than about 60%, greater than about 70%, greater than about 80%, greater than about 90%, or greater than about 95%, or greater than about 99% of the megakaryocyte-derived extracellular vesicles in the population comprise phosphatidylserine. In some embodiments, less than about 30%, less than about 25%, less than about 20%, less than about 15%, less than about 10%, less than about 5%, or less than about 1% of the megakaryocyte-derived extracellular vesicles in the population comprise GVPI. In some embodiments, all of the megakaryocyte-derived extracellular vesicles in the population are free of, or substantially free of phosphatidylserine.

In some embodiments, the megakaryocyte-derived extra-cellular vesicles are generated by: (a) obtaining a human pluripotent stem cell being a primary CD34+ HSC sourced from peripheral blood or cord blood; (b) differentiating the human pluripotent stem cell to a megakaryocyte in the absence of added EPO and in the presence of added TPO; and (c) isolating the megakaryocyte-derived extracellular vesicles from the megakaryocytes.

In embodiments, the method is an in vivo method. In embodiments, the method is an ex vivo method.

In embodiments, the CD34+ HSC sourced from periph-eral blood are multipotent stem cells derived from volun-teers whose stem cells are mobilized into the bloodstream by administration of a mobilization agent such as granulocyte colony stimulating factor (G-CSF) and granulocyte-macro-phage colony stimulating factor (GM-CSF).

In embodiments, the cord blood comprises multipotent stem cells derived from blood that remains in the placenta and the attached umbilical cord after childbirth.

In embodiments, the megakaryocyte-derived extracellular vesicles are autologous with the patient. In some embodi-ments, human pluripotent stem cells are extracted from the patient and used to generate megakaryocytes, from which megakaryocyte-derived extracellular vesicles comprising a cargo of choice are generated and then administered to the patient. In some embodiments, differentiated cells are extracted from the patient and used to generate iPSCs, which in turn are used to generate megakaryocytes, from which megakaryocyte-derived extracellular vesicles comprising a cargo of choice are generated and then administered to the patient.

In embodiments, the megakaryocyte-derived extracellular vesicles are allogeneic with the patient. In some embodi-ments, human pluripotent stem cells are extracted from a human subject who is not the patient and used to generate megakaryocytes, from which megakaryocyte-derived extra-cellular vesicles comprising a cargo of choice are generated and then administered to the patient. In some embodiments, differentiated cells are extracted from a human subject who is not the patient and used to generate iPSCs, which in turn are used to generate megakaryocytes, from which mega-karyocyte-derived extracellular vesicles comprising a cargo of choice are generated and then administered to the patient.

In embodiments, the megakaryocyte-derived extracellular vesicles are heterologous with the patient. In some embodi-ments, pluripotent stem cells are extracted from a non-human subject and used to generate megakaryocytes, from which megakaryocyte-derived extracellular vesicles com-prising a cargo of choice are generated and then adminis-tered to the patient. In some embodiments, differentiated cells are extracted from a non-human subject and used to generate iPSCs, which in turn are used to generate mega-karyocytes, from which megakaryocyte-derived extracellu-lar vesicles comprising a cargo of choice are generated and then administered to the patient.

In embodiments, the incubating comprises one or more of sonication, saponin permeabilization, mechanical vibration, hypotonic dialysis, extrusion through porous membranes, cholesterol conjugation, application of electric current and combinations thereof. In embodiments, the incubating com-prises one or more of electroporating, transforming, trans-fecting, and microinjecting.

In embodiments, the method further comprises (d) con-tacting the megakaryocyte-derived extracellular vesicles with radiation. In embodiments, the radiation is gamma radiation. In embodiments, the gamma radiation is at an amount greater than 12 kGy, 25 kGy, or 50 kGy. In some embodiments, the gamma radiation is at an amount between about 12 kGy and 15 kGy. In some embodiments, the gamma radiation is at an amount between about 15 kGy and 20 kGy. In some embodiments, the gamma radiation is at an amount between about 20 kGy and 25 kGy. In some embodi-ments, the gamma radiation is at an amount between about 25 kGy and 30 kGy. In some embodiments, the gamma radiation is at an amount between about 30 kGy and 35 kGy.

In some embodiments, the gamma radiation is at an amount between about 35 kGy and 40 kGy. In some embodiments, the gamma radiation is at an amount between about 40 kGy and 45 kGy. In some embodiments, the gamma radiation is at an amount between about 45 kGy and 50 kGy. In some embodiments, the gamma radiation is at an amount between about 50 kGy and 55 kGy. In some embodiments, the gamma radiation is at an amount between about 55 kGy and 60 kGy.

In embodiments, the method is substantially serum free. In some embodiments, the method is greater than 60% serum free. In some embodiments, the method is greater than 70% serum free. In some embodiments, the method is greater than 80% serum free. In some embodiments, the method is greater than 90% serum free.

In various embodiments, the megakaryocyte-derived extracellular vesicles of the disclosure are substantially purified megakaryocyte-derived extracellular vesicles. In embodiments, substantially purified is synonymous with biologically pure. In embodiments, the substantially purified megakaryocyte-derived extracellular vesicles are largely free to varying degrees from components which normally accompany it as found in its native state. "Isolate" denotes a degree of separation from original source or surroundings. In embodiments, the substantially purified megakaryocyte-derived extracellular vesicles are sufficiently free of other materials such that any impurities do not materially affect the biological properties of the megakaryocyte-derived extracellular vesicles or cause other adverse consequences. In embodiments, the substantially purified megakaryocyte-derived extracellular vesicles are sufficiently free of cellular material, viral material, or culture medium that may be needed for production. Purity and homogeneity are typically determined using biochemical techniques known in the art. In some embodiments, the megakaryocyte-derived extracellular vesicles are purified using size exclusion filtration. In some embodiments, the filter has a pore size of about 650 nm. In some embodiments, the megakaryocyte-derived extracellular vesicles are purified using size exclusion filtration. In some embodiments, the filter has a pore size ranging from about 50 nm to about 600 nm. In some embodiments, the filter has a pore size of at least 50 nm. In some embodiments, the filter has a pore size of about 600 nm.

Pharmaceutical Compositions

In one aspect, the disclosure provides compositions useful for treating a myeloproliferative disease or disorder, such as MPN, wherein the composition comprises megakaryocyte-derived extracellular vesicles of the disclosure. In another aspect, the disclosure provides a composition useful for treating a myeloproliferative disease or disorder, such as MPN, comprising a plurality of substantially purified megakaryocyte-derived extracellular vesicles comprising a lipid bilayer membrane surrounding a lumen, wherein: the megakaryocyte-derived extracellular vesicle lumen comprises cargo and/or cargo is associated with the surface of the megakaryocyte-derived extracellular vesicles; and the lipid bilayer membrane comprises one or more proteins associated with or embedded within. In some embodiments, the cargo comprises one or more agents useful for the treatment of a myeloproliferative disease or disorder, such as MPN. In some embodiments, the agent is one or more therapeutic agents, including therapeutic agents useful for the treatment of a myeloproliferative disease or disorder, such as MPN.

Therapeutic treatments comprise the use of one or more routes of administration and of one or more formulations that are designed to achieve a therapeutic effect at an effective dose, while minimizing toxicity to the patient to which treatment is administered.

In some embodiments, the effective dose is an amount that substantially avoids cell toxicity in vivo. In various embodiments, the effective dose is an amount that substantially avoids an immune reaction in a human patient. For example, the immune reaction may be an immune response mediated by the innate immune system. Immune response can be monitored using markers known in the art (e.g. cytokines, interferons, TLRs). In some embodiments, the effective dose obviates the need for treatment of the human patient with immune suppressants agents used to moderate the residual toxicity.

Upon formulation, solutions may be administered in a manner compatible with the dosage formulation and in such amount as is therapeutically effective, as described herein. The formulations may easily be administered in a variety of dosage forms such as injectable solutions and the like. For parenteral administration in an aqueous solution, for example, the solution generally is suitably buffered and the liquid diluent first rendered isotonic with, for example, sufficient saline or glucose. Such aqueous solutions may be used, for example, for intravenous, intramuscular, subcutaneous and intraperitoneal administration. Preferably, sterile aqueous media are employed as is known to those of skill in the art.

Pharmaceutical preparations may additionally comprise delivery reagents (a.k.a. "transfection reagents", a.k.a. "vehicles", a.k.a. "delivery vehicles") and/or excipients. Pharmaceutically acceptable delivery reagents, excipients, and methods of preparation and use thereof, including methods for preparing and administering pharmaceutical preparations to patients are well known in the art, and are set forth in numerous publications, including, for example, in US Patent Appl. Pub. No. US 2008/0213377, the entirety of which is incorporated herein by reference. In aspects, the present invention relates to a pharmaceutical composition comprising a composition disclosed herein and a pharmaceutically acceptable excipient or carrier.

For example, pharmaceutical compositions can be in the form of pharmaceutically acceptable salts. Such salts include those listed in, for example, *J. Pharma. Sci.* 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety. Non-limiting examples of pharmaceutically acceptable salts include: sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, di nitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, tartarate salts, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

The present pharmaceutical compositions can comprise excipients, including liquids such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In some embodiments, the pharmaceutically acceptable excipients are sterile when administered to a patient. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

In some embodiments, the pharmaceutical composition is formulated for one or more of topical, intrathecal, intra-lesional, intra-coronary, intravenous (IV), intra-articular, intramuscular, intra-nasal, and intra-endobronchial administration and administration via intrapancreatic endovascular injection, intra-nucleus pulposus, lumbar puncture, intra-myocardium, transendocardium, intra-fistula tract, inter-medullary space, intra-nasal, and intradural space injection.

In embodiments, the pharmaceutical composition is formulated for infusion. In some embodiments, the pharmaceutical composition is formulated for infusion, wherein the pharmaceutical composition is delivered to the bloodstream of a patient through a needle in a vein of the patient through a peripheral line, a central line, a tunneled line, an implantable port, and/or a catheter. In some embodiments, the patient may also receive supportive medications or treatments, such as hydration, by infusion. In some embodiments, the pharmaceutical composition is formulated for intravenous infusion. In some embodiments, the infusion is continuous infusion, secondary intravenous therapy (IV), and/or IV push. In some embodiments, the infusion of the pharmaceutical composition may be administered through the use of equipment selected from one or more of an infusion pump, hypodermic needle, drip chamber, peripheral cannula, and pressure bag.

In embodiments, the pharmaceutical composition is introduced into or onto the skin, for instance. intraepidermally, intradermally or subcutaneously, in the form of a cosmeceutical (see, e.g., Epstein, H., Clin. Dermatol. 27(5):453-460 (2009)). In embodiments, the pharmaceutical composition is in the form of a cream, lotion, ointment, gel, spray, solution and the like. In embodiments, the pharmaceutical composition further includes a penetration enhancer such as, but not limited to, surfactants, fatty acids, bile salts, chelating agents, non-chelating non-surfactants, and the like. In embodiments, the pharmaceutical composition may also include a fragrance, a colorant, a sunscreen, an antibacterial and/or a moisturizer.

In order that the invention disclosed herein may be more efficiently understood, examples are provided below. It should be understood that these examples are for illustrative purposes only and are not to be construed as limiting the invention in any manner.

EXAMPLES

Example 1: Megakaryocyte-Derived Extracellular Vesicle Generation

Figure 1A:
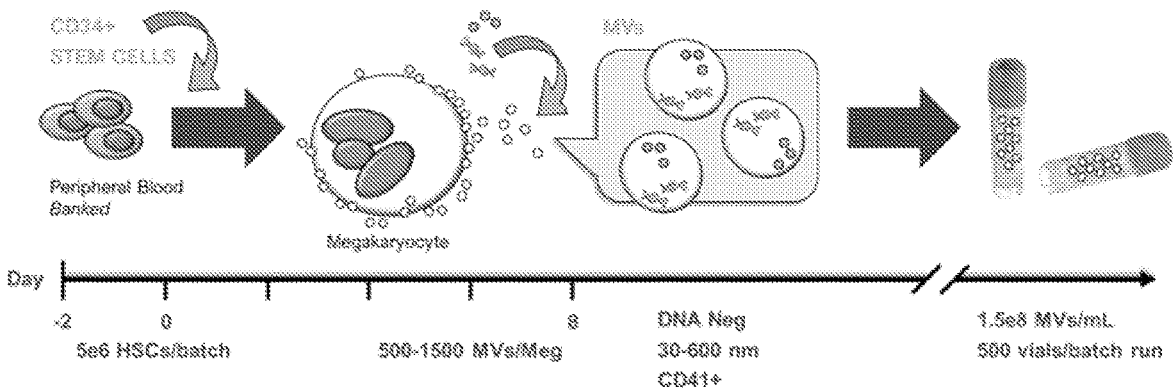
FIG. 1A is a schematic showing the differentiation steps of megakaryocyte-derived extracellular vesicles ("MkEVs" or "MVs"), with the duration of each stage, timing of harvest, and associated yields indicated.

A cell culture process was adapted to produce allogeneic megakaryocyte-derived extracellular vesicles from primary human peripheral blood CD34+ hematopoietic stem cells (HSCs) (FIG. 1A).

Primary human CD34+ HSCs sourced from a commercial supplier were thawed and transitioned from a stem cell maintenance medium to an HSC expansion medium. During this period, HSCs expanded significantly. These cultures were then placed in a megakaryocyte differentiation medium, and megakaryocyte-derived extracellular vesicles were collected from culture supernatant. Biomarker expression of CD41, CD61, CD42b, megakaryocyte-specific cytoskeletal proteins β1-tubulin, alpha granule components (platelet factor 4 and von Willebrand Factor), secretory granules, and ultrastructural characteristics (invaginated membrane system, dense tubular system, multivesicular bodies) confirmed megakaryocyte differentiation. Megakaryocytes yielded between 500-1500 megakaryocyte-derived extracellular vesicles/cell, which were between 30-600 nm in diameter, 100-300 nm, DNA−, CD41+. Megakaryocyte-derived extracellular vesicles were further isolated/concentrated by tangential flow filtration and packaged at targeted concentrations of $1.5 \times 10^8$ megakaryocyte-derived extracellular vesicles/mL. Megakaryocyte-derived extracellular vesicles exhibited robust expression of megakaryocytes and platelet-specific biomarkers, RNA, and cytosolic proteins.

Nanoparticle analysis, flow cytometry, and cryo transmission electron microscopy confirmed biomarker expression and composition.

Figure 1B:
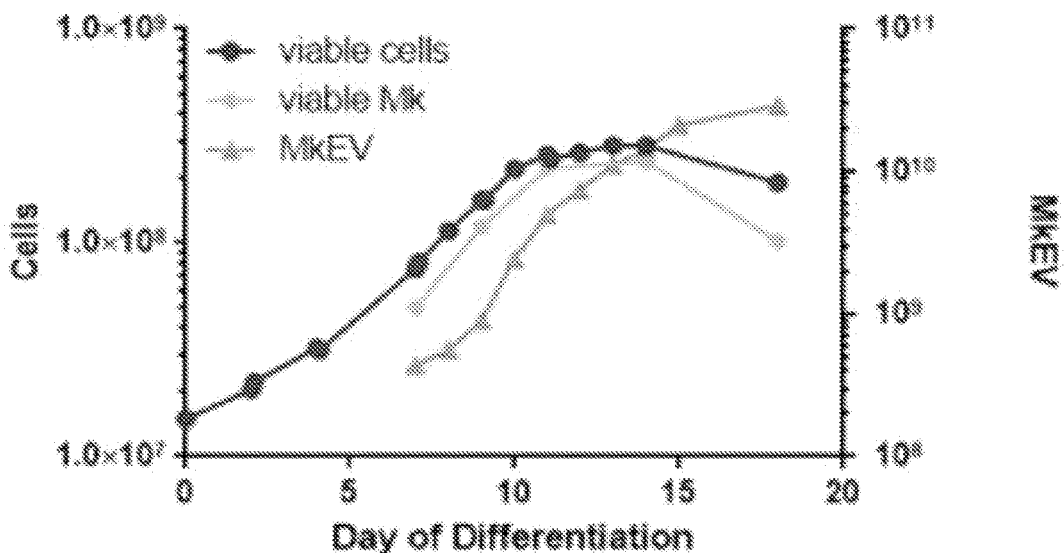
FIG. 1B is a graph of experimental data showing that the yield of megakaryocyte-derived extracellular vesicles increases over time during in vitro megakaryocyte (Mk) differentiation. For reference, at the last point, the order top to bottom is MkEV, viable cells, and viable MK.
Figure 1C:
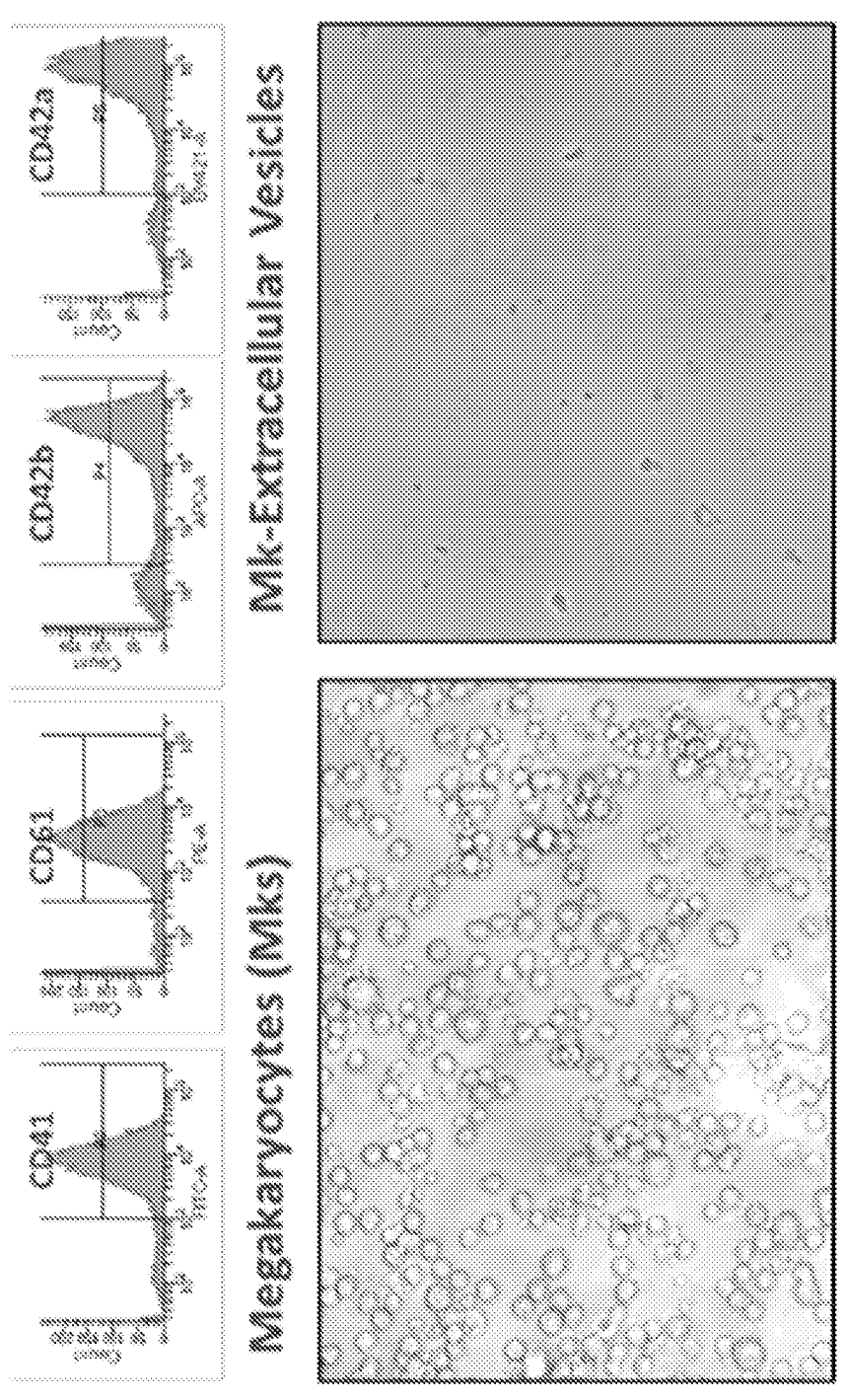
FIG. 1C is experimental data showing the phenotype of MkEVs in culture. Top panel: Representative histograms of cellular surface marker expression. Bottom panel: Representative microscopy images of megakaryocytes (left), and harvested MkEVs (right).

The yield of MkEVs was found to increase over time during in vitro megakaryocyte (Mk) differentiation (FIG. 1B). The phenotype of MkEVs in culture was assessed (FIG. 1C), and representative histograms of cellular surface marker expression and microscopy images of megakaryocytes and harvested MkEVs were produced.

MkEV biomarker expression was examined. Surface marker expression of MkEVs of the disclosure were compared to platelet-free plasma (PFP) MkEVs and platelet-derived EVs (PLT EVs) (FIGS. 2A-2E). Representative graphs demonstrating the flow cytometry gating strategy (FIGS. 2A-2B), the marker profile of CD41+ MKEVs of the disclosure, CD41+ PFP MkEVs, and CD41+ PLT EVs (FIG. 2C) and the fold change in marker expression between MkEVs of the disclosure and PFP MkEVs (FIG. 2D) and MkEVs of the disclosure and PLT EVs (FIG. 2E) are shown. The data shows that MkEVs of the disclosure exhibit different expression of surface markers compared to PFP MkEVs and PLT EVs and establish a marker profile of the present MkEVs relative to PFP MkEVs and PLT EVs. The minimal presence of DRAQ5 positive events show the lack of cellular contamination (FIG. 2F).

The size and morphology of MkEVs of the disclosure were characterized. Cryo-EM images of MkEVs of the disclosure with immunogold labeling of CD41 (FIG. 3A) and phosphatidylserine (FIG. 3B) were prepared. Measuring of MkEVs in cryo-EM images showed a range of MkEV sizes between 100-300 nm, averaging ~250 nm in diameter. FIG. 3C is an image of MkEVs isolated from PFP plasma with co-staining of CD41 (large dots) and PS (small dots) (see Brisson et al., Platelets 28:263-271 (2017), which is incorporated by reference herein in its entirety). Regarding organelle content, preliminary analysis has shown no evidence of mitochondria in MkEVs, as assessed by (1) electron microscopy, and (2) mitochondrial respiration analysis (Agilent Seahorse). Genomic analysis is conducted by sequencing of coding RNAs and non-coding miRNAs. Proteomic analysis is conducted using mass spectrometry, and proteomic data validates flow and EM surface markers.

The size of MkEVs of the disclosure is compared with PFP MkEVs using flow cytometric analysis and cryo-EM analysis with CD41+ immunogold labeling. The size distribution of MkEVs of the disclosure overlapped but were different than the size distribution of PFP MkEVs and platelet-derived EVs (FIGS. 4A-4K). (FIG. 4C is adapted from Arraud et al., Journal of Thrombosis and Haemostasis 12:614-627 (2014); FIGS. 4D and 4E are found in Brisson et al., Platelets 28:263-271 (2017), all of which are incorporated by reference herein in their entireties).

Purification of MkEVs was also examined, and size exclusion filtration was found to effectively remove aggregates from unfiltered product. For example, post-harvest filtration with a 650 nm size exclusion filter was found to successfully clear large aggregate material (observed by EM in frozen MkEV samples) (FIG. 5B) compared to unfiltered MkEV product (FIG. 5A).

Example 2: MV Manufacturing Process and Release of Product for In Vivo Gene Delivery This example is related to processes for standardizing and scaling manufacturing and isolating MkEVs from primary human CD34+ HSCs. MkEVs were characterized and inter-batch variability and release testing was performed. Gene loading and transfection efficiency for MkEVs was defined, which allows for tracking in vivo biodistribution and efficacy, and defining product parameters for gene delivery applications.

For clinical entry, MkEV manufacture must meet release criteria including standardization of tissue sourcing, manufacturing, yield, testing, and storage. MkEV quality and inter-batch variability regarding identity, purity, efficacy, and yield was defined and used to define product release criteria. MkEVs met or exceed minimum quality and storage requirements.

MkEV manufacture from primary human CD34+ cells were adapted to ~400 mL batch cultures (approx. 1200 cm² of culture area, which is equivalent to ~5×T225s) to yield ~8e10 MkEVs per batch. MkEVs underwent testing to assess identity & purity (biomarker expression, % composition) and yield (total MkEV events per batch). Table 1 shows examples of MkEV release specifications.

TABLE 1

| Examples of MkEV release specifications | | |
|---|---|---|
| TEST | METHOD | SPECIFICATIONS |
| Identity/Purity | | |
| Size | Nanoparticle analyzer | ≥95% 100-600 nm |
| DNA | High sensitivity flow cytometry | ≥95% DRAQ5 negative |
| CD41 | High sensitivity flow cytometry | ≥50% positive |
| Yield | | |
| MV Events | Nanoparticle analyzer | ≥1e10 per batch |

Standardization and scale processes to manufacture and isolate MkEVs from primary human CD34+ HSCs: Primary human CD34+ hematopoietic stem cells (HSCs) were utilized. Initial isolation, enrichment, and banking of HSCs (90-95% purity) was performed and qualified according to FDA guidance using a range of assays to demonstrate identity, sterility, viability and bank stability. HSCs were mobilized from donor marrow to the blood by granulocyte-colony stimulating factor, and collected from peripheral blood by apheresis, and tested for Chagas, CMV, HepB, HepC, HIV-1/HIV-2 Plus O, HTLV I/II, Syphilis, HBV, HCV, and WNV prior to banking (COVID-19 testing is included). HSC vials were cryopreserved in clinically approved media prior to shipping and exhibit viability post thawing. In a non-limiting example, HSC vials were cryopreserved in clinically approved media prior to shipping and exhibit viability post thawing.

Process Flow for Initial Stage MkEV Production: A scalable, cGMP-compatible process to manufacture MVs from HSCs was utilized. MkEV production was divided into 2 discontinuous segments: (A) HSC expansion, megakaryocyte differentiation and MkEV production, and (B) MV isolation/concentration by tangential flow filtration and vial filling (1.5e8 MVs/mL). MkEV vials were cryopreserved for banking. Centralized manufacturing is intended for HSC expansion and MkEV production/processing/filling.

Segment A: Primary human CD34+ HSCs at a 5e6 cells/batch underwent ~30-fold biomass expansion during cell culture to yield ~1.5e8 megakaryocytes/batch. CD34+ HSC differentiation to megakaryocyte progenitor occurred over a period of 7-9 days. Each megakaryocyte yielded between 500-1500 MVs, resulting in a total batch yield of ~7.5e10 MkEVs/batch prior to harvesting from supernatant.

Segment B: MkEVs were isolated/concentrated by tangential flow filtration (differential centrifugations as alternative if necessary) to reduce volume to ~500 mL. MkEVs were packaged at a concentration of ~1.5e8 MkEVs/mL to yield ~500 vials/batch.

Example 3: Characterization of MkEVs and Performance of Inter-Batch Variability and Release Testing MkEVs were collected from batch processing. High sensitivity flow cytometry was used to determine surface biomarker expression (CD41, CD62P, CLEC-2, LAMP-1 (CD107A)), organelle content (mitochondria), and phospholipid composition (phosphatidylserine) in combination with a nuclear dye (DRAQ5) to distinguish from nucleated cells. Total fluorescence intensity was calculated after subtraction of a fluorophore-conjugated IgG antibody specificity control. The forward and side light scatter of MkEVs were examined to evaluate size distribution, purity, and aggregation. Size-defined nanoparticles served as a gating control.

MkEV size and total batch yield were determined using a nanoparticle analyzer (Nanosight, Malvern Instruments). MkEV protein content (Alix and TSG101) was determined by ELISA and DNA content measured to estimate potential contamination by cell debris and nuclei. MkEV integrity and purity was confirmed by cryo-electron microscopy and immunogold labeling and permit further determination of surface molecules (CD41, phosphatidylserine). These experiments were repeated a number of times per batch for a number of independent MkEV batches. In a non-limiting example, the experiments were repeated at least 3 times per batch for a minimum of 3 independent MkEV batches. MkEVs/PEVs from human whole blood were used as a positive control.

Figures 6E, 6F, 6G, 6H:
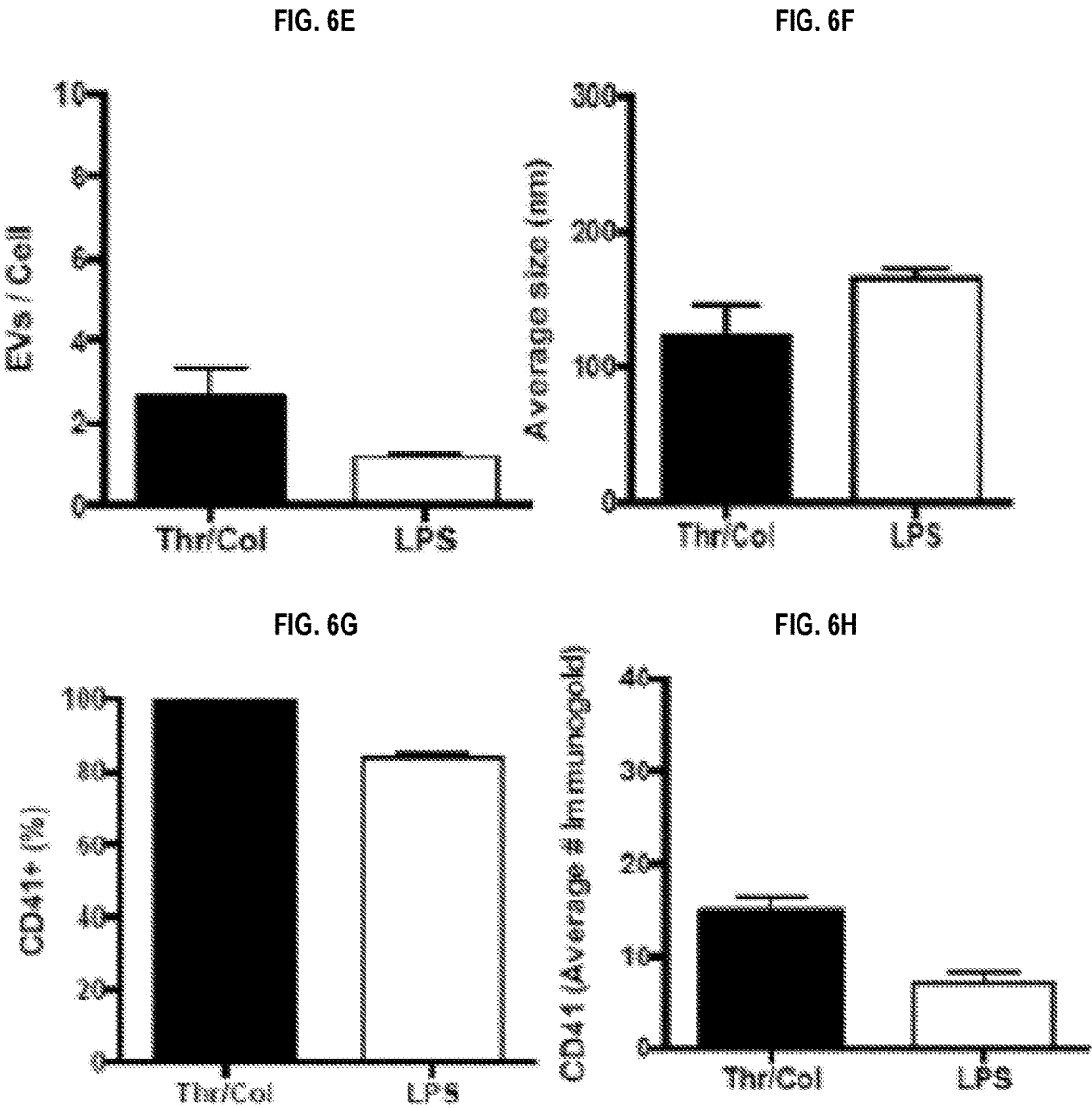

MkEVs were collected or generated from megakaryocytes and platelets, respectively, and characterized using nanoparticle tracking analysis in conjunction with immunogold labelling and electron microscopy to quantify CD41+ expression. Human CD34+-derived megakaryocytes produced between 500-1500 MkEVs per megakaryocyte (FIG. 6A), which was partway between murine bone marrow and fetal liver cell culture controls, with a similar average size of ~200 nm/MkEV (FIG. 6B). While the percentage of CD41+ MkEVs from human CD34+-derived megakaryocyte cultures were comparable to murine bone marrow-derived MkEVs, human MkEVs had more CD41-bound gold particles by immunogold electron microscopy (FIGS. 6C-6D). Human platelets activated with traditional agonists (thrombin and collagen) and inflammatory stimuli (LPS, to mimic an in vivo model) generated a similar number of EVs/platelet (FIG. 6E) and were larger in size than MkEVs (FIG. 6F) (for FIGS. 6A-6F see French et al., Blood Advances, 4:3011-3023 (2020), which is incorporated by reference herein in its entirety). Platelet-derived EVs may also contain mitochondria and other organelles (unlike MkEVs) due to their larger size. The percentage of CD41+ PEVs, and relative expression of CD41-bound gold particles by PEVs were compared to human MkEVs, and murine MkEV controls (FIGS. 6G-6H).

To evaluate inter-batch consistency, MkEVs were collected or generated from megakaryocytes and characterized using flow cytometry to quantify CD41+ expression. There was minimal inter-batch variability in total number of MkEVs/mL and total MkEVs produced per batch (FIG. 7A) and surface marker expression on manufactured MkEVs (FIG. 7B).

Example 4: Correcting JAK2-V617F Mutations Using a Genetic Editing Approach as a Therapy for Myeloproliferative Neoplasms (MPNs)

To treat JAK2-V617F mutation-positive MPNs, gene editing constructs targeting the JAK2-V617F mutation were designed and constructed. Correction of the JAK2-V617F point mutation was performed using a homology-directed repair (HDR) approach. Editing constructs were comprised of Cas9 and a sequence-specific guide RNA (sgRNA). To facilitate homology-directed repair (HDR), the editing construct was accompanied by a single stranded DNA template (ssODN). To validate the editing capacity of these novel constructs, HEL cells, a leukemic cell line containing multiple copies of the JAK2-V617F mutated allele, were electroporated with the ribonucleoprotein (RNP) and ssODN. A GFP-tagged Cas9 was used to form the RNP, enabling selection of cells that successfully internalised the RNP complex. 24-48 hours post electroporation, GFP+ cells were sorted and isolated by fluorescence-activated cell sorting (FACS) and genomic DNA was isolated and assessed for correction of the JAK2-V617F mutation (FIG. 8A). Evaluation of the genomic DNA, following simultaneous electroporation of the RNP complex and ssODN, revealed successful correction of the JAK2 mutation in GFP+ cells (FIG. 8B). Next generation sequencing (NGS) of edited cells (GFP+ cell fraction) revealed 41% editing efficiency with successful T>G replacement, restoring wild type JAK2 (FIGS. 9A and 9B). Base proportions of the uncorrected (HEL cell line) and RNP-transfected HEL cells (Corrected HEL cell line) (FIG. 9B) and proportions of insertions and deletions in uncorrected and RNP-transfected HEL cells (FIG. 9C) at the V617F point mutation locus are shown. In brief, RNP and ssODN-mediated correction reduced the V617F burden to 56%, with 41% of reads harbouring the wild-type T>G replacement (FIG. 9B). In addition, 33% of mapped reads contained an insertion or deletion at the V617F point mutation locus (FIG. 9C).

Next, HEL cells were subjected to HDR, using simultaneous transfection of RNP and ssODN, and expanded for 24- and 48 hours prior to FACS-mediated selection of RNP-containing cells. There was successful editing of the genomic DNA of HEL cells, following incubation for both 24- and 48 hours after electroporation, as shown in FIGS. 10A and 10B of Wild-type and V617F-specific amplification of genomic DNA revealed successful correction of the JAK2 mutated allele at both timepoints, with cells expanded for 24 h showing the highest level of wild-type JAK2 (JAK2-WT; FIG. 10B) and lowest JAK2-V617F burden (FIG. 10A).

Next, the editing efficacy of the editing constructs were validated using an alternative modality. In brief, a plasmid DNA (pDNA) sequence was constructed to express the sgRNA, Cas9 and a ZsGreen reporter. HEL cells were simultaneously transfected with the pDNA construct and the separate ssODN template, whereby two pDNA doses were selected. Cells were sorted for GFP positivity 24- and 48-hours post electroporation. The genomic DNA was extracted and assessed for gene editing. Similar to the pre-formed RNP complex, cells transfected with the pDNA-encoded editing complex and a separate ssODN template were successfully edited, as shown by significantly increased amplification of wild type JAK2 and reduction in JAK2-V617F burden (FIGS. 11A and 11B).

Example 5: Define Gene Loading and Transfection Efficiency for MkEVs

To define gene loading efficiency, MkEVs were electroporated with ~8300 bp pDNA encoding an MPN editing construct. MkEVs were treated with DNase to remove un-internalized pDNA. pDNA is loaded into the MkEV was isolated and quantified by qPCR. Control samples included pDNA incubated with MkEVs in the absence of electroporation±the addition of DNase. As shown in FIGS. 12A and 12B, loading of pDNA using the 4D-Nucelofector (Lonza Wakersville, Inc) was achieved with over 50-fold increase in successfully internalized pDNA into MkEVs compared to un-electroporated controls.

To define gene loading efficiency, ~500 bp, 3,000 bp, and 6,000 bp plasmid DNA are conjugated to a Cy5 fluorescent label using the Label IT Tracker Cy5 (Mirus); 4-10 label molecules per plasmid, as previously described. MkEVs re electroporated with Cy5+ labeled DNA at a ratio of $250\times10^3$ (DNA/MV) in 100 µL (15 min, 37 C) using a MaxCyte VLX—a scalable cGMP compliant electroporation system that can transfect up to 200 billion cells per batch for commercial manufacturing. MkEVs are washed to ameliorate nucleic acid of MkEV aggregation and incubated on ice for 20 min to recover, and subsequently centrifuged to remove large aggregates generated during electroporation. MkEVs are washed in PBS and resuspended in co-culture medium for transfection studies. To define pDNA copy number, pDNA are purified from loaded MkEVs using the QIAprep Spin Miniprep Kit (Qiagen), and its concentration is quantified using the Qubit dsDNA HS Assay Kit (Invitrogen).

Loading efficiency (%)=Cy5+MV#/Total MV# pDNA copy#=[Loaded pDNA (ng)*10^9/Molecular Weight]*Avogadro's Number

Cy5 refers to the number of Cy5-positive megakaryocyte vesicles; MV# refers to the number of megakaryocyte vesicles; Loaded pDNA refers to the amount of pDNA loaded into the MVs; Molecular Weight refers to the molecular weight of the pDNA.

pDNA copy number is confirmed by quantitative PCR amplification of portion of plasmid DNA and amplicons visualized by gel electrophoresis. To define in vitro transfection efficiency MkEVs are co-cultured with CD34+ HSCs at a ratio of 25, 50, 100 MkEVs per HSC and centrifuged at 600×g for 30 min at 37° C., using previously described methods (Kao and Papoutsakis, Science Advances 4:1-11 (2018), which is incorporated by reference herein in its entirety). The percentage of Cy5+ HSCs is quantified at 24, 48, and 72 hours by flow cytometry. To define nuclear transfection efficiency nuclei are isolated for HSCs at 24 hrs as previously described, and the percent of Cy5+ nuclei quantified by flow cytometry.

Loading efficiencies per MkEV are expected to be proportionate to pDNA size; and ~50-60% transfection efficiencies. Loading efficiency and capacity of DNA in EVs are expected to be dependent on DNA size, with linear DNA molecules less than 1000 bp in length being more efficiently associated with MkEVs compared to larger linear DNAs and plasmid DNAs using this approach. If pDNA loading efficiencies are limiting, these studies are repeated with linear DNA and results compared to historical studies in other MkEVs. Other non-limiting methods for loading genetic material into MkEVs include sonication, saponin permeabilization, hypotonic dialysis, cholesterol conjugation, and megakaryocyte microinjection/transfection. Transfection efficiency studies inform in vivo dosing strategy.

To define protein loading efficiency, MkEVs were electroporated with Cas9 protein. Following electroporation, MKEVs were treated with Proteinase K to digest any un-internalized protein cargo, then lysed and subject to western blotting analysis to quantify Cas9 loading. Controls included MkEVs plus Cas9 without electroporation±Proteinase K. As shown in FIG. 13, in the absence of electroporation, Cas9 was completely digested by Proteinase K. When MkEVs were electroporated with Cas9, Cas9 persisted following exposure to Proteinase K, indicating successful protection of the Cas9 protein cargo by MkEVs.

Example 6: Use of Megakaryocyte-Derived Extracellular Vesicles (MK EVs) as a Therapeutic Delivery Vehicle in Myeloproliferative Neoplasms (MPNs)

To test the ability of loaded MkEVs to enter hematopoietic stem and progenitor cells (HSPCs) in vitro, MkEVs were loaded with MPN targeted ribonucleoprotein (RNP) and passed through 300 KDa filters to remove any unloaded protein. Primary bone marrow cells were harvested from mice carrying the cDNA sequence of human JAK2, harbouring the V617F mutation, depleted of lineage-positive cells (B-cell, T-cell, erythroid, and granulocyte populations) and remaining lineage negative cells (an HSPC enriched population) were co-cultured in vitro for 4 hours with MkEVs loaded with GFP-tagged Cas9 by electroporation. Doses were 80, 155, and 465 MkEVs/cell. Controls included unloaded cells, cells co-cultured with unloaded MkEVs and cells co-cultured with GFP-tagged RNP alone, processed in parallel to MkEVs (i.e. undergoing the 300 KDa filtration). Flow cytometry demonstrated a clear population of GFP+ cells, indicating successful MkEV uptake/association with HSPCs (FIG. 14A). In contrast, cells subjected to RNP only (filtered) did not show GFP positivity (FIG. 14A). The percentage of GFP+ cells increased with increasing dose (FIG. 14B). FIG. 14C shows median fluorescent intensity (MFI) in the GFP+ cell population. Co-culture of the cargo-loaded MkEVs with lineage negative cells at the same three doses but for 14 hours instead of 4 hours (FIGS. 15A-15C), led to successful MkEV uptake as evidenced by GFP+ cells (FIG. 15A, 15B) and demonstrated increased median fluorescence intensity with increasing doses of MkEVs (FIG. 15C) in the GFP+ cells. The prolonged incubation time increased the proportion of GFP+ cells to >2%. There was even greater MkEV association with lineage negative cells following 18 hours in culture, with 17% of lineage negative cells positive for expressing GFP positivity due to cargo-loaded MkEV mediated delivery (FIG. 16A, 16B). An increase in the MkEV:cell ratio resulted in a proportional increase in the proportion of GFP+ cells and the median fluorescent intensity (FIG. 16 B, FIG. 16C). Collectively, these results indicate MkEV-mediated delivery of RNP to primary lineage-depleted bone marrow cells.

MkEVs were also found to preferentially target primitive HSPCs (FIGS. 17A-17C). Lineage-depleted co-cultured with RNP-loaded MkEVs for 18 h were stained for HSPC-specific markers (c-Kit and Sca-1) to determine the phenotype of cells targeted by MkEVs. Flow analysis of Lineage negative/c-Kit+/Sca-1+ (LSK) cells, a primitive HSPC population, was performed for GFP+ and GFP– cell fractions (FIG. 17A). An increase in the MkEV:cell ratio was accompanied by an increase in the proportion of LSK cells in the GFP+ fraction (FIG. 17A). A dose of 600 MkEVs/cell was sufficient to target the majority of LSK cells (FIGS. 17A, 17B), These data suggest that MkEVs selectively target the naïve HSPC compartment in vitro. Confocal microscopy of GFP+ cells following co-culture with 600 MkEVs/cell confirmed the MkEV-mediated delivery of the RNP complex to target cells (FIG. 17C). Imaging revealed the internalization of GFP signal in target cells (FIG. 17C).

To determine the efficacy of MkEV-mediated delivery of the RNP complex to HSPCs, RNP-loaded MkEVs were supplemented to primary LSK cells in vitro (FIGS. 18A, 18B, 19A, 19B). For this purpose, LSK cells were freshly isolated from mice carrying a heterozygous (HET) and homozygous (HOM) JAK2-V617F mutation. Cells were seeded (20,000 cells for HOM and 15,000 cells for HET) and incubated for 24 h prior to 14 h co-culture with RNP-loaded MkEVs. HOM JAK2-V617F cells were co-cultured with RNP-loaded MkEVs at two different doses (670 MkEVs/cell and 2000 MkEVs/cell). In addition, one dose of 670 MkEVs/cell was supplied by MkEVs+ RNP in the absence of electroporation. The control sample was comprised of filtered RNP without the supplement of MkEVs. Co-culture of JAK2-V617F HOM LSK cells with loaded MkEVs introduced a dose-dependent delivery of RNP to 19% and 36% of LSK cells, respectively (FIG. 18A, FIG. 18B). MkEVs, incubated with RNP in absence of electroporation, resulted in the detection of GFP+ cells. While not wishing to be bound by any particular theory, this result suggested that MkEVs facilitate uptake and/or association of RNP to target cells. HET JAK2-V617F LSK cells were co-cultured with RNP-loaded MkEVs at the following two doses: 890 MkEVs/cell and 2570 MkEVs/cell. In line with the increase in MkEV/cell ratio, the proportion of GFP+ LSK cells was increased to 28% and 45% respectively (FIG. 19A, FIG. 19B). As outlined in FIGS. 18A-18B, co-culture with RNP-associated MkEVs in absence of electroporation resulted in 23% GFP positivity amongst LSK. Collectively, these data demonstrate that MkEVs facilitated the efficient association/uptake of the therapeutic RNP complex by primary HSPCs, harboring the JAK2-V617F mutation.

Test MK EVs for their ability to correct the V617F mutation in vitro: MK EVs are developed to target the JAK2 V617F mutation in vitro. Assays are performed in a patient-derived JAK2 V617F mutated cell line (HEL) and are compared against the current gold standard in the field (viral vector delivery) to benchmark efficiency. Primary cell cultures of mouse HSCs isolated from the JAK2 V617F mouse model and wild-type littermates are tested for gene targeting in vitro using established assays as previously disclosed. See, e.g., Shepherd et al., "Single-cell approaches identify the molecular network driving malignant hematopoietic stem cell self-renewal," Blood 132:791-803 (2018), which is incorporated by reference herein in its entirety.

In vivo testing in JAK2 V617F mouse model: The JAK2 V617F mouse model has a robust and trackable phenotype observable from 4 weeks of age (90% haematocrit, red hands/feet, excess red cell progenitors, EPO-independence, stem cell defect). See Li and Kent et al., "JAK2V617F homozygosity drives a phenotypic switch in myeloproliferative neoplasms, but is insufficient to sustain disease," Blood 123:3139-3153 (2014), which is incorporated by reference herein in its entirety. These mice are given the MK EVs developed to target the JAK2 V617F mutation and the blood cell phenotype is tracked. The inherent stem cell defect renders gene-corrected cells at an advantage, thereby enhancing the impact of potential low gene correction efficiencies.

Validation of gene targeting in primary patient HSCs: JAK2 V617F mutated patient samples are grown in a suite of single cell assays to determine the growth and differentiation potential and mutational status of single HSCs. See Ortmann and Kent et al., "Effect of Mutation Order on Myeloproliferative Neoplasms," N. Engl. J. Med. 372:601-612 (2015), which is incorporated by reference herein in its entirety. This permits robust measurements of gene correction efficiencies and impact on function of primary patient HSCs, which are useful for pre-clinical experiments in patients.

Example 7: Cancer Model for MPNs

JAK2 V617F is targeted in vitro by designing the targeting construct. The cargo is loaded into the MK EVs, which transduce mutant cell lines and primary mouse stem/progenitor cells. The recombination efficiency is then assessed.

The patient samples are next validated in vitro. Primary patient samples are obtained (e.g. from Cambridge Blood Stem Cell Biobank). Human CD34+ stem/progenitor cells are transduced, and cell function (e.g., EPO-independence) is assessed in vitro.

After in vitro validation of patient samples, JAK2 V617F is targeted in vivo. Mouse JAK V617 knock-in model (see, for example, Li et al., Blood. 2010; 116(9):1528-38, and Blood. 2014; 123(20):3139-51, both of which are incorporated by reference herein in their entireties) is utilized, and the human JAK2 V617F mutation (a known stem cell defect of mutant cells) is knocked into the mouse locus. Mice are treated in vivo with MK EVs, and cell function (robust trackable phenotype in red cells) is assessed in vivo using a homozygous humanized JAK2-V617F mouse model. MkEVs cargo loaded with MPN-targeted gene editors are injected intravenously into JAK2-V617F mutant mice and at discrete time-points following intravenous (IV) administration, bone marrow is isolated and bone marrow cellular sub-populations are analyzed for editing efficiency by qPCR and NGS. The phenotype of the mice including peripheral blood complete blood counts with differential is analyzed. Erythropoietin (Epo)-independent growth assays are performed to quantify the correction of Epo-independent growth in edited cells. Edited HSPCs are isolated and tested for stem cell capacity in bone marrow transplantation assays.

Successful in vivo gene correction is demonstrated in patient derived xenograft (PDX) models. PDXs in immunodeficient mice are utilized. Xenografts of human:mouse blood system are established and treated in vivo with MK EVs. Gene correction durability and the impact on molecular/cellular biology of engrafted cells are assessed.

Preclinical safety and quality control testing are established. Whole genome sequencing and transcriptional profiling of gene corrected cells are examined. In vivo experiments for durable gene/disease correction are monitored.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A method for gene editing a cell comprising a mutation in JAK2 gene, the method comprising (a) contacting the cell with a composition comprising a plurality of substantially purified megakaryocyte-derived extracellular vesicles comprising a lipid bilayer membrane surrounding a lumen, wherein:

the megakaryocyte-derived extracellular vesicle lumen comprises a cargo comprising an agent suitable for gene editing the cell and/or cargo comprising an agent suitable for gene editing the cell is associated with the surface of the megakaryocyte-derived extracellular vesicles; and the lipid bilayer membrane comprises two or more proteins associated with or embedded within, wherein the two proteins are CD31 and CD47, and (b) gene editing the cell to alter the mutation in the JAK2 gene therein.

2. The method of claim 1, wherein the lipid bilayer membrane further comprises one or more proteins selected from CD54, CD18, CD43, CD11b, CD62P, CD41, CD61, CD21, CD51, CLEC-2, LAMP-1 (CD107a), CD63, CD42b, CD9, CD147, CD32a, and GPVI and/or the lipid bilayer membrane further comprises phosphatidylserine.

3. The method of claim 1, wherein the megakaryocyte-derived extracellular vesicles are substantially free of:

(a) megakaryocytes, (b) platelets, and/or (c) autologous DNA.

4. The method of claim 1, wherein the megakaryocyte-derived extracellular vesicles are suitable for homing to at least one cell or tissue selected from a hematopoietic stem cell, bone marrow, a lymphatic cell, and a regulatory T cell in vivo and/or in vitro.

5. The method of claim 1, wherein the cargo is in the lumen and/or the cargo is associated with the surface of the megakaryocyte-derived extracellular vesicles.

6. The method of claim 1, wherein the agent is one or more therapeutic agents comprising a nucleic acid therapeutic agent selected from one or more non-autologous and/or recombinant nucleic acid constructs selected from mRNA, tRNA, rRNA, siRNA, microRNA, regulating RNA, non-coding and coding RNA, linear DNA, DNA fragments, or DNA plasmids.

7. The method of claim 6, wherein the nucleic acid therapeutic agent is mRNA, and optionally: is in vitro transcribed or synthetic and/or comprises one or more non-canonical nucleotides, optionally selected from pseudouridine and 5-methoxyuridine.

8. The method of claim 6, wherein the nucleic acid therapeutic agent encodes a functional protein, a gene-editing protein and/or associated elements for gene-editing functionality, wherein the gene-editing protein is selected from a zinc finger (ZF), transcription activator-like effector (TALE), meganuclease, and clustered regularly interspaced short palindromic repeat (CRISPR)-associated protein.

9. The method of claim 8, wherein the CRISPR-associated protein is selected from Cas9, xCas9, Cas12a (Cpf1), Cas13a, Cas14, CasX, CasY, a Class 1 Cas protein, a Class 2 Cas protein, MAD7, and gRNA complexes thereof.

10. The method of claim 1, wherein the megakaryocyte-derived extracellular vesicles are derived from a human pluripotent stem cell, optionally wherein the human pluripotent stem cell is a primary CD34+ hematopoietic stem cell, wherein the primary CD34+ hematopoietic stem cell is sourced from cord blood or peripheral blood optionally comprising a granulocyte colony-stimulating factor-mobilized adult peripheral blood (mPB), and wherein the human pluripotent stem cell is an embryonic stem cell (ESC) or an induced pluripotent stem cell (iPS).

11. The method of claim 1, wherein the megakaryocyte-derived extracellular vesicles are isolated from megakaryocytes, which are generated in the absence of added erythropoietin and/or in the presence of added thrombopoietin.

12. The method of claim 1, wherein the mutation in the JAK2 gene is V617F mutation.

* * * * *

SEQUENCE LISTING

<160> NUMBER OF SEQ ID NOS: 1

<210> SEQ ID NO 1
<211> LENGTH: 401
<212> TYPE: DNA
<213> ORGANISM: Artificial Sequence
<220> FEATURE:
<223> OTHER INFORMATION: Synthetic Sequence

<400> SEQUENCE: 1
ttgtatcctc atctatagtc atgctgaaag taggagaaag tgcatcttta ttatggcaga      60
gagaattttc tgaactattt atggacaaca gtcaaacaac aattctttgt actttttttt     120
ttccttagtc tttctttgaa gcagcaagta tgatgagcaa gctttctcac aagcatttgg     180
ttttaaatta tggagtatgt gtctgtggag acgagagtaa gtaaaactac aggctttcta     240
atgcctttct cagagcatct gtttttgttt atatagaaaa ttcagtttca ggatcacagc     300
taggtgtcag tgtaaactat aatttaacag gagttaagta tttttgaaac tgaaaacact     360
gtaggactat tcagttatat cttgtgaaaa aggaaagcaa t                        401